(12) United States Patent
Jaramillo et al.

(10) Patent No.: US 8,017,599 B2
(45) Date of Patent: Sep. 13, 2011

(54) SEQUENCE SELECTIVE PYRROLE AND IMIDAZOLE POLYAMIDE METALLOCOMPLEXES

(75) Inventors: David Jaramillo, Arncliffe (AU); Craig Brodie, Kentlyn (AU); Warren Howard, Mt. Annan (AU); Robin Taleb, Campbelltown (AU); Janice Aldrich-Wright, St. Clair (AU)

(73) Assignee: University of Western Sydney, Werrington, New Wales (AU)

( * ) Notice: Subject to any disclaimer, the term of this patent is extended or adjusted under 35 U.S.C. 154(b) by 1099 days.

(21) Appl. No.: 10/574,995

(22) PCT Filed: Oct. 7, 2004

(86) PCT No.: PCT/AU2004/001368
§ 371 (c)(1),
(2), (4) Date: Mar. 6, 2007

(87) PCT Pub. No.: WO2005/033077
PCT Pub. Date: Apr. 14, 2005

(65) Prior Publication Data
US 2007/0265240 A1 Nov. 15, 2007

(30) Foreign Application Priority Data
Oct. 7, 2003 (AU) ................................ 2003905512

(51) Int. Cl.
*A61K 31/555* (2006.01)
*C07F 15/00* (2006.01)
(52) U.S. Cl. ........... 514/188; 546/12; 548/109; 548/402
(58) Field of Classification Search .................. 514/188; 546/12; 548/109, 402
See application file for complete search history.

(56) References Cited

U.S. PATENT DOCUMENTS
4,942,227 A    7/1990  Dervan

FOREIGN PATENT DOCUMENTS
| WO | WO 98/49142 A1 | 11/1999 |
| WO | WO 99/62551 A1 | 12/1999 |
| WO | WO 03/020877 A2 | 8/2002 |
| WO | WO 03/041128 A2 | 5/2003 |

OTHER PUBLICATIONS

Andronova et al., "Antiherpetic activity of bis-netropsin derivatives", *Doklady Akademil Nauk*, 2001, vol. 380, No. 4, pp. 548-551 (abstract XP-002478453).

Surovaya et al., "Effect of DNA Local Conformation on the Binding of *bis*-Netropsins in the DNA Minor Groove," *Molecular Biology*, 1999, vol. 33, No. 4, pp. 539-546, American Society for Microbiology, Washington, D.C.

Kittler et al., "Sequence-specific interactions of minor groove binders with restriction fragments of cDNAs for H Tau 40 protein and MAP kinase 2. A qualitative and quantitative footprinting study", *Journal of Molecular Recognition*, 1999, vol. 12, pp. 121-130, John Wiley & Sons Ltd., Hoboken, New Jersey.

Baraldi, Pier Giovanni; et al. "Design, Synthesis and in vitro Cytotoxicity of a cis-Dichloplatinum (II) Complex Linked to the Minor Groove Binder Stallimycin" (2003) Drug Res. 53, No. 2, 107-113.

Belitsky, Jason M. et al., Cellular Uptake of N-Methylpyrrole/N-Methlyimidazole Polyamide-Dye Conjugates, Bioorganic & Medicinal Chemistry 10 (2002) 3313-3318.

Pitie, Marguerite, et al. "Mechanisms of DNA Cleavage by Copper Complexes of 3-Clip-Phen and of its Conjugate with a Distamycin Analogue"Nucleic Acids Research, 2000, vol. 28, No. 24. 4856-4864.

Loskotova, Hana and Viktor Brabek, "DNA interations of cisplastin tethered to the DNA minor groove binder distamycin" Eur. J. Biochem (1999) 266, 392-402.

Swalley, Suzanne E. et al., Effects of γ-Turn and β-Tail Amino Acids on Sequence Specific Recognition of DNA by Hairpin Polyamides J. of the American Chemical Society (1999) vol. 121, No. 6, 1113-1120.

Lee, Moses et al.,"Novel Platinum (II) Derivatives of Analogues of Netropsin and Distamycin Synthesis, DNA Binding and Cytotoxic Properties" Med. Chem. Res. (1996) 365-371.

Sigurdsson, Snorri Th. and Paul B. Hopkins "Synthesis and Reactions with DNA of a Family of DNA-DNA Affinity Cross-Linking Agents" (1994) Tetrahedron, vol. 50, No. 42 12065-12084.

Huang, Liren et al., "Design of DNA-Cleaving Molecules Which Incorporate a Simplified Metal-Complexing Moiety of Bleomycin and Lexitropsin Carriers" Bioorganic & Medicinal Chemistry Letters, Vo. 3, No. 8, 1751-1756, (1993).

*Primary Examiner* — Joseph Kosack
(74) *Attorney, Agent, or Firm* — Buchanan Ingersoll & Rooney PC

(57) ABSTRACT

The present invention relates to sequence selective compounds for targeting therapeutic or diagnostic groups to polynucleotides. More particularly, the present invention relates to sequence selective targeting of metallocomplexes, such as metallodrugs and metallodiagnostics, to polynucleotides.

2 Claims, 20 Drawing Sheets

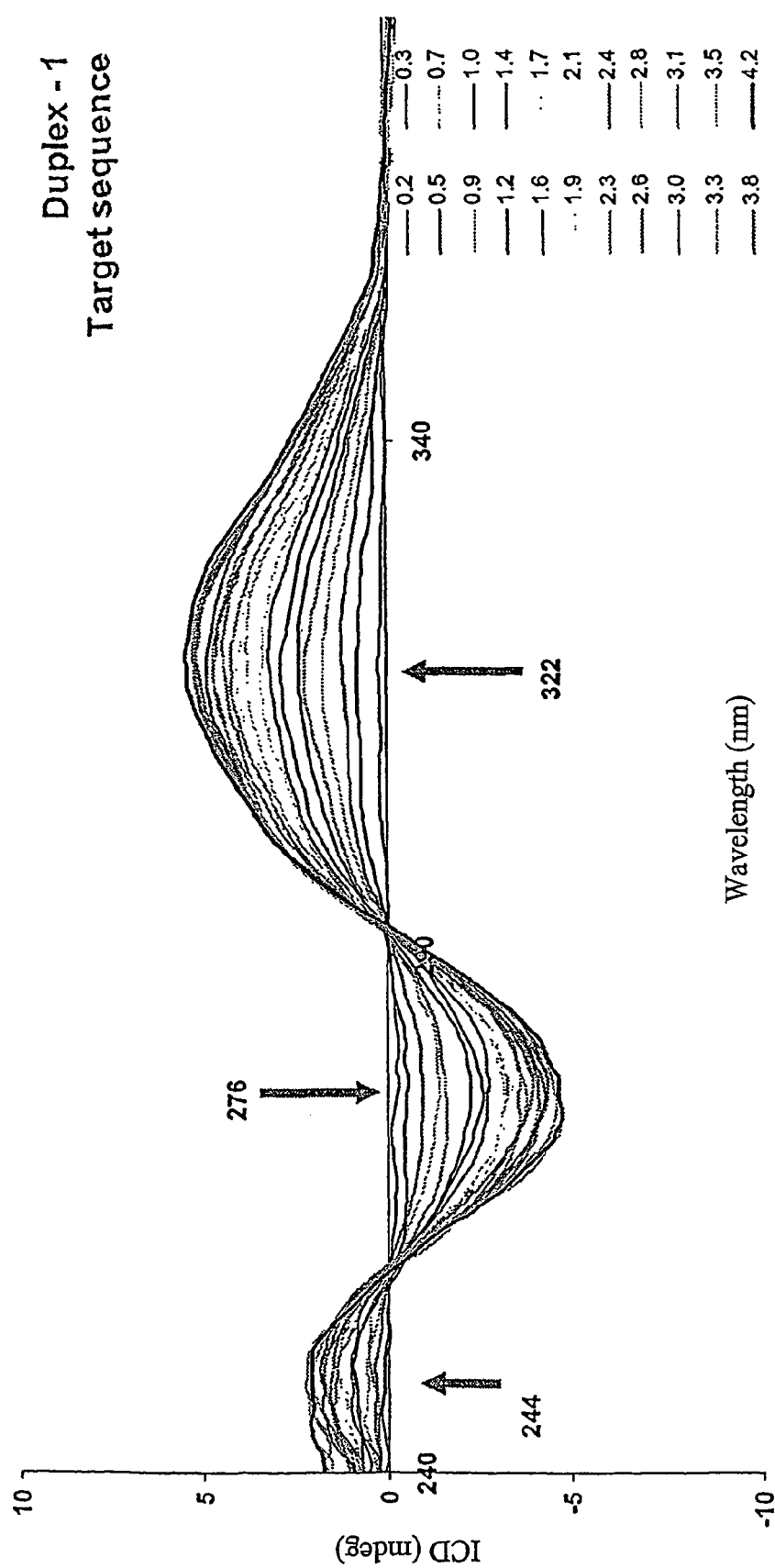
Figure 3(a)(ii)

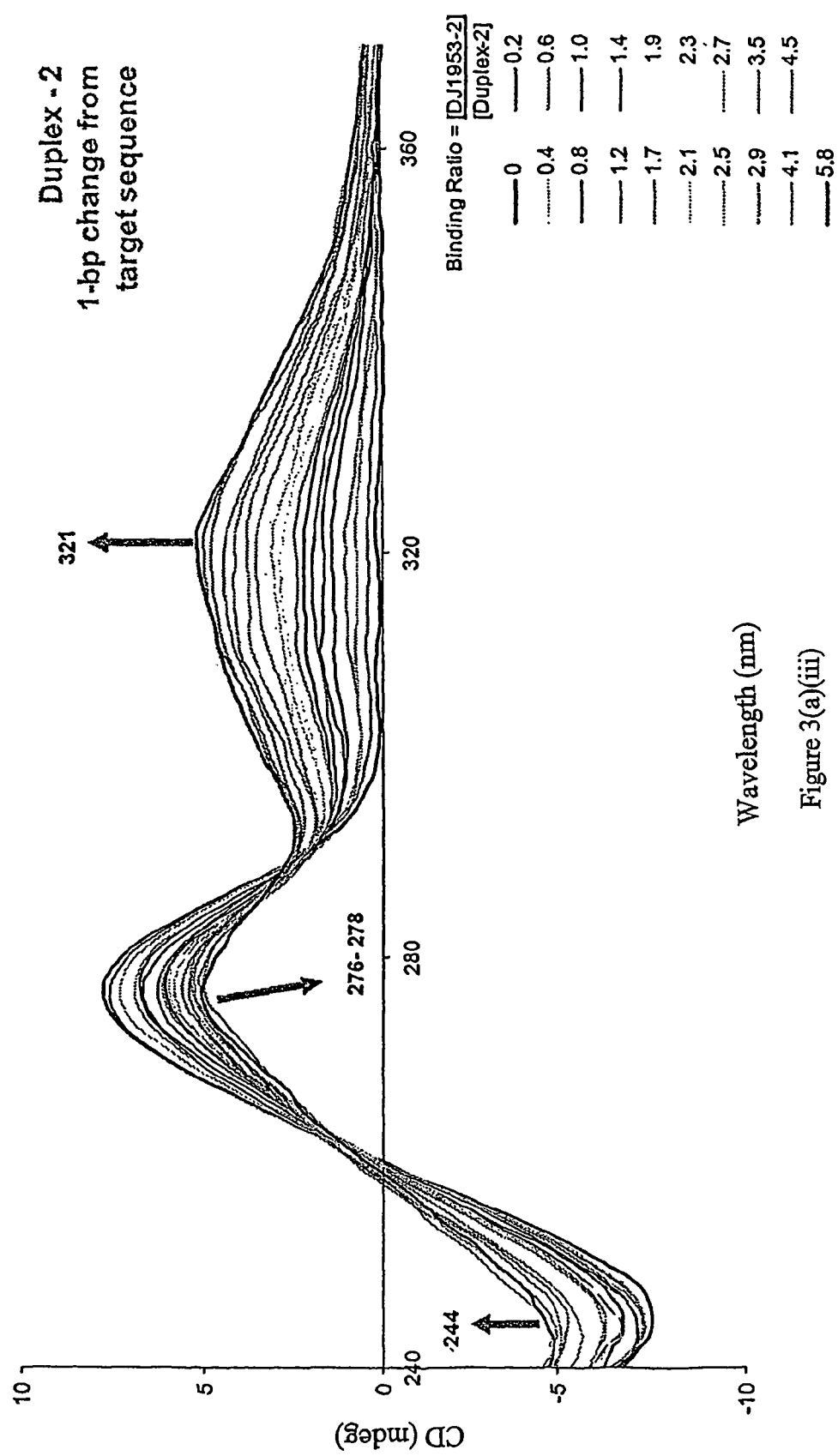
Figure 3(a)(iii)

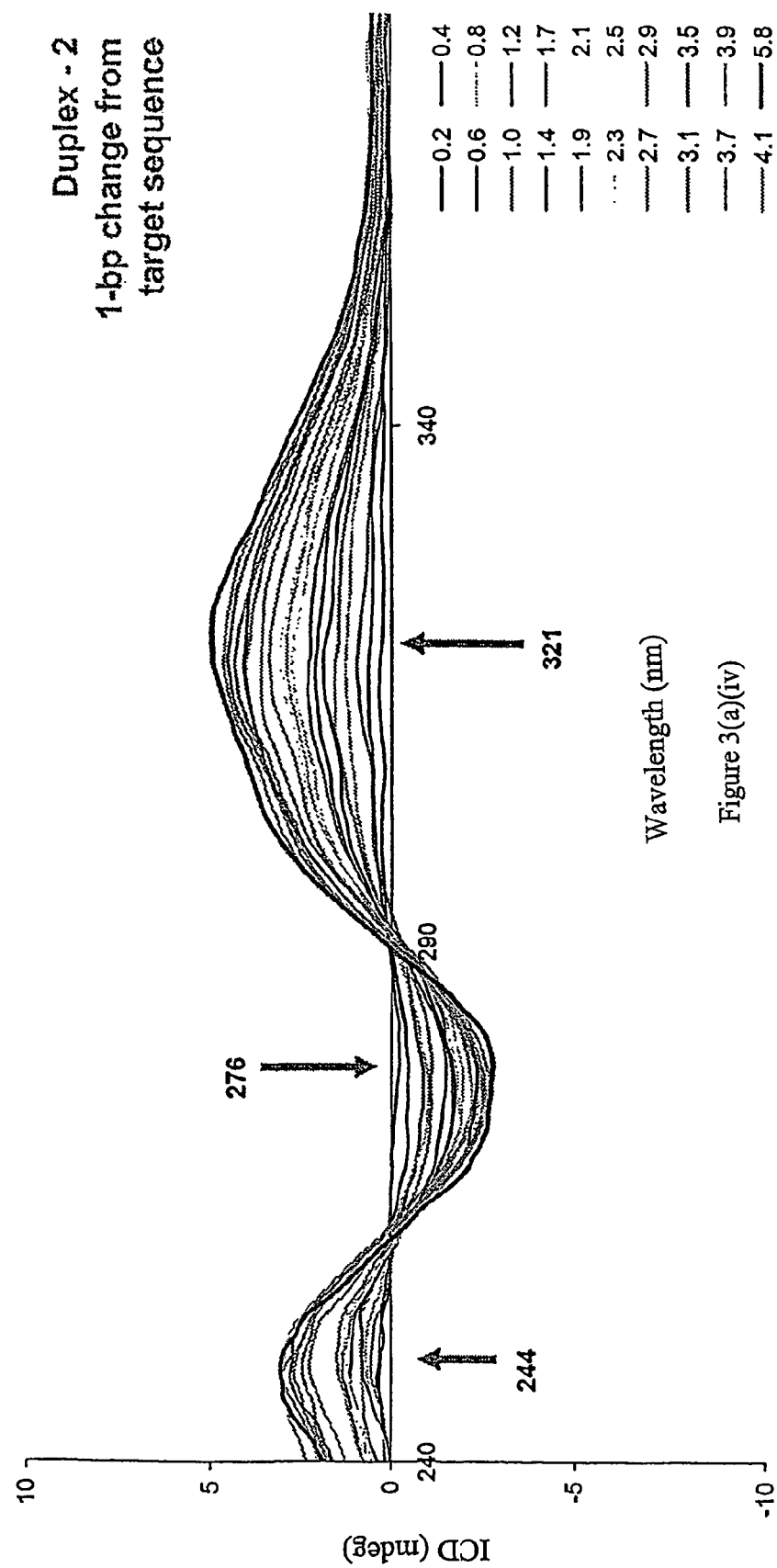
Figure 3(a)(iv)

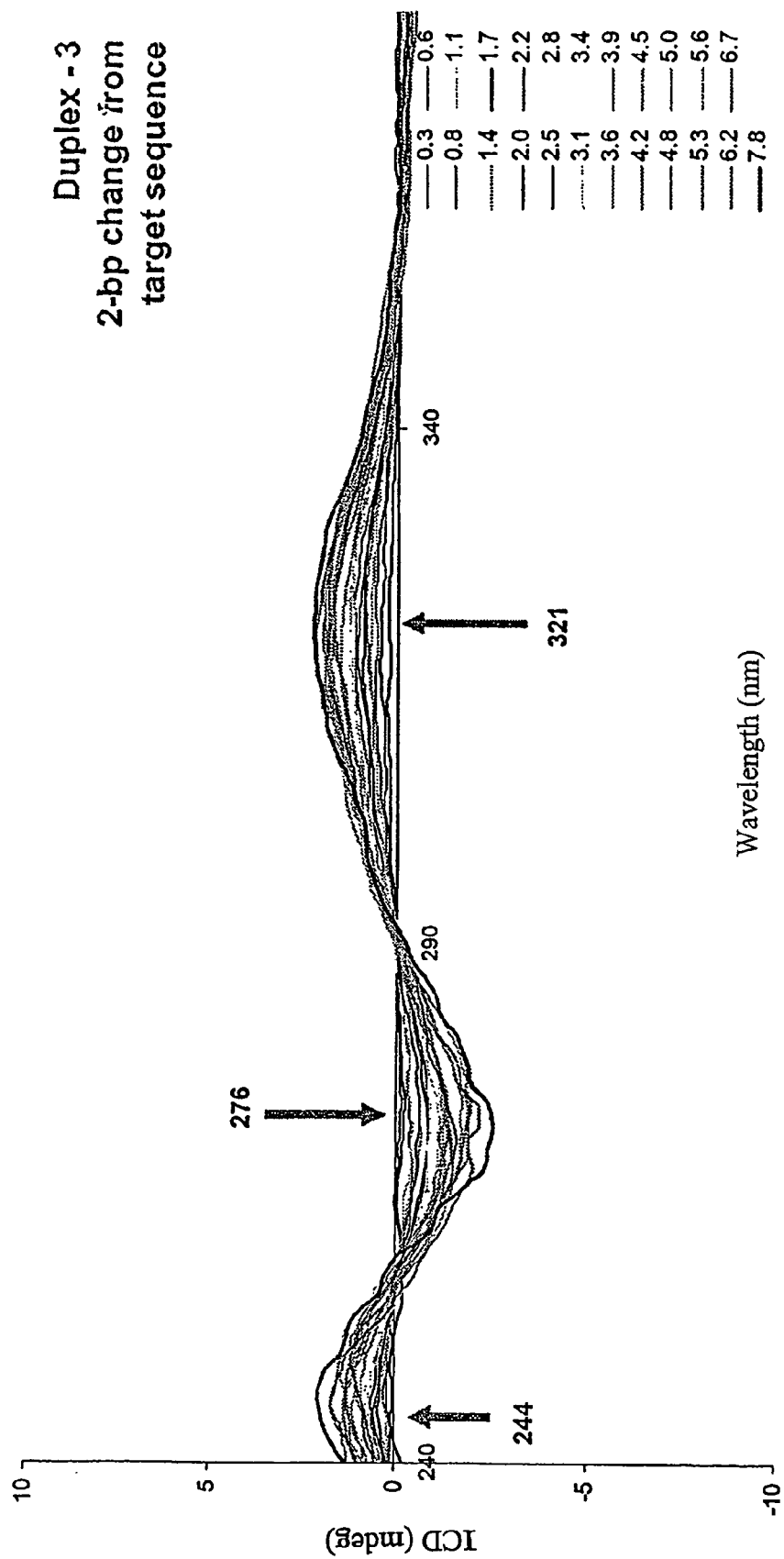
Figure 3(a)(vi)

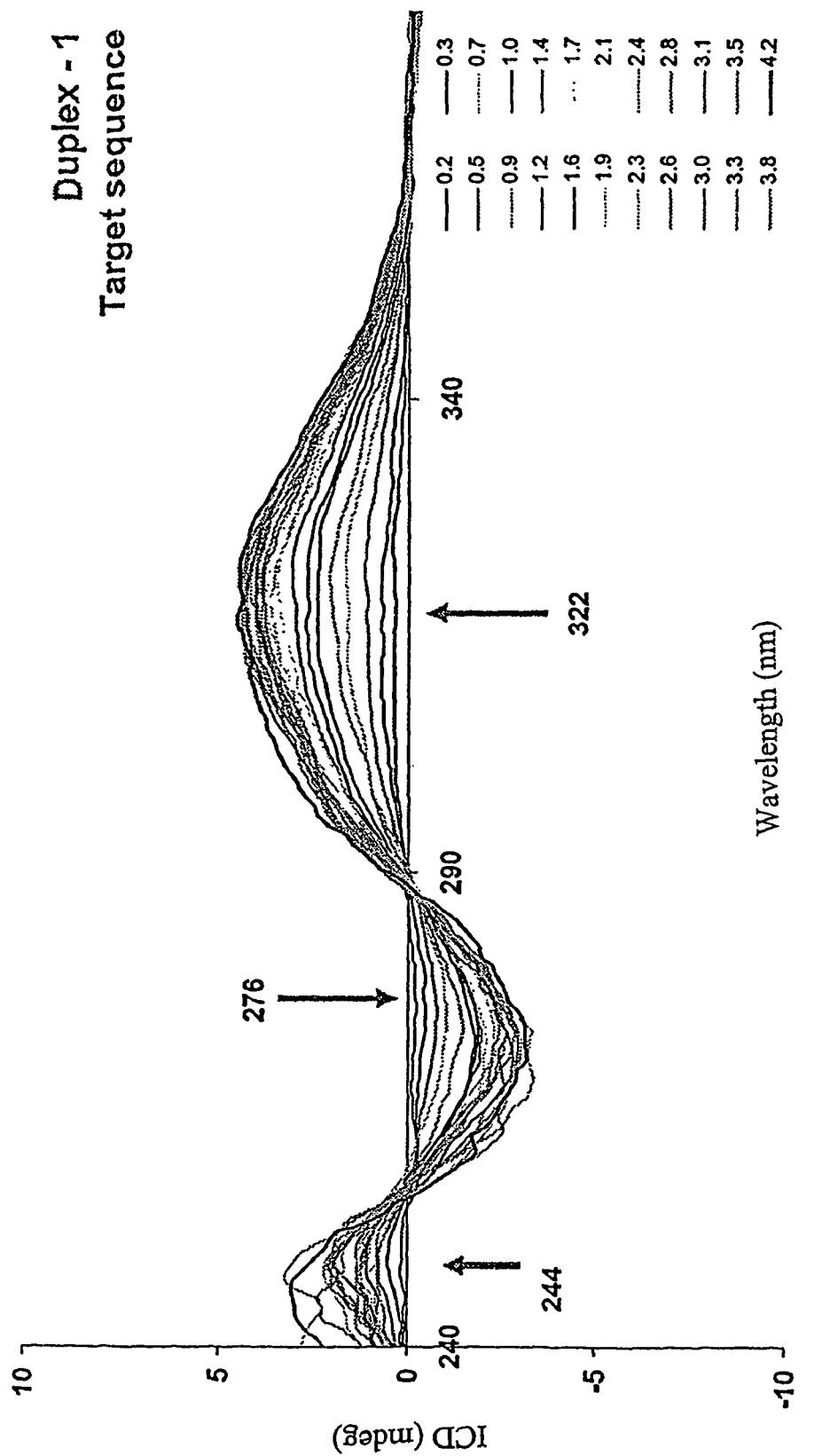
Figure 3(b)(ii)

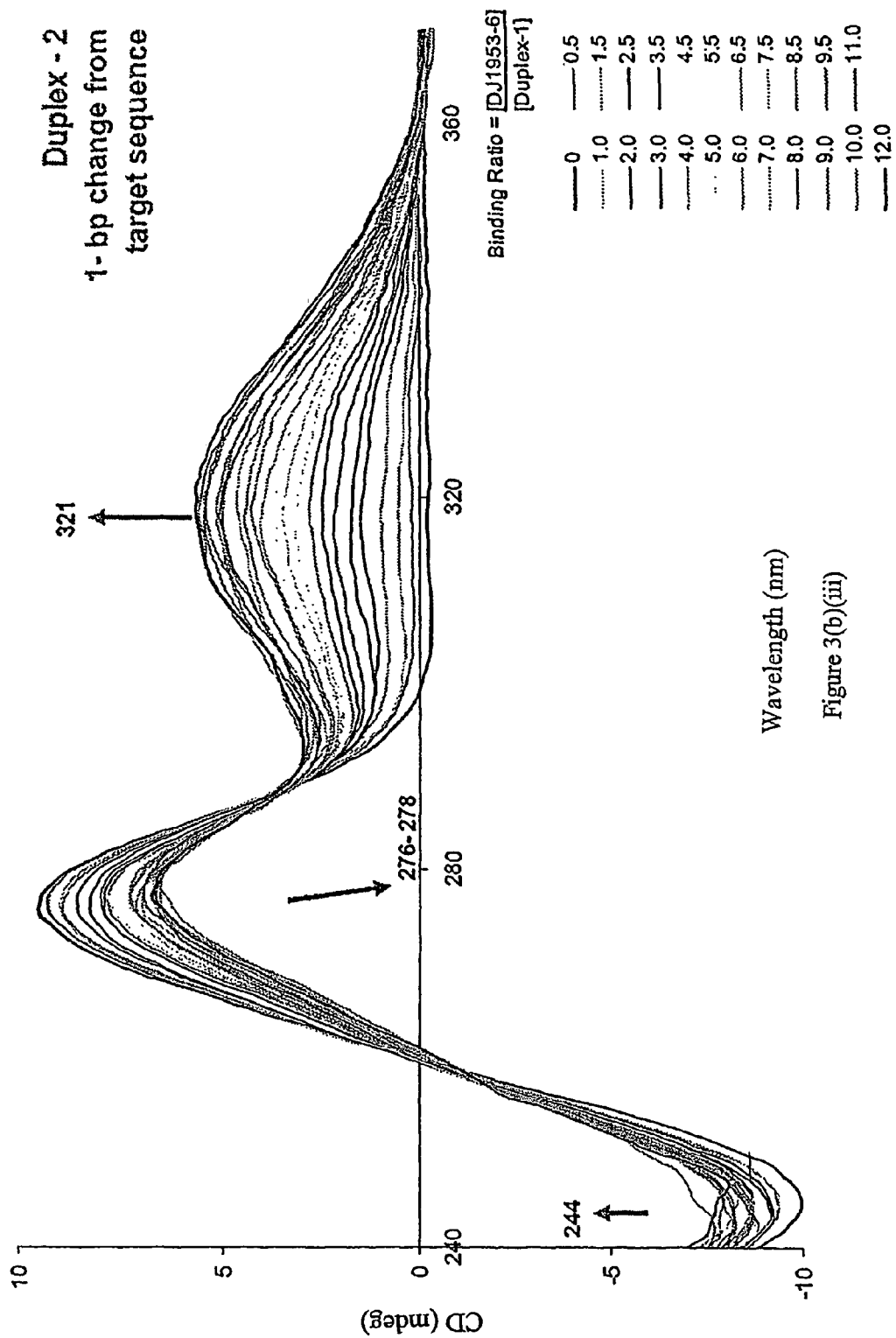
Figure 3(b)(iii)

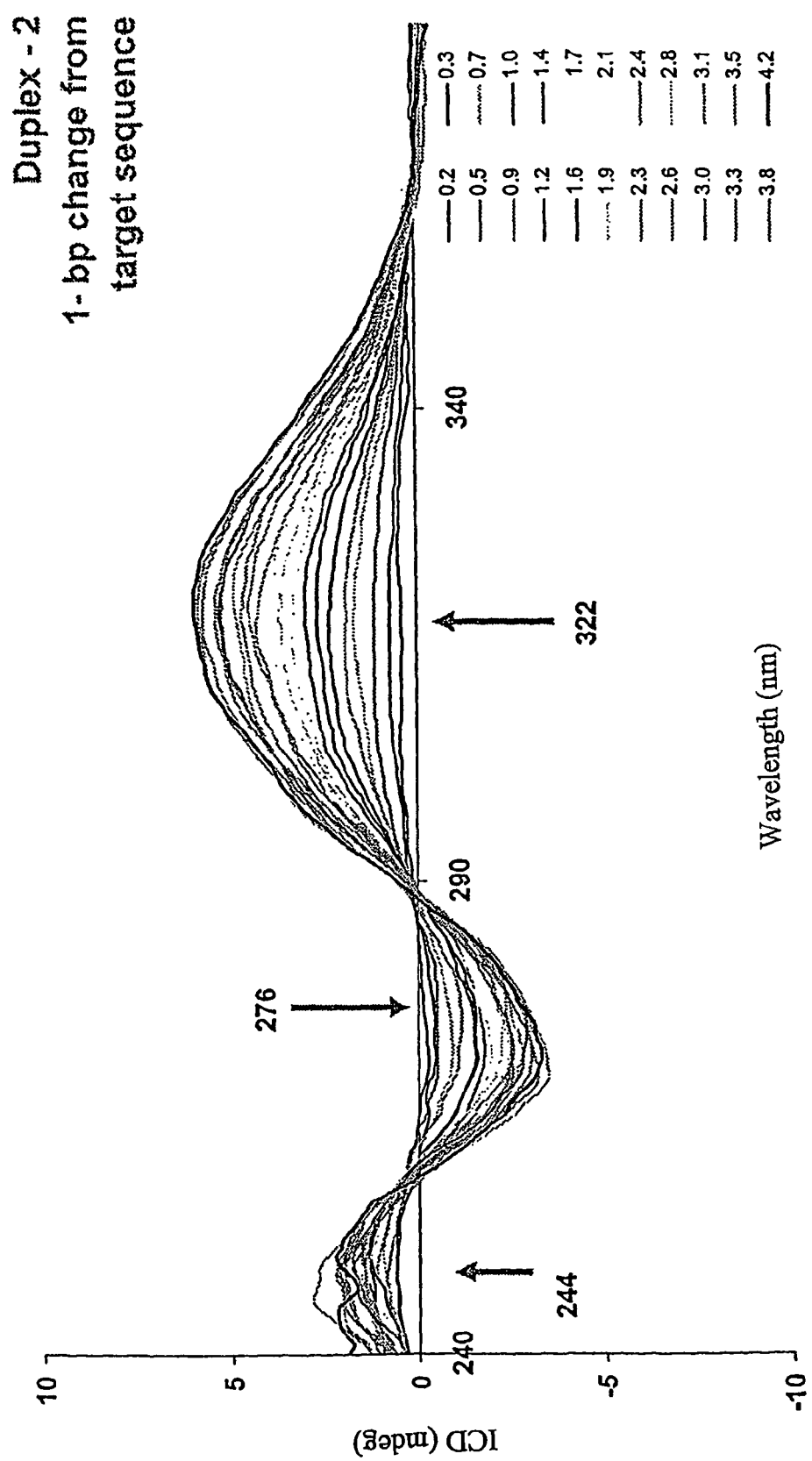
Figure 3(b)(iv)

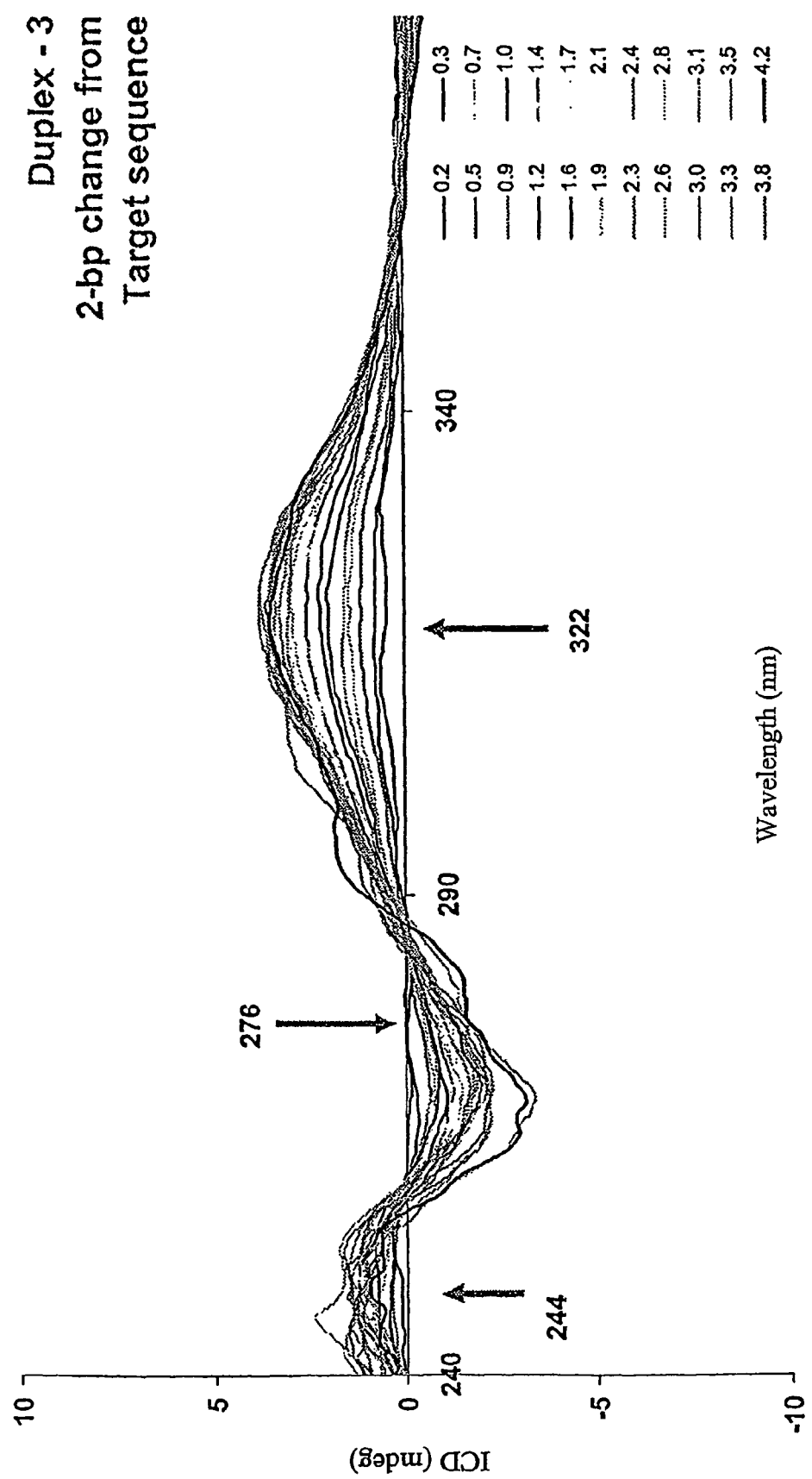
Figure 3(b)(vi)

SEQUENCE SELECTIVE PYRROLE AND IMIDAZOLE POLYAMIDE METALLOCOMPLEXES

CROSS REFERENCE TO RELATED APPLICATIONS

This disclosure is filed under 35 U.S.C. §371 and claims priority to International Application Serial No. PCT/AU2004/001368, filed Oct. 7, 2004, which claims priority under 35 U.S.C. §119 to Australian application serial no. 2003905512, filed Oct. 7, 2003, the disclosures of which are incorporated herein by reference.

TECHNICAL FIELD

The present invention relates to sequence selective compounds for targeting therapeutic or diagnostic groups to polynucleotides. More particularly, the present invention relates to sequence selective targeting of metallocomplexes, such as metallodrugs and metallodiagnostics, to polynucleotides.

BACKGROUND OF THE INVENTION

Cisplatin is a metallo anticancer drug which stops replication within cells by binding irreversibly to nitrogen (N7), of guanine (G) and adenine (A), and forming intrastrand and interstrand cross-links in the major groove of DNA. However, cisplatin binds indiscriminately and also binds with macromolecules other than DNA. This indiscriminate binding can lead to adverse effects in healthy cells. Cisplatin is currently used to treat a range of cancers including testicular, ovarian, bladder, head and neck, lung and cervical cancers. However, a drawback of cisplatin is that many human cancer cell lines have a natural resistance to cisplatin, and those that can be treated may later develop resistance to the drug. In addition, treatment with cisplatin may produce severe side effects in patients, including nephrotoxicity, neurotoxicity, ototoxicity, impairment of sex hormone production and psychosexual difficulties as well as nausea and hair loss. Second generation platinum drugs (such as carboplatin, ZD0473, oxaliplatin) have been developed, however, like cisplatin, they can cause indiscriminate, irreversible damage and disadvantageously may have similar negative side effect profiles.

Farrell, et al, *Inorg Chem.*, 38, (1999), 3535 describe metallodrugs based on cisplatin but having two or three platinum centres linked by an alkyl chain. These compounds have been shown to cross the cell membrane and bind to DNA and are active in some cisplatin resistant cell lines. However, like cisplatin, these compounds are not sequence specific.

Brabec and co-workers (*Biochemistry*, 2000, 39, 12639-12649; *Eur. J. Biochem.* 1999, 266) have prepared compounds in which cisplatin is attached to the minor groove binding molecule, distamycin. However, whilst distamycin has an affinity for sequences in the minor groove, it is not sequence selective. Moreover, in those compounds the coupling of the platinum moiety to the very end of the distamycin restricts the binding interaction of both groups and neither the distamycin nor the platinum are in a position to optimise their binding interaction.

The present invention relates to compounds in which a metallo complex, such as a metallodrug or metallo-diagnostic compound, is attached to a sequence selective polyamide(s) as a means of selectively targeting the metallo complex to a particular sequence of interest.

SUMMARY OF THE INVENTION

According to a first aspect of the invention there is provided a compound of formula (1)

$$[M^1-T^1]_a-[P^1-T^2-M^2]_b-[T^3-P^2]_c \quad (1)$$

or a salt thereof,
wherein
$M^1$ and $M^2$ are the same or different and are each a metal coordination complex, wherein at least one of $M^1$ and $M^2$ is capable of interacting with a major groove or minor groove of a polynucleotide;
$P^1$ and $P^2$ are the same or different and are each a pyrrole-imidazole polyamide;
$T^1$, $T^2$ and $T^3$ are the same or different and are each a linker group;
a is 0, or 1
b is an integer selected from 1, 2, 3, 4 and 5; wherein when b is an integer greater than 1, each $P^1$, each $T^2$ and each $M^2$ may be the same or different; and
c is 0, 1 or 2; wherein when c is 2, each $P^2$ may be the same or different and each $T^3$ may be the same or different.

In one embodiment a=0, b=1, and c=0. In another embodiment, a=0, b=1, and c=1. In a further embodiment a=1, b=1, and c=0. In another embodiment a is 0, b is 1 and c is 2.

$M^1$ and $M^2$ may be the same or different and are individually selected from a platinum complex, a palladium complex, a ruthenium complex, and a rhodium complex. At least one of $M^1$ and $M^2$ may interact with a major groove or a minor groove of a polynucleotide. For example, $M^1$ and/or $M^2$ may bind to a nucleotide base. In one embodiment, $M^1$ and/or $M^2$ may bind irreversibly to a nucleotide base. In another embodiment, at least one of $M^1$ and $M^2$ may intercalate within a minor or a major groove of a polynucleotide. In one embodiment, an aromatic moiety of $M^1$ and/or $M^2$ may intercalate between base pairs of a minor or a major groove of a polynucleotide.

The pyrrole-imidazole polyamide ($P^1$, $P^2$) independently comprise a plurality of heterocyclic rings selected from the group consisting of optionally substituted Im (where "Im" is N-methylimidazole), optionally substituted Py (where "Py" is N-methylpyrrole) and optionally substituted Hp (where "Hp" is 3-hydroxy N-methylpyrrole). The heterocyclic rings in respective pyrrole-imidazole polyamides may be the same or different and may be arranged in any order. The number of heterocyclic moieties in each pyrrole-imidazole-polyamide may be from 2 to 10. In one embodiment a pyrrole-imidazole polyamide may comprise 3 heterocyclic rings. In another embodiment, a pyrrole-imidazole polyamide may comprise 4 heterocyclic rings. Respective heterocyclic rings in a pyrrole-imidazole polyamide may be connected by amide radicals, for example, alkylamido, such as acetamido, radicals. At least one heterocyclic ring (e.g., a heterocyclic ring at the end of a pyrrole-imidazole-polyamide) may be covalently bound to a linker group.

The choice and combination of Im, Py and Hp groups in the respective polyamide chains of compounds of formulae (1) determine sequence selectivity of the compound. The value of a and b controls the overall charge of the compound.

The linker groups ($T^1$, $T^2$, $T^3$) may comprise at least one functional group capable of coordinating to a metal ion such as Pt, Pd, Ru or Rh. The linker groups ($T^1$, $T^2$, $T^3$) may comprise at least one functional group suitable for allowing the linker group to be covalently bound to a pyrrole-imidazole-polyamide.

In one embodiment the linker group has the formula (2):

$$-Y^1-(A)_n-Y^2- \quad (2)$$

wherein
$Y^1$ and $Y^2$ may be the same or different and are independently selected from NH, $-NH_2$, C=O, C=S, C=NH, O, OH, S, SH, S(O), $S(O)_2$, $NR^3$, $NHR^3$, $N(R^3)_2$, an optionally substituted cycloalkylamine, an optionally substituted cycloalkyldiamine, and an optionally substituted heteroaryl group (e.g., an optionally substituted N-heteroaryl group such as pyridyl, phenanthrolinyl, 2,2'-bipyridyl); where each $R^3$ is independently selected from alkyl, cycloalkyl, aryl or heteroaryl;

A is selected from an optionally substituted $C_{1-10}$ alkylene, an optionally substituted $C_{2-10}$ alkenylene, an optionally substituted $C_{2-10}$ alkynylene, an optionally substituted $C_{3-6}$ cycloalkylene, an optionally substituted $C_{6-10}$ aryl, C=O, C=S, and C=NH, NH, O, S, $NH_2$, OH, SH, S(O), $S(O)_2$, amino acids, and spermidine; and n is an integer selected from 1 to 20, wherein when n is an integer greater than 1, each (A) group may be the same or different.

In one embodiment of a linker of formula (2) according to the present invention, one of $Y^1$ and $Y^2$ comprises a group capable of coordinating to a metal ion, and the other of $Y^1$ and $Y^2$ comprises a group which forms a covalent bond with a heterocyclic ring of a pyrrole-imidazole-polyamide.

In another embodiment, one of $Y^1$ and $Y^2$ may bond to a metallocomplex. For example, one of $Y^1$ and $Y^2$ may form a covalent bond with a ligand coordinated to a metal ion of a metallocomplex. Alternatively, one of $Y^1$ and $Y^2$ may function as a ligand and coordinate to a metal ion of a metallocomplex.

In another embodiment of formula (1) wherein c=2, in linker $T^3$ $Y^1$ may form a covalent bond with a heterocyclic ring of a pyrrole-imidazole polyamide and $Y^2$ may form a covalent bond with a heterocyclic ring of a pyrrole-imidazole polyamide.

In one embodiment the linker group may have the formula (2a)

$$—NH-(A)_n-NH_2— \quad (2a)$$

where A and n are as defined above, and where the $—NH_2$ moiety is capable of coordinating to a metal ion, such as Pt, Pd, Ru, Rh; and the —NH— group is covalently bound to a heterocyclic ring of a pyrrole-imidazole polyamide.

For example, in one embodiment when A is alkylene, the linker group may be an alkylenediamine radical "—NH—$(CH_2)_n$—$NH_2$—", where n is an integer from 1 to 20. In another embodiment, each A independently may be alkylene or O and the linker group may comprise —NH—$CH_2CH_2CH_2$—O—$CH_2CH_2$—O—$CH_2CH_2$—O—$CH_2CH_2CH_2$—$NH_2$. In a further embodiment, the linker may comprise at least one carbonyl group, e.g, the linker group may be —NH—C(O)—$CH_2CH_2$—NH—C(O)—$CH_2CH_2CH_2NH_2$—.

In alternative embodiments, the linker may comprise —S—$(CH_2)_n$—O—$(CH_2)_n$—S—, or —NH—$(CH_2)_n$—O—, where n is an integer from 1 to 20. In other embodiments, the linker may comprise one or more amino acid residues, eg, —C(O)—NH—$CH_2$—C(O)—NH—CH($CH_2SH$)—C(O)—NH—.

According to a second aspect of the invention there is provided a compound of formula (3):

$$\begin{bmatrix} [M^1—T^1]_a—P^1 \\ \phantom{xxx}\searrow \\ \phantom{xxxxx}T^4—T^5 \\ \phantom{xxx}\nearrow \\ [M^2—T^2]_b—P^2 \end{bmatrix}_m —M^3 \quad (3)$$

where $M^1$, $M^2$, $M^3$ are the same or different and are each a metal coordination complex as defined above for $M^1$ and $M^2$ of formula (1), wherein at least one of $M^1$, $M^2$ and $M^3$ is capable of interacting with a major groove or minor groove of a polynucleotide;

$P^1$ and $P^2$ are the same or different and are each a pyrrole-imidazole polyamide as defined above for formula (1);

$T^1$ and $T^2$ are the same or different and are each a linker group of formula (2) as defined above for formula (1);

$T^5$ is a linker group of formula (2) as defined above for $T^1$ and $T^2$ of formula (1), wherein one of $Y^1$ and $Y^2$ is bound to a metallocomplex $M^3$ and the other of $Y^1$ and $Y^2$ is covalently bound to $T^4$;

$T^4$ is a linker group of formula (2) as defined above for $T^1$ and $T^2$ of formula (1), wherein $Y^1$ is covalently bound to a pyrrole-imidazole polyamide, $Y^2$ is covalently bound to a pyrrole-imidazole polyamide, and wherein one $Y^1$, $Y^2$ and A is covalently bound to $T^5$;

a and b are independently selected from 0 and 1; and m is 1, 2, 3 or 4.

In one embodiment, $T^4$ is covalently bound to $T^5$ via A.

In one embodiment, m is 1. In another embodiment, m is 2.

In one embodiment of the second aspect of the invention a=0, b=1, m=1. In another embodiment, a=1, b=0, and m=1. In another embodiment a=1, b=1, and m=1. In another embodiment a=0, b=1, and m=2. In another embodiment a=1, b=0, and m=2. In a further embodiment, a and b are not both 1. At least one of $M^1$, $M^2$ and $M^3$ may bind covalently to a major groove or a minor groove of a polynucleotide. For example, at least one of $M^1$, $M^2$ and $M^3$ may bind covalently to a major groove of a polynucleotide such as DNA. $M^1$, $M^2$ and $M^3$ may be the same or different and are independently selected from Pt, Pd, Ru and Rh metallocomplexes. In one embodiment, $M^1$, $M^2$ and $M^3$ are independently selected from Pt and Ru metallocomplexes.

The choice and combination of Im, Py and Hp groups in the respective polyamide chains of compounds of formulae (3) determine sequence selectivity of the compound. The value of a, b and m controls the overall charge of the compound.

$T^4$ may be any suitable group capable of connecting two pyrrole-imidazole polyamides. In one embodiment $T^4$ is connected to two pyrrole-imidazole polyamides and a linker group $T^5$. $T^4$ may comprise one or more alkyl amido residues. For example, $T^4$ may comprise wherein n is an integer from 1 to 10, e.g., 1, 2, 3, 4, 5, 6, 7, 8, 9 or 10, and each (CRR') is independently an optionally substituted alkylene;

wherein in one (CRR'), R' is absent and CR is covalently boned to $T^5$.

Also disclosed herein are compounds of formula (4)

$$[P^1]_e\text{-}[T^1\text{-}P^2]_f\text{-}[T^2]_g \quad (4)$$

or a salt thereof, wherein

P¹ and P² are the same or different and are each a pyrrole-imidazole polyamide as defined above for formula (1);

T¹ and T² are the same or different and are each a linker group as defined above for formula (1);

e is 0 or 1;

f is an integer selected from 1, 2, and 3; wherein when f is an integer greater than 1, each T¹ and each P² may be the same or different; and g is 0 or 1.

Compounds of formula (4) may be substituted with at least one other group, such as a therapeutic group, a diagnostic agent, a metal coordination complex, or a fluorophore.

According to a third aspect of the invention there is provided a compound of formula (5):

$$[P^1]_e\text{-}[T^1\text{-}P^2]_f\text{-}[T^2]_g\text{-}M^1 \quad (5)$$

or a salt thereof, wherein

P¹ and P² are the same or different and are each a pyrrole-imidazole polyamide as defined above for formula (1);

T¹ and T² are the same or different and are each a linker group as defined above for formula (1);

e is 0 or 1;

f is an integer selected from 1, 2, and 3; wherein when f is an integer greater than 1, each T¹ and each P² may be the same or different;

g is 0 or 1; and

M¹ is a metal coordination complex capable of interacting with a major groove or minor groove of a polynucleotide as defined above for formula (1).

In accordance with a fourth aspect of the invention there is provided a process for preparing compounds of formula (1), or formula (5) comprising reacting a compound of formula (4) with a metal coordination complex to produce a compound of formula (1), or formula (5).

In accordance with a fifth aspect of the invention there is provided a process for preparing a compound of formula (3) comprising the steps of reacting a suitably functionalised pyrrole-imidazole polyamide with a suitably functionalised linker to produce a compound "P¹-T⁴"; reacting compound "P¹-T⁴" with a suitably functionalised pyrrole-imidazole polyamide "P²" to produce a compound "P¹-T⁴-P²"; reacting the compound "P¹-T⁴-P²" with a suitably functionalised linker "T⁵" to produce a compound "P¹-T⁴(-T⁵)-P²" reacting the compound "P¹-T⁴(-T⁵)-P²", with a suitable metal coordination complex to produce a compound "P¹-T⁴(-T⁵−M³)-P²" to produce a compound of formula (3).

In one embodiment of the fourth or fifth aspect of the invention, pyrrole-imidazole polyamides bound to a linker compound may be concatenated before reacting with a metal coordination complex.

In accordance with a sixth aspect of the invention there is provided a pharmaceutical composition comprising at least one compound of formula (1) according to the first aspect of the invention together with a pharmaceutically acceptable diluent, adjuvant or carrier.

In accordance with a seventh aspect of the invention there is provided a pharmaceutical composition comprising at least one compound of formula (3) according to the second aspect of the invention together with a pharmaceutically acceptable diluent, adjuvant or carrier.

In accordance with an eighth aspect of the invention there is provided a pharmaceutical composition comprising at least one compound of formula (5) according to the third aspect of the invention together with a pharmaceutically acceptable diluent, adjuvant or carrier.

In accordance with a ninth aspect of the invention there is provided a method of targeting a therapeutic agent(s) and/or a reporter group(s) to a sequence in a polynucleotide comprising contacting biological material suspected of containing said sequence with a compound of formula (1), formula (3) or formula (5).

In one embodiment of the ninth aspect of the invention, the method comprises contacting the biological material in vivo. In another embodiment of the ninth aspect of the invention, the method comprises obtaining a sample of biological material from an organism and contacting said sample with a compound of formula (1), formula (3), or formula (5) in vitro.

In accordance with a tenth aspect of the invention there is provided a method of treating a disease comprising administering to a mammal in need of such treatment a therapeutically effective amount of at least one compound according to the first, second or third aspect of the invention or a pharmaceutical composition according to the fifth, sixth or seventh aspect of the invention.

With reference to the tenth aspect of the invention, in one embodiment the disease may be a proliferative disease, such as cancer. In an alternative embodiment, the disease may be a viral disease, such as HIV. In another embodiment, the disease may be hepatitis, eg, hepatitis C.

In accordance with an eleventh aspect of the invention there is provided a method of diagnosis comprising contacting a biological sample with a diagnostically effective amount of at least one compound of the first, second or third aspect of the invention or a salt thereof, or a pharmaceutical composition according to the sixth, seventh or eighth aspect of the invention. In one embodiment the method comprises contacting said biological sample in vivo, for example, by administering to a mammal a diagnostically effective amount of said compound or composition. In another embodiment the method comprises obtaining a biological sample from said mammal and contacting said sample with a diagnostically effective amount of said compound or composition in vitro.

DEFINITIONS

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In the context of this invention, the term "metal coordination complex", "metal complex" and "metallocomplex" are synonymous and refer to a complex comprising a metal ion coordinated to one or more ligands and should be understood to mean that there are sufficient ligands or donor groups about the coordinating metal sufficient to complete the coordination sphere. Ligands coordinating the metal may be monodentate, or multidentate such as bidentate, tridentate, or tetradentate, as appropriate. Suitable ligands for a specific metal are known generally to those skilled in the art. Ligands may be coordinated to a metal in any suitable configuration, for example, cis or trans isomers. The ligands coordinated to a metal ion may be (R), (S) isomers, and metal complexes may be Δ, or Λ isomers, as appropriate.

In the context of this specification the term "polynucleotide" includes double stranded DNA.

Cisplatin is cis-diamminedichloroplatinum(II).

Transplatin is trans-diamminedichloroplatinum(II).

In the context of this specification, the term "pyrrole-imidazole polyamide" means an organic compound comprising two or more heterocyclic groups selected from optionally substituted N-methylimidazole (abbreviated "Im"), optionally substituted N-methyl-pyrrole (abbreviated "Py"), and optionally substituted 3-hydroxy N-methylpyrrole (abbreviated "Hp"), wherein adjacent heterocyclic groups are linked by a group comprising an amide bond and wherein the heterocyclic groups may be arranged in any order.

As used herein, the term "alkyl group" includes within its meaning straight chain or branched chain saturated aliphatic groups having from 1 to 20 carbon atoms, eg, 1, 2, 3, 4, 5, 6, 7, 8, 9, 10, 11, 12, 13, 14, 15, 16, 17, 18, 19 or 20 carbon atoms; or cyclic saturated aliphatic groups (also referred to herein as "cycloalkyl" groups) having from 3 to 10 carbon atoms, eg, 3, 4, 5, 6, 7, 8, 9, or 10 carbon atoms. For example, the term alkyl includes, but is not limited to, methyl, ethyl, 1-propyl, isopropyl, 1-butyl, 2-butyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, undecyl, dodecyl, tridecyl, cyclopropyl, 2-methylcyclopropyl, cyclobutyl, cyclopentyl, 2-methylcyclopentyl, 3-methylcyclopentyl, cyclohexyl, and the like.

The term "alkenyl group" includes within its meaning straight or branched chain unsaturated aliphatic hydrocarbon groups having from 2 to 20 carbon atoms, eg, 2, 3, 4, 5, 6, 7, 8, 9, 10, 11, 12, 13, 14, 15, 16, 17, 18, 19 or 20 carbon atoms, or cyclic unsaturated aliphatic hydrocarbon groups (also referred to herein as "cycloalkenyl" groups) having from 3 to 10 carbon atoms, and combinations thereof, having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butenyl, 1,3-butadienyl, 1-pentenyl, 2-pentenyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 1-nonenyl, 1-decenyl, 1-undecenyl, 1-dodecenyl, 3-dodecenyl, 9-dodecenyl, 1-tridecenyl, cyclohexenyl, and the like.

The term "alkynyl group" as used herein includes within its meaning straight or branched chain unsaturated aliphatic hydrocarbon groups having from 2 to 20 carbon atoms and having at least one triple bond. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, 1-heptynyl, 2-heptynyl, 1-octynyl, 2-octynyl, 1-nonyl, 1-decynyl, 1-undecynyl, 1-dodecynyl, 1-tridecynyl, and the like.

The term "alkylene" as used herein, includes within its meaning divalent, saturated, straight chain hydrocarbon radicals.

The term "alkenylene" as used herein, includes within its meaning, divalent, straight chain hydrocarbon radicals having at least one double bond.

The term "alkynylene" as used herein, includes within its meaning, divalent, straight chain hydrocarbon radicals having at least one triple bond.

The term "heterocycloalkyl" as used herein, includes within its meaning monovalent, saturated, monocyclic, bicyclic, polycyclic or fused radicals having from 3 to 10 carbon atoms wherein 1 to 5 atoms are heteroatoms selected from O, N, NH, or S.

The term "heterocycloalkylene" as used herein, includes within its meaning divalent, saturated, monocyclic, bicyclic, polycyclic or fused polycyclic radicals having from 3 to 10 carbon atoms wherein 1 to 5 atoms are heteroatoms selected from O, N, NH, or S.

The term "heterocycloalkenyl" as used herein, includes within its meaning monovalent, saturated, monocyclic, bicyclic, polycyclic or fused polycyclic radicals having from 3 to 10 carbon atoms and having at least 1 double bond, wherein from 1 to 5 atoms are heteroatoms selected from O, N, NH or S.

The term "heterocycloalkenylene" as used herein, includes within its meaning divalent, saturated, monocyclic, bicyclic, polycyclic or fused polycyclic radicals having from 3 to 10 carbon atoms and having at least one double bond, wherein from 1 to 5 atoms are heteroatoms selected from O, N, NH, or S.

The term "halogen" or variants such as "halide" or "halo" as used herein refers to fluorine, chlorine, bromine and iodine.

The term "heteroatom" or variants such as "hetero-" as used herein refers to O, N, NH and S.

The term "alkoxy" as used herein refers to straight chain or branched alkyloxy groups. Examples include methoxy, ethoxy, n-propoxy, isopropoxy, tert-butoxy, and the like.

The term "amino" as used herein refers to groups of the form —NR$_a$R$_b$ wherein R$_a$ and R$_b$ are individually selected from the group including but not limited to hydrogen, optionally substituted alkyl, optionally substituted alkenyl, optionally substituted alkynyl, and optionally substituted aryl groups.

The term "aromatic group", or variants such as "aryl" as used herein refers to monovalent single, polynuclear, conjugated and fused residues of aromatic hydrocarbons having from 6 to 10 carbon atoms. Examples of such groups include phenyl, biphenyl, naphthyl, phenanthrenyl, and the like.

The term "arylene" as used herein, includes within its meaning divalent, single, polynuclear, conjugated and fused residues of aromatic hydrocarbons having from 6 to 10 carbon atoms.

The term "heteroaryl" as used herein, includes within its meaning monovalent, single, polynuclear, conjugated and fused aromatic radicals having 6 to 20 atoms wherein 1 to 6 atoms are heteroatoms selected from O, N, NH and S. Examples of such groups include pyridyl, 2,2'-bipyridyl, phenanthrolinyl, quinolinyl, and the like.

The term "heteroarylene" as used herein, includes within its meaning divalent, single, polynuclear, conjugated and fused aromatic radicals having 6 to 20 atoms wherein 1 to 6 atoms are heteroatoms selected from O, N and S.

The term "amino acid" as used herein includes α, β, and γ amino acids and includes (L) and (D) isomers. Examples of amino acid residues include glycinyl, alaninyl, valinyl, leucinyl, isoleucinyl, methioninyl, prolinyl, phenylalaninyl, tryptophanyl, serinyl, threoninyl, cysteinyl, tyrosinyl, asparaginyl, glutaminyl, aspartyl, glutamyl, lysinyl, argininyl and histidinyl. An amino acid group may also be substituted via its side chain, eg, via the —COOH substituent of asparatic acid or glutamic acid, or via the a —SH substituent of methionine or cysteine.

The term "optionally substituted" as used herein means the group to which this term refers may be unsubstituted, or may be substituted with one or more groups independently selected from alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, alkylheteroaryl, cyano, cyanate, isocyanate, —C(O)NH(alkyl), and —C(O)N(alkyl)$_2$.

In the context of this invention the term "administering" and variations of that term including "administer" and "administration", includes contacting, delivering or providing an agent compound or composition of the invention to an organism by any appropriate means.

In the context of this specification, the term "mammal" includes humans and individuals of any species of social, economic or research importance including but not limited to members of the genus ovine, bovine, equine, porcine, feline, canine, primates, rodents, murine, caprine, leporine, and avian.

In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the terms "therapeutically effective amount" and "diagnostically effective amount", include within their meaning a sufficient but non-toxic amount of a compound or composition of the invention to provide the desired therapeutic or diagnostic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

DETAILED DESCRIPTION OF THE INVENTION

Figure 1:
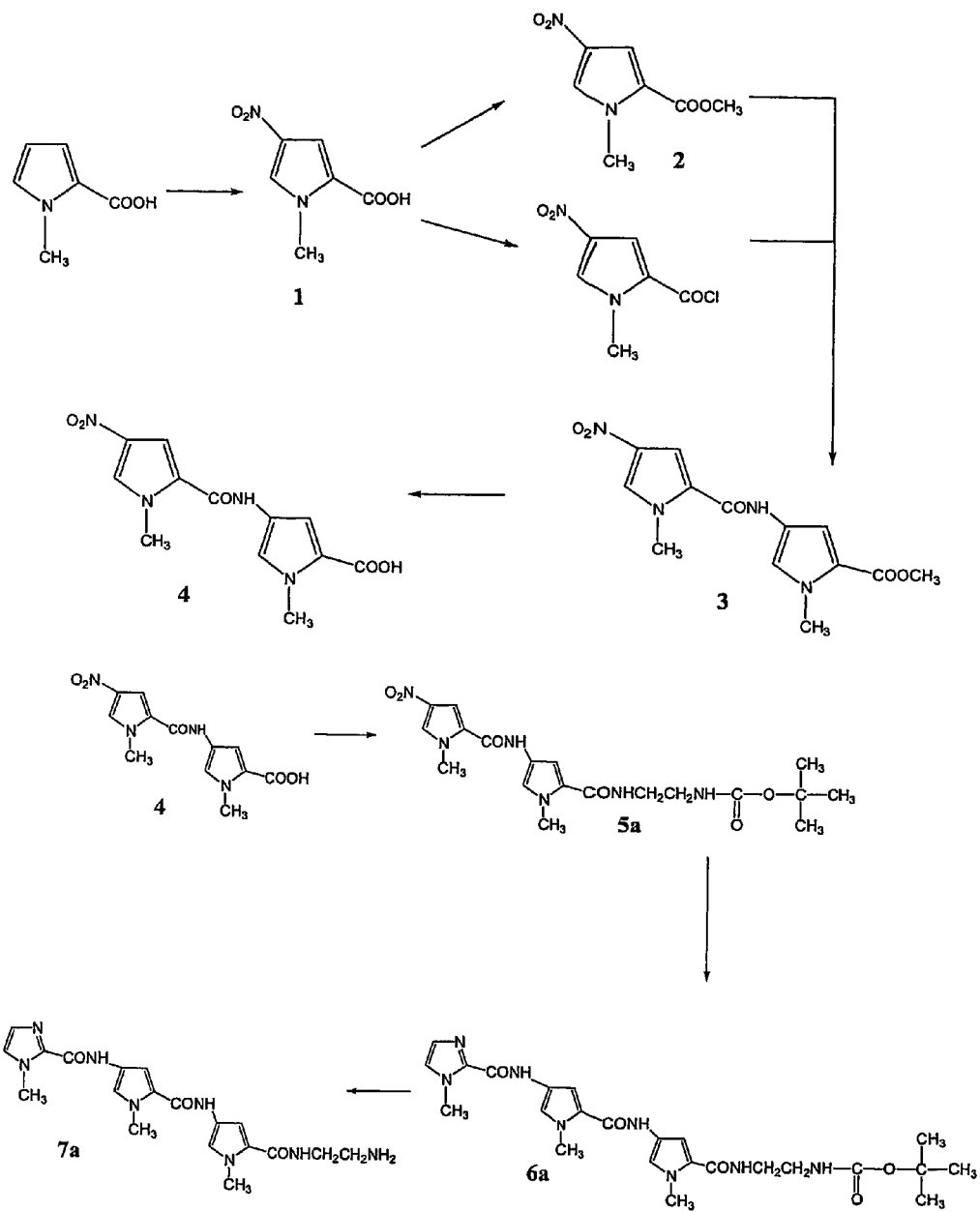
FIG. 1—Synthetic scheme illustrating preparation of compounds according to the invention.

The present invention relates to compounds comprising one or more sequence-specific polynucleotide-binding group(s) and one or more polynucleotide-binding metal complex(es). The metal complex(es) may be selected from platinum complexes (including but not limited to cisplatin, transplatin, carboplatin, oxaliplatin, ZD0473, Pt(dac)Cl$_2$, and the like), palladium complexes, ruthenium complexes, rhenium, rhodium complexes, etc). Compounds according to the present invention may be suitable for use as sequence specific metallodrugs or diagnostic agents. The interaction between the sequence specific pyrrole-imidazole polyamide component(s) of the compound and the DNA backbone may allow the metallocomplex component to be selectively targeted to a particular region of DNA. The metallocomplex may interact (e.g, bind or intercalate) with a minor or major groove of a polynucleotide such as DNA and thereby exert a therapeutic or diagnostic effect. The linker component(s) of compounds of the invention functions to connect the sequence selective pyrrole-imidazole polyamide component(s) to the metallocomplex component(s).

The present invention relates to compounds of formula (1):

or a salt thereof,
wherein
$M^1$ and $M^2$ are the same or different and are each a metal coordination complex, wherein at least one of $M^1$ and $M^2$ is capable of interacting with a major groove or minor groove of a polynucleotide;

$P^1$ and $P^2$ are the same or different and are each a pyrrole-imidazole polyamide;

$T^1$, $T^2$ and $T^3$ are the same or different and are each a linker group;

a is 0, or 1;

b is an integer selected from 1, 2, 3, 4 and 5; wherein when b is an integer greater than 1, each $P^1$, each $T^2$ and each $M^2$ may be the same or different; and c is 0, 1 or 2; wherein when c is 2, each $P^2$ may be the same or different and each $T^3$ may be the same or different.

In one embodiment of compounds of formula (1) a=0, b=1, and c=0. In another embodiment, a=0, b=1, and c=1. In a further embodiment a=1, b=1, and c=0.

An example of a compound of formula (1) is "trans-Im/Py/Py-[CONH(CH$_2$)$_6$—NH$_2$)Pt(NH$_3$)$_2$Cl" (which is also referred to herein as "DJ1953-6"):

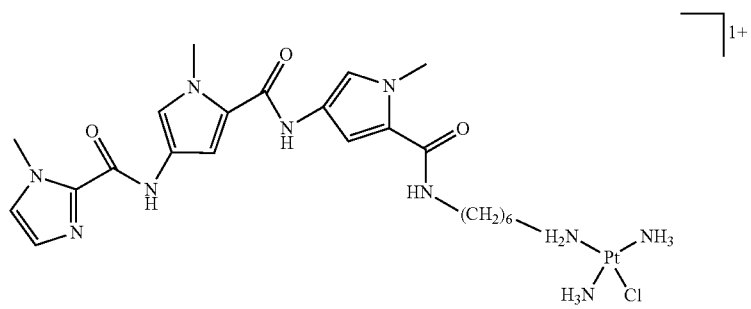

Another compound of formula (1) is "trans-Im/Py/Py-[CONH(CH$_2$)$_2$—NH$_2$)Pt(NH$_3$)$_2$Cl" (which is also referred to herein as "DJ1953-2"):

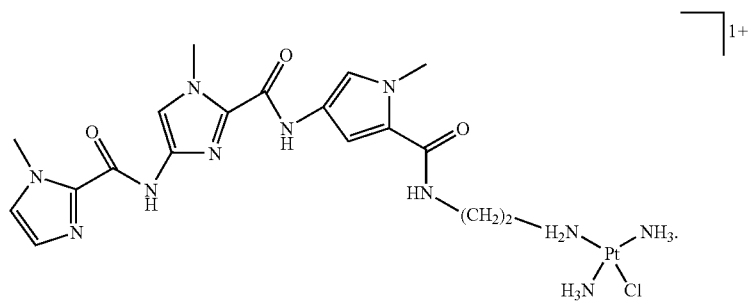

Further examples of compounds of formula (1) include:

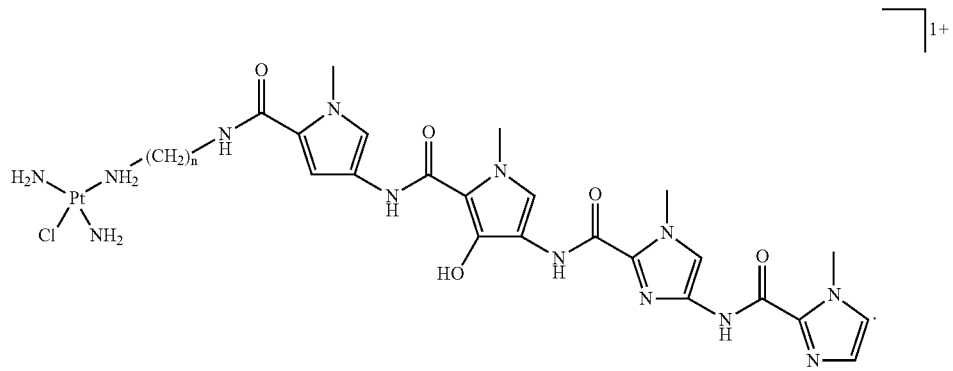

where n is an integer selected from 1, 2, 3, 4, 5, 6, 7, 8, 9 and 10.
In another embodiment a compound of formula (1) is "cis-Im/Py/Py-Pt":
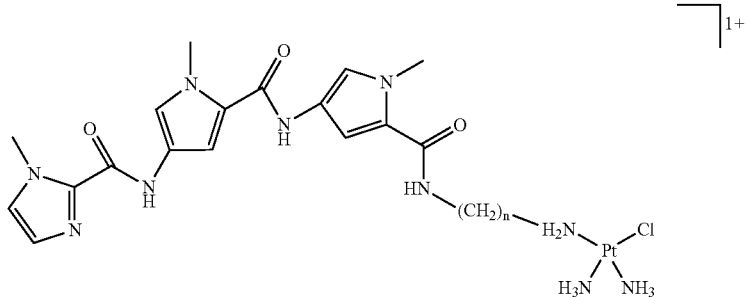
where n is an integer selected from 1, 2, 3, 4, 5, 6, 7, 8, 9 and 10, or a salt thereof.
Other examples of compounds of formula (1) include:
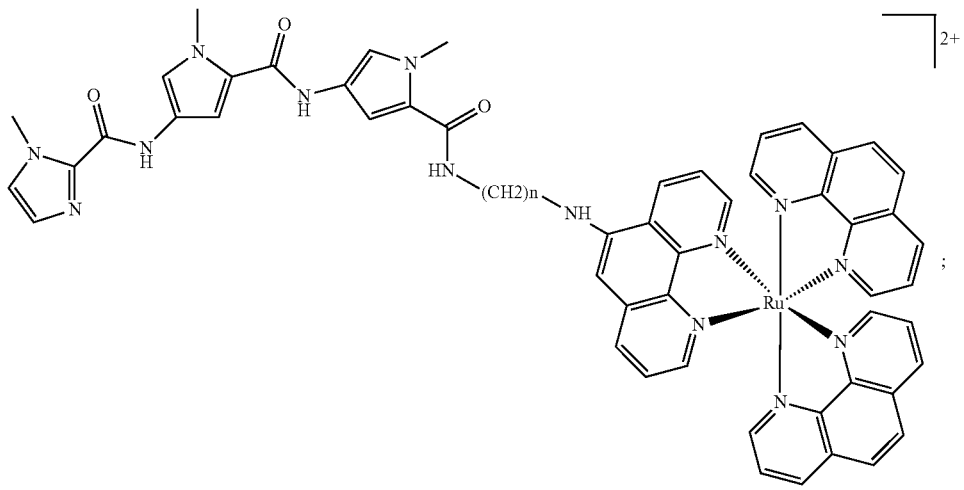
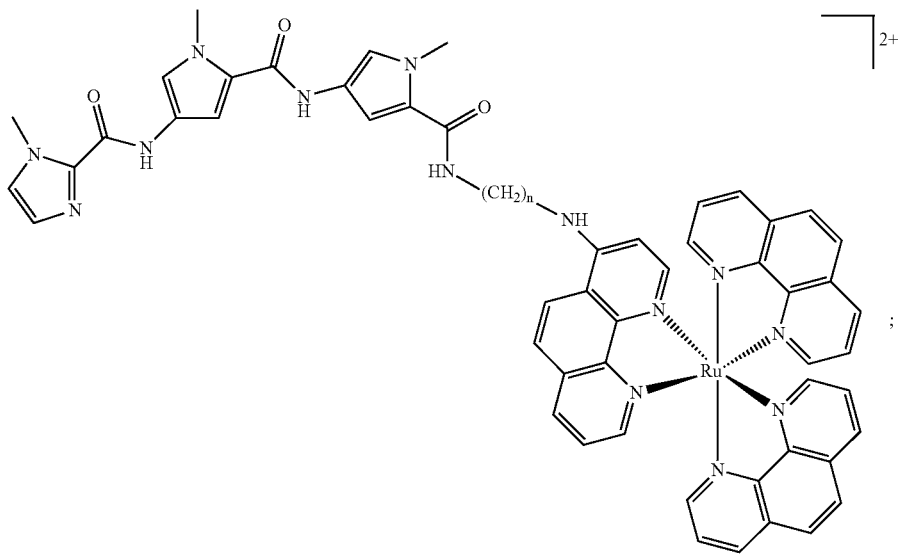

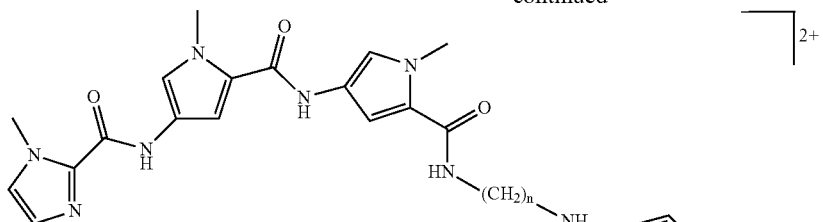
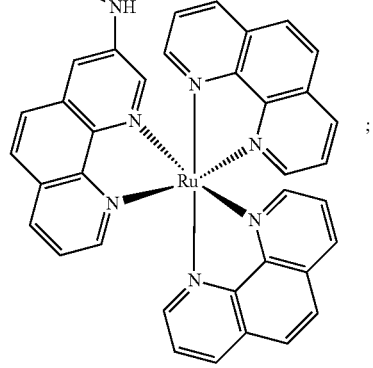
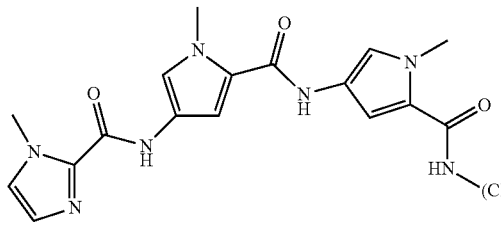
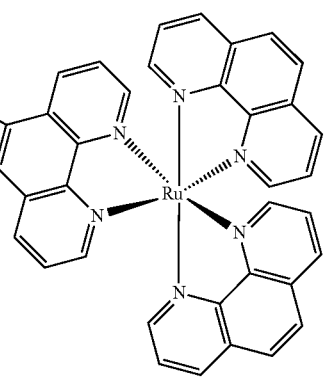
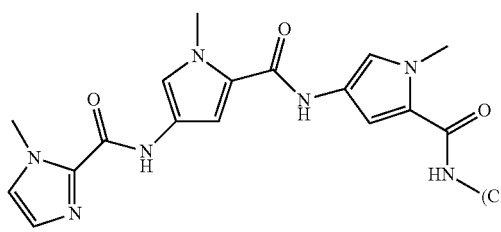
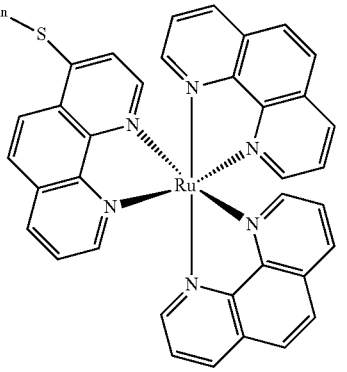

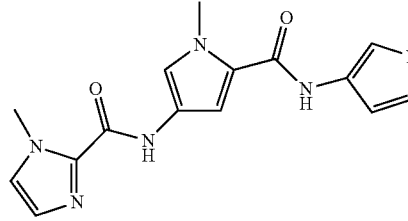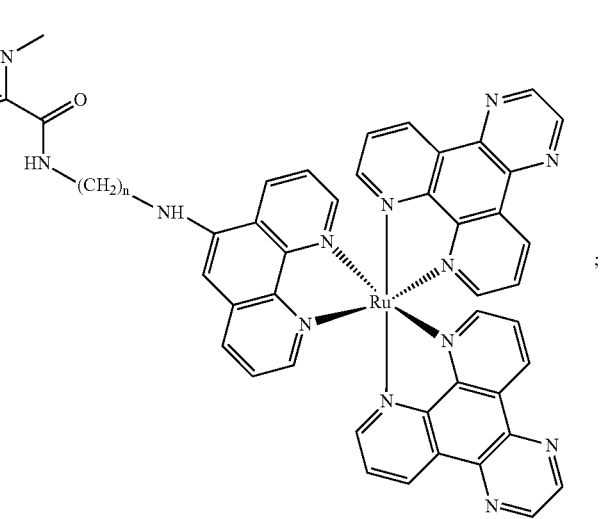
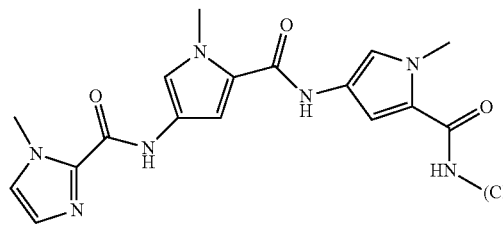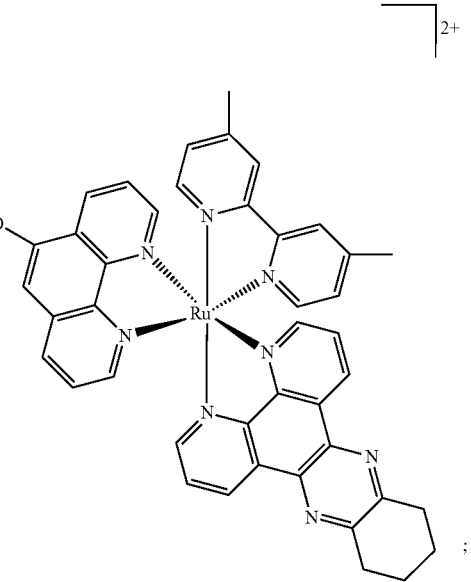

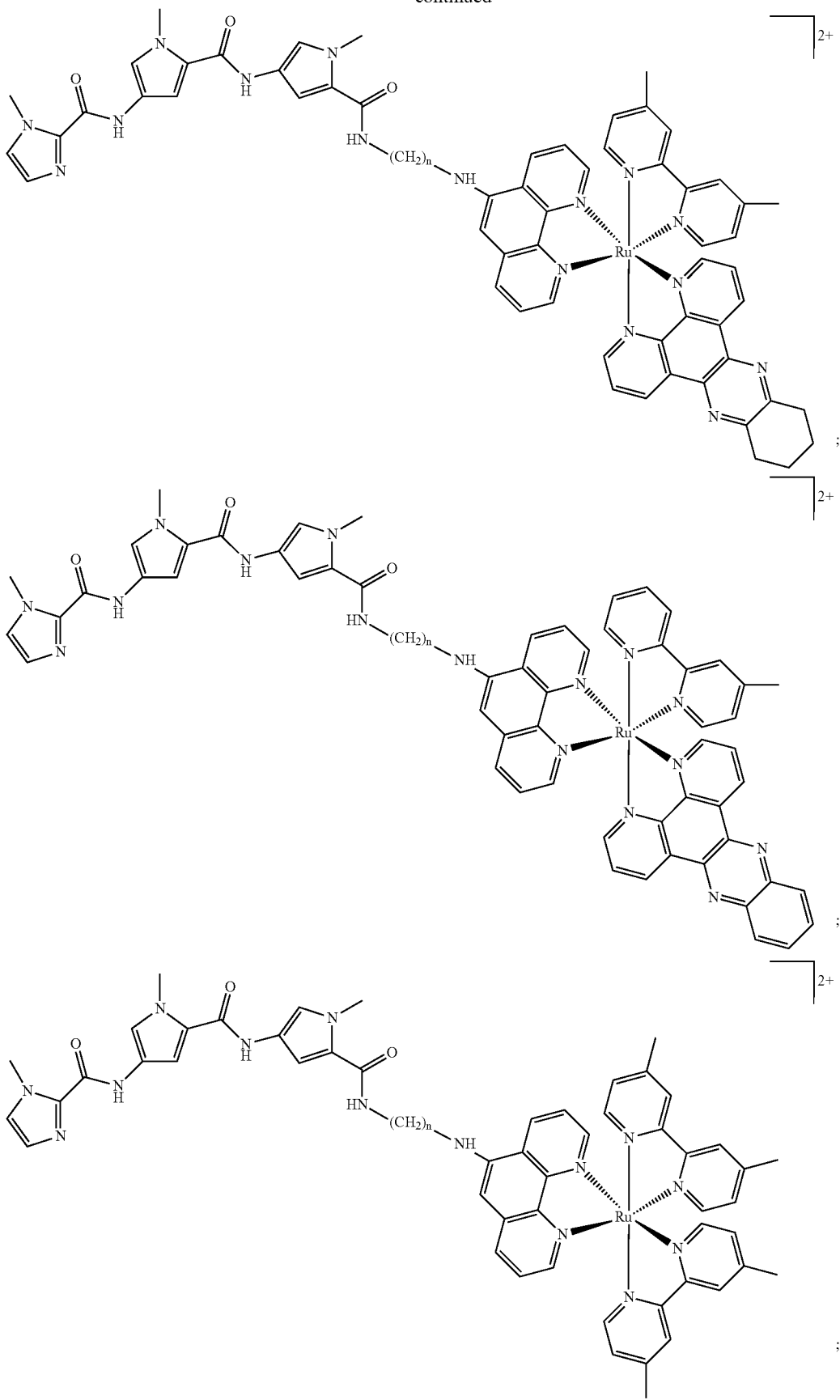

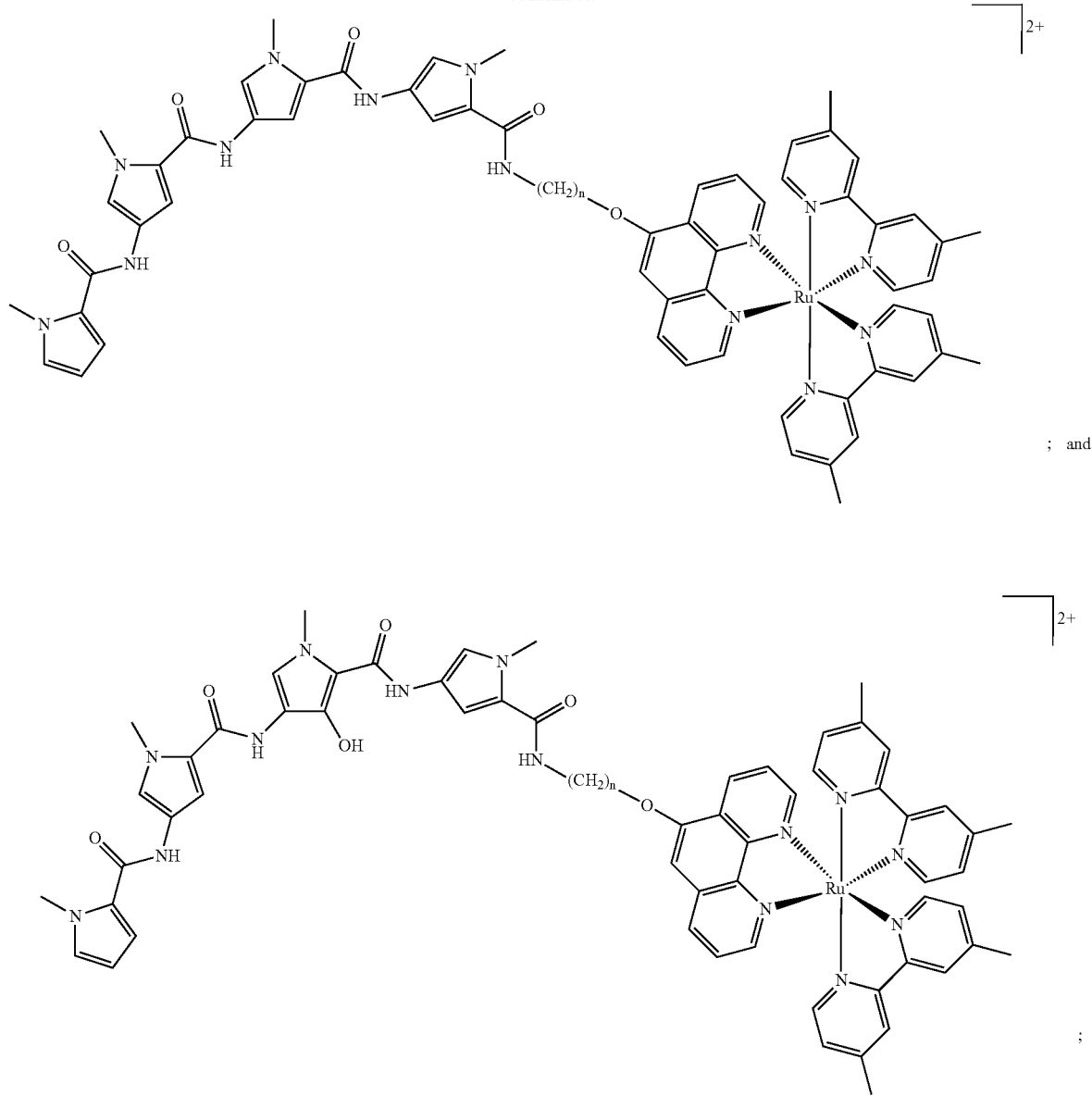
where n is an integer selected from 1, 2, 3, 4, 5, 6, 7, 8, 9 and 10, or a salt thereof.
Another embodiment of a compound of formula (1) is "trans-Im/Py/Py-Pt(NH$_3$)$_2$-Py/Py/Im":
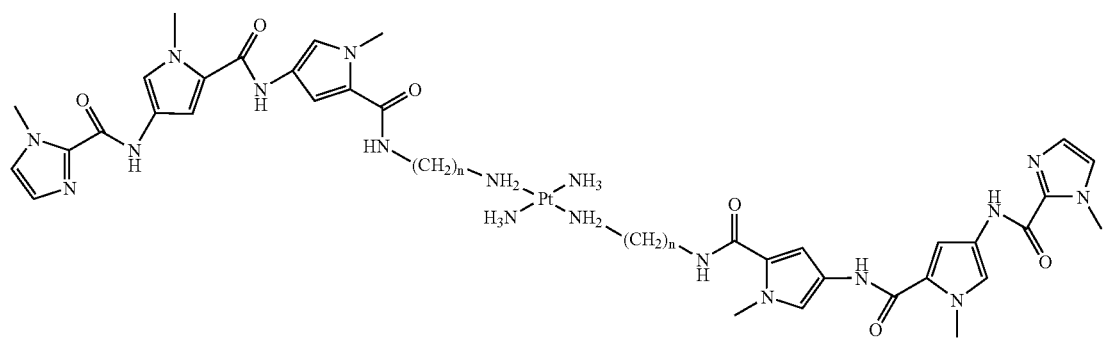

where each n is an integer independently selected from 1, 2, 3, 4, 5, 6, 7, 8, 9 and 10, or a salt thereof.

The present invention also relates to compounds of formula (3):

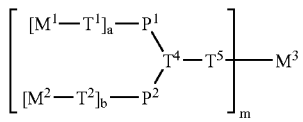

(3)

where $M^1$, $M^2$, $M^3$ are the same or different and are each a metal coordination complex as defined above for $M^1$ and $M^2$ of formula (1), wherein at least one of $M^1$, $M^2$ and $M^3$ is capable of interacting with a major groove or minor groove of a polynucleotide;

$P^1$ and $P^2$ are the same or different and are each a pyrrole-imidazole polyamide as defined above for formula (1);

$T^1$ and $T^2$ are the same or different and are each a linker group of formula (2) as defined above for formula (1);

$T^5$ is a linker group of formula (2) as defined above for $T^1$ and $T^2$ of formula (1), wherein one of $Y^1$ and $Y^2$ is bound to a metallocomplex $M^3$ and the other of $Y^1$ and $Y^2$ is covalently bound to $T^4$;

$T^4$ is a linker group of formula (2) as defined above for $T^1$ and $T^2$ of formula (1), wherein $Y^1$ is covalently bound to a pyrrole-imidazole polyamide, $Y^2$ is covalently bound to a pyrrole-imidazole polyamide, and wherein one $Y^1$, $Y^2$ and A is covalently bound to $T^5$;

a and b are independently selected from 0 and 1; and m is 1, 2, 3 or 4.

In one embodiment, $T^4$ is covalently bound to $T^5$ via A.

In one embodiment, m is 1. In another embodiment, m is 2.

In one embodiment of compounds of formula (3) a=0, b=1, m=1. In another embodiment, a=1, b=0, and m=1. In another embodiment a=1, b=1, and m=1. In another embodiment a=0, b=1, and m=2. In another embodiment a=1, b=0, and m=2. In a further embodiment, a and b are not both 1.

$T^4$ may be any suitable group capable of connecting two pyrrole-imidazole polyamides. In one embodiment $T^4$ is connected to two pyrrole-imidazole polyamides and a linker group $T^5$. $T^4$ may comprise one or more alkyl amido residues. For example, $T^4$ may comprise

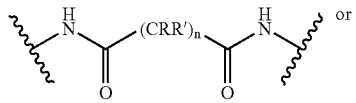

or

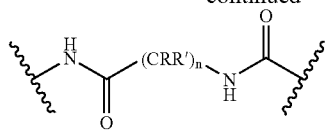

wherein n is an integer from 1 to 10, e.g., 1, 2, 3, 4, 5, 6, 7, 8, 9 or 10, and each (CRR') is independently an optionally substituted alkylene;

wherein in one (CRR'), R' is absent and the CR is covalently bonded to $T^5$

In alternative embodiments, $T^4$ may comprise an optionally substituted 'butyl' framework (which is covalently linked to two pyrrole-imidazole polyamides and $T^5$). In one embodiment, the butyl framework may be derived by condensing, e.g. 2,4-diaminobutyric acid, or 2-aminobutyric acid with a suitably functionalised pyrrole-imidazole polyamide(s) (e.g, a polyamide comprising an amino, carboxylic acid, ester or acid halide group).

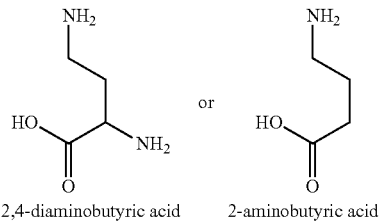

2,4-diaminobutyric acid    2-aminobutyric acid

In one embodiment, a heterocyclic ring of one pyrrole-imidazole polyamide may be functionalised with an amino group and a heterocyclic ring of a second pyrrole-imidazole polyamide may be functionalised with a carboxylic acid group (or alternatively an ester such as an activated ester or acid chloride), wherein the amino group and carboxylic derivative group, respectively, may be coupled with, e.g, 2,4-diaminobutyric acid, or 2-aminobutyric acid, to form amide bonds. Suitable amide coupling techniques are well known to those skilled in the art.

In one embodiment, the configuration of linker $T^4$ may produce a "hairpin bend" as shown schematically below for the compound "trans-[Im/Im/Im-γ-Py/Py/Py]Pt(NH$_3$)$_2$Cl". Such "hairpin bends" are sometimes abbreviated as "γ".

In one embodiment the compound of formula (3) may be "trans-[Im/Im/Im-γ-Py/Py/Py]Pt(NH$_3$)$_2$Cl":

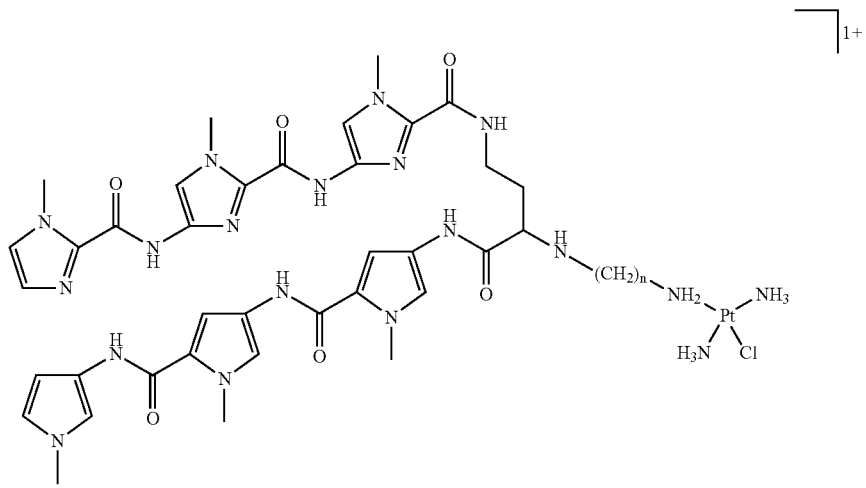

where n is an integer selected from 1, 2, 3, 4, 5, 6, 7 and 8, or a salt thereof.
In another embodiment the compound of formula (3) may be
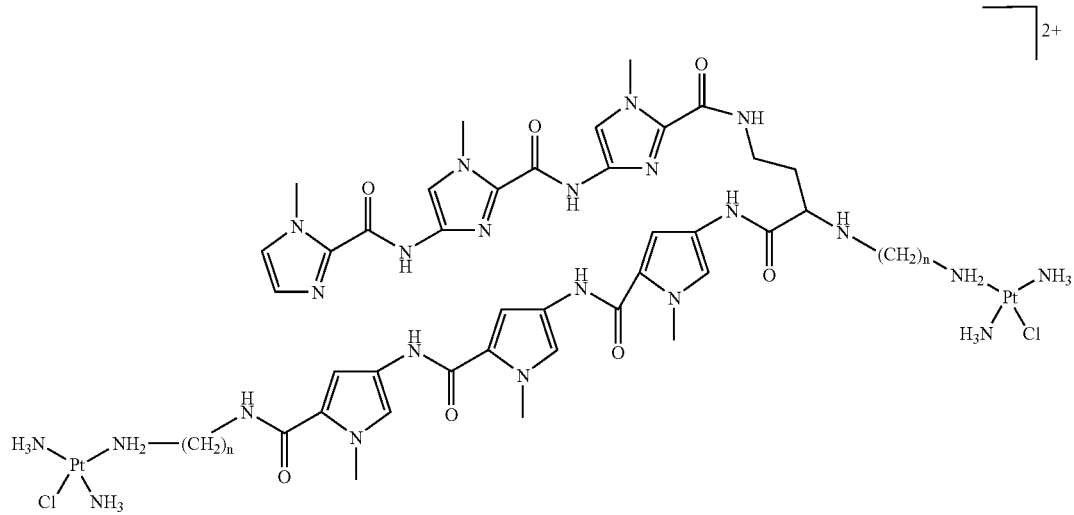
where n is an integer selected from 1, 2, 3, 4, 5, 6, 7 and 8, or a salt thereof.
In a further embodiment, the compound of formula (3) may be:
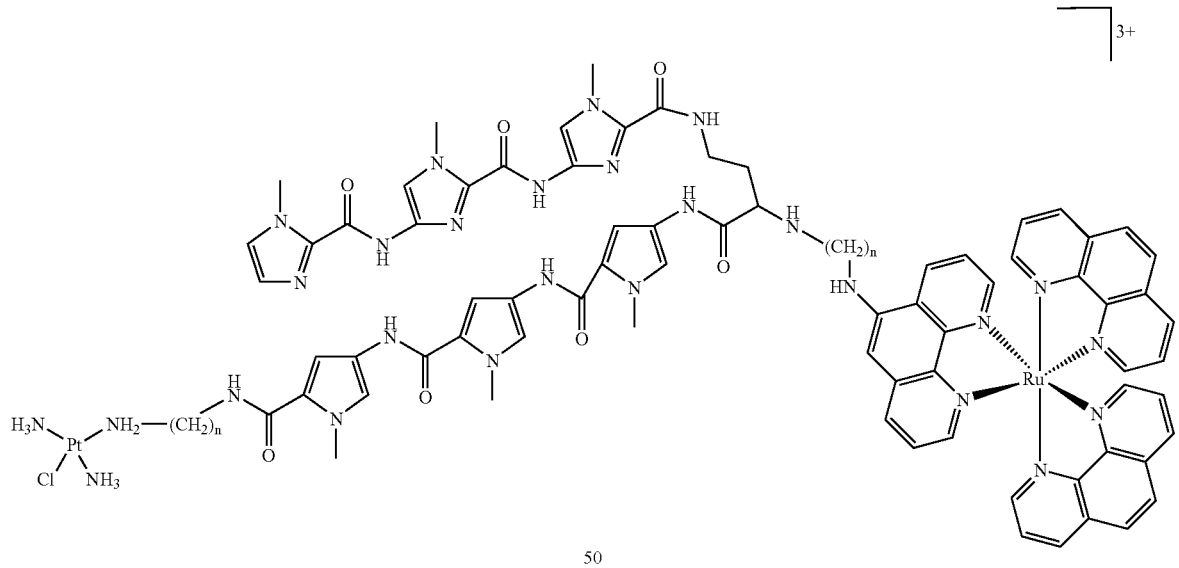
In another embodiment, the compound of formula (3) may be:
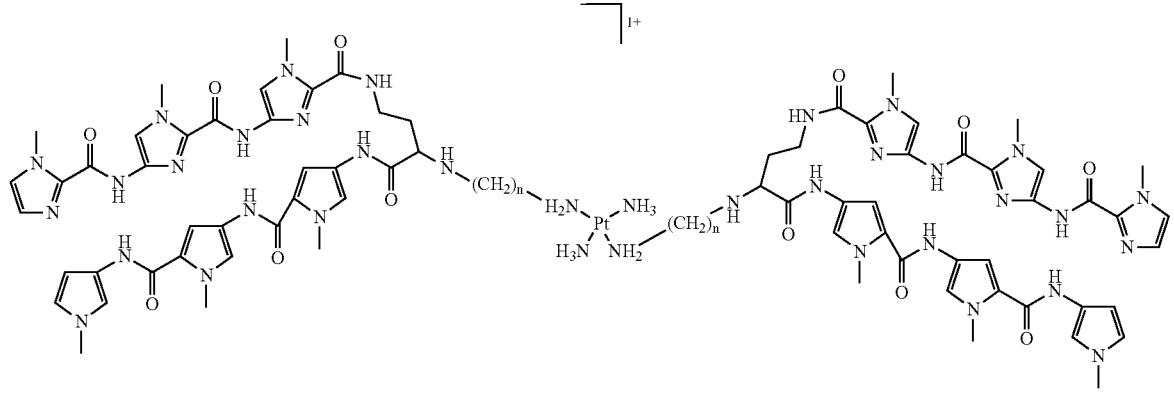

where n is an integer selected from 1, 2, 3, 4, 5, 6, 7 and 8, or a salt thereof.
In another embodiment the compound of formula (3) may be:
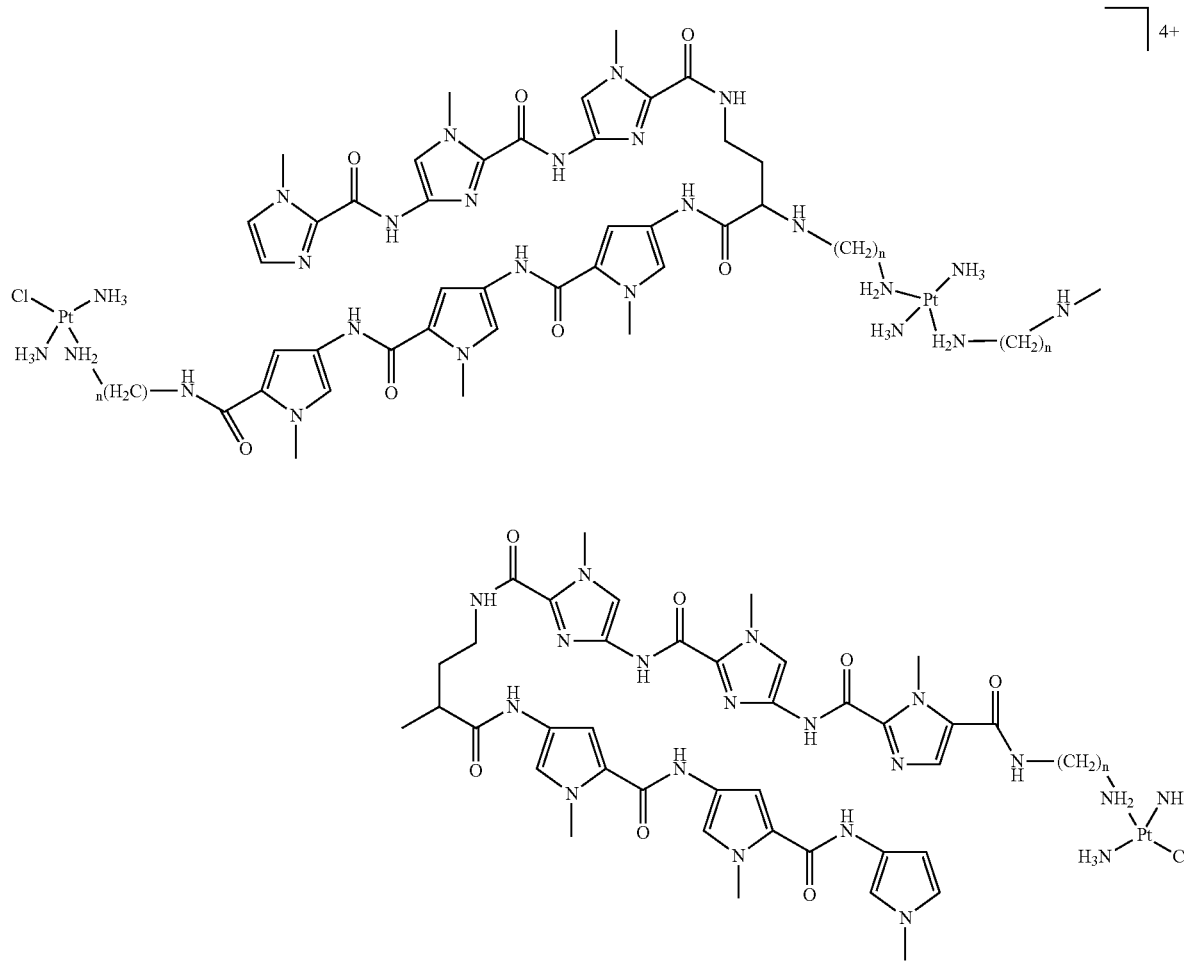
where n is an integer selected from 1, 2, 3, 4, 5, 6, 7 and 8, or a salt thereof.
In another embodiment of a compound of formula (3) is:
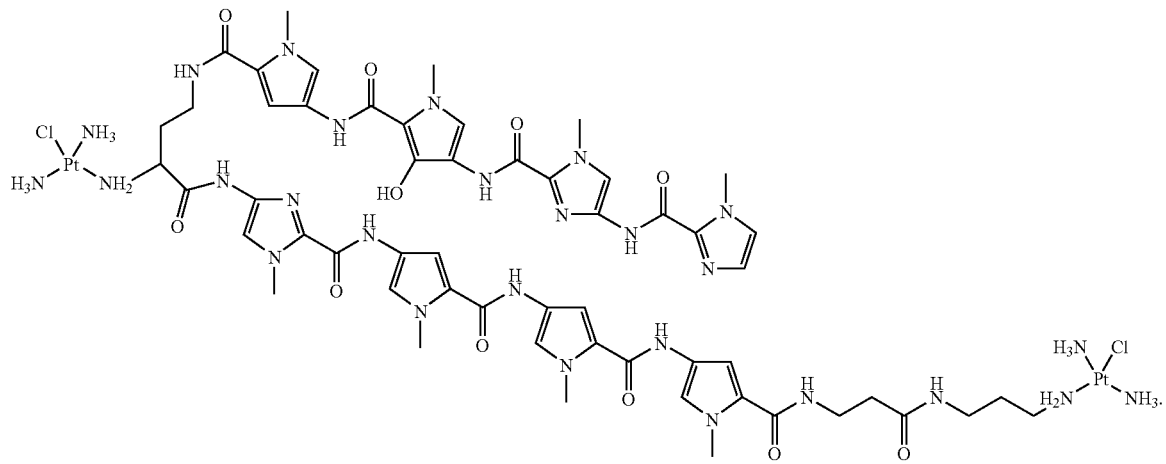

Also disclosed herein are compounds of formula (4):

$$[P^1]_e\text{-}[T^1\text{-}P^2]_f\text{-}[T^2]_g \quad (4)$$

or a salt thereof,
wherein
$P^1$ and $P^2$ are the same or different and are each a pyrrole-imidazole polyamide;
$T^1$ and $T^2$ are the same or different and are each a linker group;
e is 0 and 1;
f is an integer selected from 1, 2, and 3; wherein when f is an integer greater than 1, each $T^1$ and each $P^2$ may be the same or different; and
g is 0 or 1.
Compounds of formula (4) may be substituted with at least one other group, such as a therapeutic group, a diagnostic agent, a metal coordination complex, or a fluorophore.

The present invention also relates to compounds of formula (5):

$$[P^1]_e\text{-}[T^1\text{-}P^2]_f\text{-}[T^2]_g\text{-}M^1 \quad (5)$$

or a salt thereof,
wherein
$P^1$ and $P^2$ are the same or different and are each a pyrrole-imidazole polyamide;
$T^1$ and $T^2$ are the same or different and are each a linker group;
e is 0 or 1;
f is an integer selected from 1, 2, and 3; wherein when f is an integer greater than 1, each $T^1$ and each $P^2$ may be the same or different;
g is 0 or 1; and
$M^1$ is a metal coordination complex capable of interacting with a major groove or minor groove of a polynucleotide.
Examples of compounds of formula (5) include:

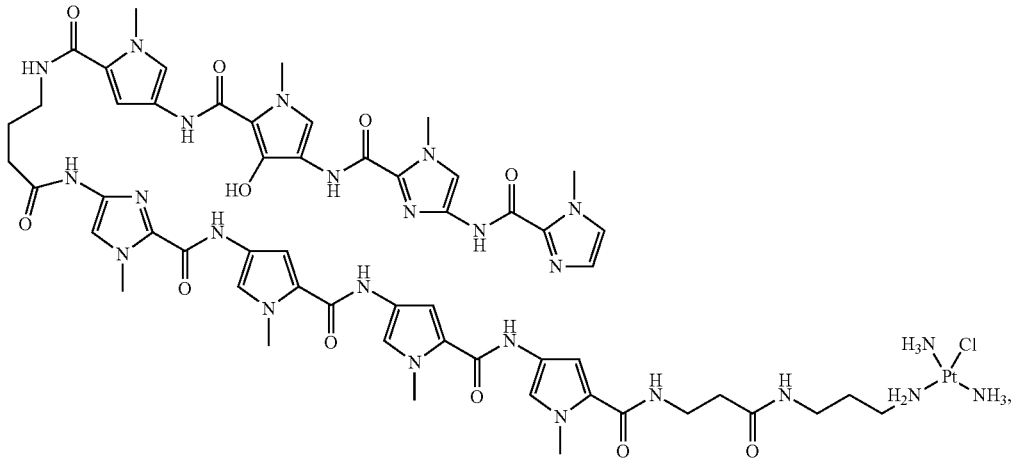

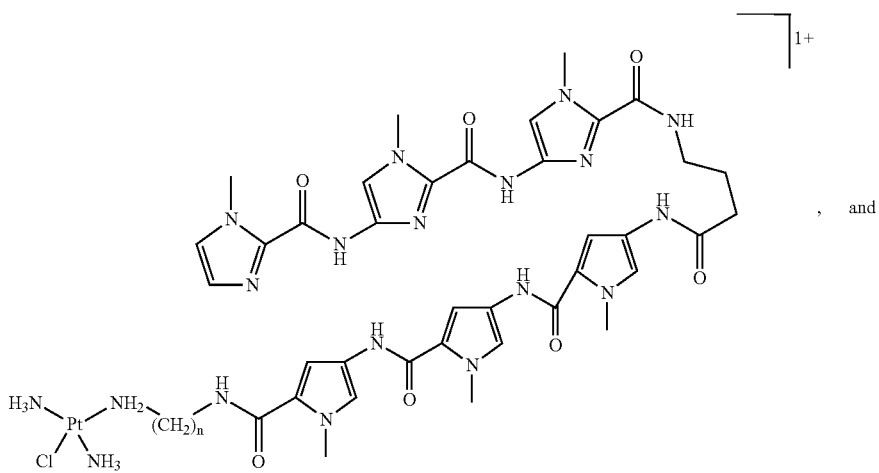

, and

-continued

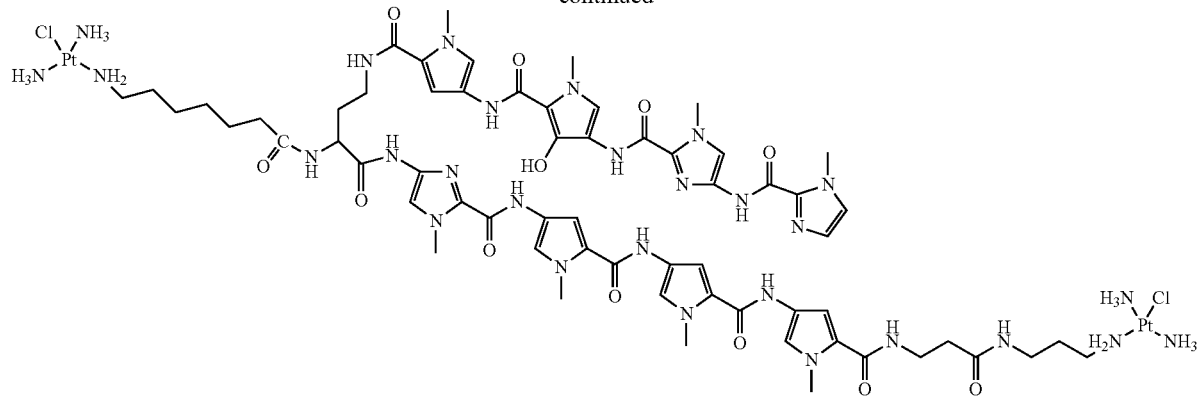

Compounds of formulae (1), (3), (4) and (5) above may be charged or uncharged. In some embodiments of the invention the compounds are charged.

With reference to formulae (1), (3) and (5) above, at least one of $M^1$, $M^2$ and $M^3$ is a metallocomplex which may interact with a major groove or a minor groove of a polynucleotide. For example, $M^1$, $M^2$ and/or $M^3$ may interact with a major or minor groove of a polynucleotide by bonding to a nucleotide base, or may intercalate between bases. In one embodiment at least one of $M^1$, $M^2$ and $M^3$ may bind to a major groove of a polynucleotide. For example, when at least one of $M^1$, $M^2$ and $M^3$ is a platinum complex (such as cisplatin, transplatin, carboplatin, ZD0473, oxaliplatin, Pt(dac)Cl$_2$, etc) the platinum ion may bind to nitrogen (e.g, N7) of guanine (G) or adenine (A). Alternatively, when one of $M^1$, $M^2$ and $M^3$ is a ruthenium complex comprising at least one ligand with an aromatic ring, the aromatic ring may intercalate with aromatic residues of base pairs.

The value of the integers a and b in formulae (1) and (5) and the value of the integers a, b and m in formula (3), controls the overall charge of respective compounds.

$M^1$, $M^2$ and $M^3$ May be any therapeutically or diagnostically active metallocomplex. For example, each of $M^1$, $M^2$ and $M^3$ may be the same or different and may independently be a platinum, palladium, ruthenium or rhodium complex. The metal ion may have any suitable oxidation state. For example, the metal ion may be Pd(II), Pt(II), Pt(IV), Ru(II), or Ru(III). In addition, metallocomplexes may be present in any suitable geometry.

At least one of $M^1$, $M^2$ and $M^3$ may be a therapeutic agent. The therapeutic agent may be a platinum complex. For example, the platinum complex may be of the general formula [Pt(diammine)L$_2$], where each L is a suitable monodentate ligand, or two L taken together is a suitable bidentate ligand. In this context, the term "diammine" may indicate two monodentate "ammine" ligands, or a bidentate "diammine" ligand. For example, the platinum complex may be of the type [Pt(diammine)Cl$_2$], such as:

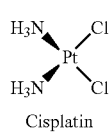
Cisplatin

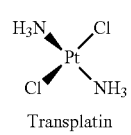
Transplatin

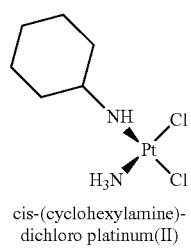
cis-(cyclohexylamine)-dichloro platinum(II)

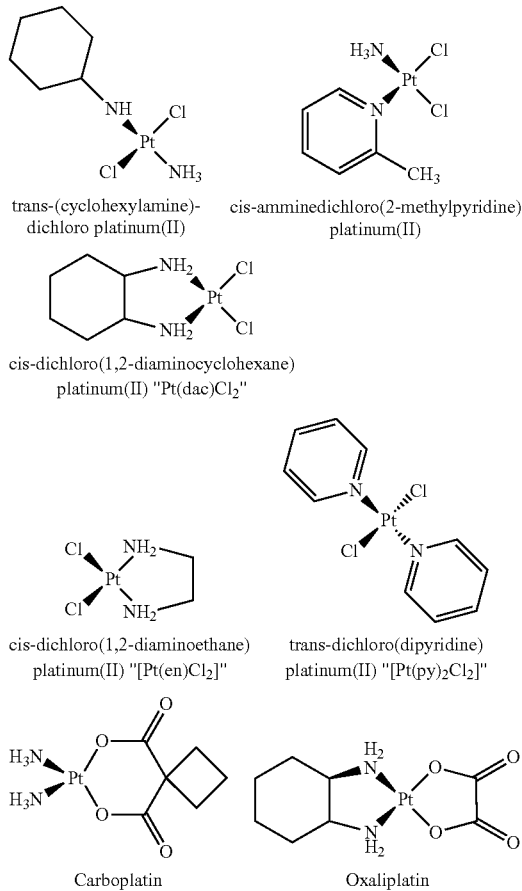

In alternative embodiments of the invention, at least one of $M^1$ and $M^2$ may be a reporter group. The reporter group may comprise a fluorescent group, or a group capable of becoming fluorescent upon binding, (e.g, intercalating) to a polynucleotide such as DNA. A reporter group may comprise a rhenium complex or a ruthenium complex. The ruthenium complex may be of the general formula [Ru(L-L)(L'-L')(L"-L")]$^{2+}$, where L-L, L'-L', and L"-L" may be the same or different and respectively may represent a bidentate ligand, or (L-L)(L'-L') together may be present a tetradentate ligand, or any one or more of L-L, L'-L', and L"-L" may represent two suitable monodentate ligands.

Examples of bidentate ligands include but are not limited to optionally substituted 2,2'-bipyridine, 5,5'-dimethyl-2,2'-bipyridine, 4,4'-dimethyl-2,2'-bipyridine, dipyrido[3,2-a:2'3'-c]phenazine, dipyrido[3,2-a:2',3'-c](6,7,8,9-tetrahydro)phenazine dipyrido[3,2-d:2'3'-f]quinoxaline, 9,10-phenanthrenenequinone diamine, 2,2':6',2''-terpyridine, 1,10-phenanthroline, 4,7-diamino-1,10-phenanthroline; 3,8-diamino-1,10-phenanthroline; 4,7-diethylenediamine-1,10-phenanthroline; 3,8-diethylenediamine-1,10-phenanthroline; 3,8-dinitro-1,10-phenanthroline; 4,7-diphenyl-1,10-phenanthroline; or 3,8-diphenyl-1,10-phenanthroline. The bidentate ligand may be a substituted 1,10-phenanthroline, such as an alkylated and/or halogenated phenanthrolinyl ligand, e.g, 4-methylphenanthroline, or 4-chlorophenanthroline, 1,10-phenanthroline-5,6-dione, 1,10-phenanthrolin-5-ylamine, 5-nitro-1,10-phenanthroline, 2-, 3-, 4- and 5-substituted and disubstituted phenanthrolines. Other examples of bidentate ligands include 2-, 3-, 4- and 5-substituted and disubstituted 2,2'-bipyridines, and optionally substituted 1,2-diaminocyclohexanes.

At least one of L-L, L'-L', and L''-L'', or (L-L)(L'-L') together, may comprise an intercalator group, a fluorescent group, or a group capable of becoming fluorescent upon binding to DNA. The intercalator group may also be one which fluoresces upon intercalating to DNA. Examples of fluorescent groups include dppz (dipyrido[3,2-a:2'3'-c]phenazine), dpqC (dipyrido[3,2-a:2',3'-c](6,7,8,9-tetrahydro)phenazine), and dpq (dipyrido[3,2-d:2'3'-f]quinoxaline).

With reference to formulae (1), (3), (4) and (5), the pyrrole-imidazole polyamide ($P^1$, $P^2$, $P^3$) independently comprise a plurality of heterocyclic rings selected from the group consisting of optionally substituted Im (where "Im" is N-methylimidazole), optionally substituted Py (where "Py" is N-methylpyrrole) and optionally substituted Hp (where "Hp" is 3-hydroxy N-methylpyrrole). Respective heterocyclic ring(s) may be optionally substituted with, for example, one or more groups such as halides, hydroxyl, amino, nitro, $C_{1-6}$ alkyl, $C_{2-6}$ alkenyl, and/or $C_{6-10}$ aryl groups. The heterocyclic rings in a pyrrole-imidazole polyamide may be the same or different and may be arranged in any order. Respective heterocyclic rings in a pyrrole-imidazole polyamide may be connected by radicals containing amide groups, for example, alkylamide radicals such as acetamido radicals. Examples of pyrrole-imidazole polyamides have been described in U.S. Pat. No. 6,472,537 to Baird and Dervan, entitled "Polyamides for binding in the minor groove of double stranded DNA"; and *Bioorganic and Medicinal Chemistry*, 9, (2001) 2215-2235, the entire contents of which are incorporated herein by cross-reference.

The number of heterocyclic rings in each pyrrole-imidazole-polyamide may be from 2 to 10. For example, the number of heterocyclic rings may be 2, 3, 4, 5, 6, 7, 8, 9 or 10. In one embodiment of the invention, the pyrrole-imidazole polyamide is a "trimer" comprising 3 heterocyclic rings. In another embodiment the pyrrole-imidazole polyamide is a "tetramer" comprising 4 heterocyclic rings. Respective heterocyclic rings may be the same or different and are independently from optionally substituted Im, optionally substituted Py and optionally substituted Hp, where the heterocyclic rings may be in any nominated order. The number and order of Im, Py and Hp groups in a pyrrole-imidazole polyamide may be chosen so as to produce a polyamide selective for a polynucleotide sequence of interest.

The choice and combination of Im, Py and Hp groups in the respective polyamide chains of compounds of formulae (1), (3), (4) and (5) determine sequence selectivity of the compound as described, for example in U.S. Pat. No. 6,472,537 to Baird and Dervan, entitled "Polyamides for binding in the minor groove of double stranded DNA". For example, the combination of polyamides Im/Im/Im and Py/Py/Py would be selective for a central core of 5'-CCC-3' in a polynucleotide. As another example, the combination of polyamides Hp/Py/Hp/Py and Py/Hp/Py/Hp would be selective for a core sequence of 5'-TATA-3'.

Some non-limiting examples of pyrrole-imidazole polyamides in accordance with the present invention include:

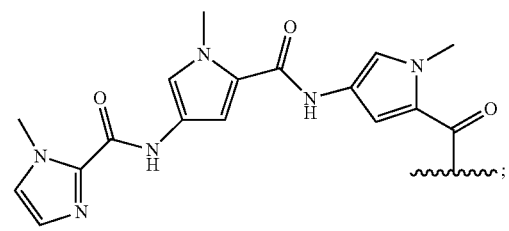

"Im/Py/Py"

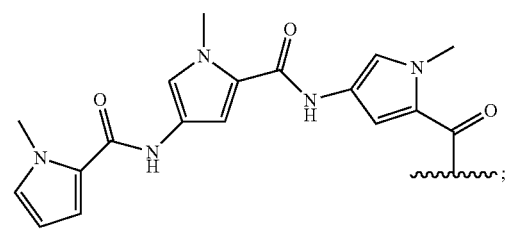

"Py/Py/Py"

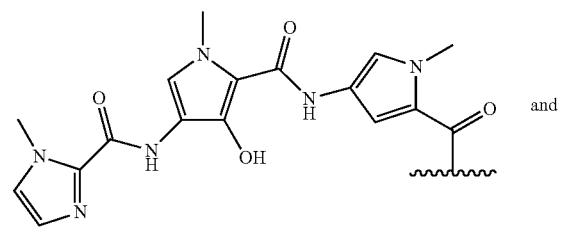

and

"Im/Hp/Py"

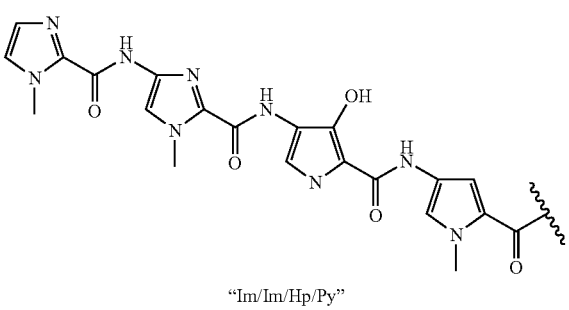

"Im/Im/Hp/Py"

In accordance with the present invention, the linker(s) operate to connect components of the compounds. For example, a linker may connect a pyrrole-imidazole polyamide component to a metallocomplex component. Alternatively, a linker may connect two adjacent pyrrole-imidazole polyamide components a shown schematically below:

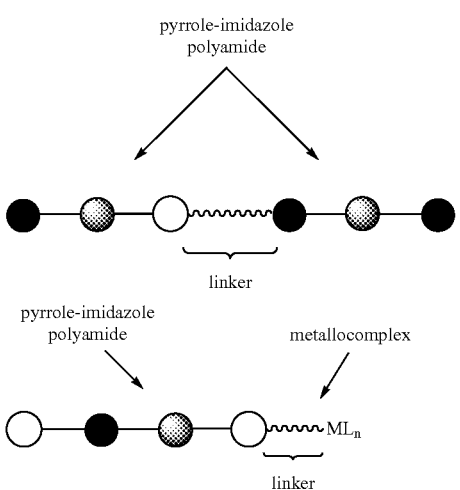

With reference to formulae (1), (3), (4) and (5), in some embodiments the linker groups ($T^1$, $T^2$, $T^3$, $T^5$) may comprise a functional group suitable for coordination to a metal ion such as Pt, Pd, Ru, Rh. In alternative embodiments, the linker groups ($T^1$, $T^2$, $T^3$, $T^5$) may comprise a functional group suitable for allowing the linker group to be covalently bound to a pyrrole-imidazole-polyamide. In further embodiments, the linker groups ($T^1$, $T^2$, $T^3$, $T^5$) may comprise a functional group suitable for allowing respective linker groups to be covalently bound to a ligand of a metallocomplex. For example, a linker group may be covalently bound to a ligand of a ruthenium complex, or platinum complex, including for example, a ligand of carboplatin, oxaliplatin or ZD0473. In one embodiment of compounds of formula (1), where c=2, a linker group $T^3$ may be covalently bonded to two pyrrole-imidazole polyamides.

In one embodiment the linker group has the formula (2):

$$—Y^1-(A)_b-Y^2— \qquad (2)$$

wherein $Y^1$ and $Y^2$ may be the same or different and are independently selected from NH, $—NH_2$, C=O, C=S, C=NH, O, OH, S, SH, S(O), S(O)$_2$, $NR^3$, $NHR^3$, $N(R^3)_2$, an optionally substituted cycloalkylamine, an optionally substituted cycloalkyldiamine, and an optionally substituted heteroaryl group (e.g., an optionally substituted N-heteroaryl group such as pyridyl, phenanthrolinyl, 2,2'-bipyridyl); where each $R^3$ is independently selected from alkyl, cycloalkyl, aryl or heteroaryl;

A is selected from an optionally substituted $C_{1-10}$ alkylene, an optionally substituted $C_{2-10}$ alkenylene, an optionally substituted $C_{2-10}$ alkynylene, an optionally substituted $C_{3-6}$ cycloalkylene, an optionally substituted $C_{6-10}$ aryl, C=O, C=S, and C=NH, NH, O, S, $NH_2$, OH, SH, S(O), S(O)$_2$, amino acids, and spermidine; and n is an integer selected from 1 to 20, wherein when n is an integer greater than 1, each (A) group may be the same or different.

$Y^1$ and $Y^2$, respectively, correspond to a group which may be covalently bonded to a heterocyclic ring of a pyrrole-imidazole polyamide, or a group which may be covalently bonded to a ligand of a metallocomplex, or a group which may function as a ligand and coordinate to a metal ion of a metallocomplex.

In one embodiment of a linker of formula (2) according to the present invention, one of $Y^1$ and $Y^2$ comprises a group capable of coordinating to a metal ion, and the other of $Y^1$ and $Y^2$ comprises a group which forms a covalent bond with a heterocyclic ring of a pyrrole-imidazole-polyamide.

In another embodiment, one of $Y^1$ and $Y^2$ may bond to a metallocomplex. For example, one of $Y^1$ and $Y^2$ may form a covalent bond with a ligand coordinated to a metal ion of a metallocomplex. Alternatively, one of $Y^1$ and $Y^2$ may function as a ligand and coordinate to a metal ion of a metallocomplex.

In another embodiment, when c=2, $Y^1$ may form a covalent bond with a heterocyclic ring of a pyrrole-imidazole polyamide and $Y^2$ may form a covalent bond with a heterocyclic ring of a pyrrole-imidazole polyamide.

In one embodiment the linker group may have the formula (2a)

$$—NH-(A)_n-NH_2— \qquad (2a)$$

where A and n are as defined above, and where the $—NH_2$ moiety is capable of coordinating to a metal ion, such as Pt, Pd, Ru, Rh; and the —NH— group is covalently bound to a heterocyclic ring of a pyrrole-imidazole polyamide.

For example, in one embodiment when A is alkylene, the linker group may be an alkylenediamine radical "—NH—$(CH_2)_n$—$NH_2$—", where n is an integer from 1 to 20. For example, a $C_{1-10}$ alkylenediamine, $C_{1-8}$ alkylenediamine, $C_{1-6}$ alkylenediamine, $C_{1-4}$ alkylenediamine, $C_{1-2}$ alkylenediamine, etc. For example, the alkylenediamine may be methylenediamine, 1,2-ethylenediamine, 1,3-propylenediamine, 1,4-butylenediamine, 1,5-pentylenediamine, or 1,6-hexylenediamine.

In another embodiment, each A may be alkylene or O and the linker group may comprise —NH—$CH_2CH_2CH_2$—O—$CH_2CH_2$—O—$CH_2CH_2$—O—$CH_2CH_2CH_2$—$NH_2$. In a further embodiment, the linker may comprise at least one carbonyl group, e.g, the linker group may be —NH—C(O)—$CH_2CH_2$—NH—C(O)—$CH_2CH_2CH_2NH_2$—.

In alternative embodiments, the linker may comprise —S—$(CH_2)_n$—O—$(CH_2)_n$—S—, or —NH—$(CH_2)_n$—O—, where n is an integer from 1 to 20.

In other embodiments, the linker may comprise one or more amino acid residues including for example, glycinyl, alaninyl, valinyl, leucinyl, isoleucinyl, methioninyl, prolinyl, phenylalaninyl, tryptophanyl, serinyl, threoninyl, cysteinyl, tyrosinyl, asparaginyl, glutaminyl, aspartyl, glutamyl, lysinyl, argininyl and histidinyl residues. In one embodiment, the linker comprises a cysteinyl residue. In one embodiment the linker is —C(O)—NH—$CH_2$—C(O)—NH—CH($CH_2SH$)—C(O)—NH—.

In one embodiment the linker group may comprise $$—Y^1—(CR^1R^2—X)_n—Y^2—$$

wherein $Y^1$ and $Y^2$ are as defined above for formula (2);

$R^1$ and $R^2$ are independently selected from hydrogen, $C_{1-6}$ alkyl, $C_{6-10}$ aryl, $C_{3-6}$ cycloalkyl, $C_{3-6}$ heterocycloalkyl, and $C_{6-10}$ heteroaryl;

X is selected from NH, O, S, spermidine, or is absent; or a ($CR^1R^2$—X) group taken together may be $C_{3-6}$ cycloalkyl, $C_{3-6}$ heterocycloalkyl, $C_{6-10}$ aryl or $C_{6-10}$ heteroaryl; and n is an integer selected from 1 to 20, wherein when n is an integer greater than 1, each ($CR^1R^2$—X) group may be the same or different.

n may be an integer selected from 1, 2, 3, 4, 5, 6, 7, 8, 9, 10, 11, 12, 13, 14, 15, 16, 17, 18, 19 and 20.

In one embodiment the linker group may comprise $$—NH_2—(CR^1R^2—X)_n—NH—$$

where $R^1$, $R^2$, X and n are as defined above, and where the —NH$_2$ moiety is capable of coordinating to a metal ion, such as Pt, Pd, Ru, Rh; and the —NH— group forms a covalent bond to a heterocyclic ring (e.g, a terminal heterocyclic ring) of a pyrrole-imidazole polyamide.

The present invention also relates to a process for preparing compounds of formula (1), or formula (5), comprising reacting a compound of formula (4) with a metal coordination complex to produce a compound of formula (1), or formula (5), respectively. Compounds of formula (4) may be concatenated before reacting with a coordination metal complex.

The present invention also relates to a stepwise process for preparing compounds of formula (3) wherein modular "building blocks" may be systematically (eg sequentially) concatenated and the steps may be carried out in any order. Respective pyrrole-imidazole polyamides, linker groups and metal coordination complexes, may be the same or different and may be arranged in any order. Appropriate protecting groups may be employed wherever necessary.

A general example of a process for preparing a compound of formula (3) may be envisaged which comprises the steps of: reacting a suitably functionalised pyrrole-imidazole polyamide with a suitably functionalised linker to produce a compound "$P^1$-$T^4$"; reacting compound "$P^1$-$T^4$" with a suitably functionalised pyrrole-imidazole polyamide "$P^2$" to produce a compound "$P^1$-$T^4$-$P^2$"; reacting the compound "$P^1$-$T^4$-$P^2$", with a suitably functionalised linker "$T^5$" to produce a compound "$P^1$-$T^4$(-$T^5$)-$P^2$"; reacting the compound "$P^1$-$T^4$(-$T^5$)-$P^2$" with a suitable metal coordination complex to produce a compound "$P^1$-$T^4$(-$T^5$-$M^3$)-$P^2$" to produce a compound of formula (3). If desired the compound "$P^1$-$T^4$(-$T^5$-$M^3$)-$P^2$" may be subsequently reacted with a suitably functionalised compound "$M^1$-$T^1$" and/or "$M^2$-$T^2$" and/or "[$P^1$-$T^4$]-$T^5$-$P^2$" in any order to produce further compounds of formula (3). It will be understood by those skilled in the art that the above generalised stepwise synthetic strategy may include the addition and removal of appropriate protecting groups from functional moieties as appropriate. Suitable protecting groups and methods for their addition and removal are known in the art.

At least one heterocyclic ring (e.g, a terminal heterocyclic ring) of a pyrrole-imidazole polyamide may be substituted with a functional moiety which allows the pyrrole-imidazole-polyamide to be covalently bonded by reaction with a suitable functional group to a "linker" group. Examples of suitable functional moieties would be known to those skilled in the art and include, for example, aldehydes, carboxylic acids, esters, amines, hydroxyl and thiol residues.

Compounds according to the present invention comprise one or more pyrrole-imidazole polyamides and one or more metal complexes and may selectively target a polynucleotide by binding to short motifs. For example, the motif may be about 3, 4, or 5 bases to about 30 bases in length, about 7 bases to about 28 bases, about 9 bases to about 26 bases, about 10 bases to about 24 bases, about 11 bases to about 22 bases, about 12 bases to about 20 bases, about 14 bases to about 19 bases, or about 16 bases to about 18 bases in length. The pyrrole-imidazole polyamide chain may be used to target a sequence in the minor groove or major groove of a polynucleotide.

In accordance with the present invention, a pyrrole-imidazole polyamide can be chosen to selectively target a minor groove of a polynucleotide, such as DNA, and allow a therapeutic agent, (e.g, a metal coordination complex such as cisplatin, transplatin, oxaliplatin, carboplatin, Pt(dac)Cl$_2$ and the like), to bind covalently in a minor or major groove of DNA. A therapeutic metallocomplex may bind covalently to a major groove of DNA.

Also in accordance with the present invention, a pyrrole-imidazole polyamide chain may be used to selectively target a reporter group, for example a metal coordination complex such as [Ru(diimine)$_3$]$^{2+}$, to a major groove or minor groove of DNA. For example, the ruthenium complex [Ru(phen)$_2$(Dpq)Cl$_2$ may bind to a minor groove.

Compounds of the present invention may also comprise one or more metallocomplex(es) which may function as a therapeutic agent and/or a reporter group. For example, compounds of the present invention may comprise one or more therapeutic metallocomplex(es) such as a palladium complex, a platinum complex (e.g., cisplatin, transplatin, Pt(dac)Cl$_2$, carboplatin, ZD0473, oxaliplatin), and/or a fluorophore, such as a ruthenium complex.

In the compounds of the invention, a linker group is used to space the metal coordination complex from the sequence selective pyrrole-imidazole polyamide. The length of the linker group can be selected to optimally position the metal coordination complex in a minor or a major groove of DNA. Compounds may be prepared using a modular or step-wise "building block" approach such that a metallocomplex may be able to bind preferentially to a major or minor groove as desired.

The linker group may be chosen to space the metal coordination complex from the pyrrole-imidazole polyamide so as to optimise the binding interaction of both the polyamide and the metal coordination complex. In addition, linker group "$T^4$" in formula (3) may be chosen so as to confer a desired configuration or spacial arrangement of respective pyrrole-imidazole polyamide groups, such as connecting two pyrrole-imidazole polyamides via a "hairpin bend". In one embodiment, when a polynucleotide of a compound of the invention is positioned at a given sequence, the linker group is sufficiently long and has a suitable conformation such that a metallocomplex may bind to a major or minor groove of the polynucleotide.

The sequence selective pyrrole-imidazole polyamide chain targets the compound to a selected region of DNA. Specific heterocyclic rings in the polyamide chain may be selected on the basis of the nucleotide sequence of interest. Rules for the design of sequence selective polyamide chains are known to those of skill in the art. For example rules for the design of sequence selective polyamide chains are described in U.S. Pat. No. 6,472,537 to Baird and Dervan, entitled "Polyamides for binding in the minor groove of double stranded DNA"; and *Bioorganic and Medicinal Chemistry*, 9, (2001) 2215-2235, the entire contents of which are incorporated herein by cross-reference. For example, it is known that Py/Im targets C-G base pairs; Py/Hp targets A-T base pairs; Hp/Py targets T-A base pairs and Im/Py targets G-C base pairs. Thus, for example, the combination of polyamides Im/Im/Im and Py/Py/Py would be selective for a central core of 5'-CCC-3' in a polynucleotide. As a further example, the combination of polyamides Hp/Py/Hp/Py and Py/Hp/Py/Hp would be selective for a core sequence of 5'-TATA-3'.

Figure 8:
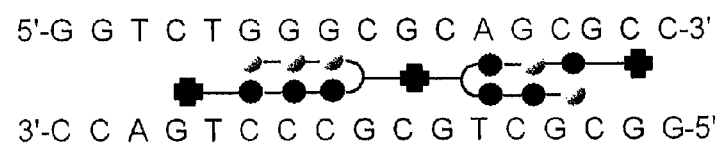
FIG. 8 is a schematic representation of a polynucleotide sequence.

Interaction of a compound of the present invention with a polynucleotide sequence is represented schematically in FIG. 8 for a compound of formula (3).

5'-GGTCTGGGCGCAGCGCC-3'
3'-CCAGTCCCGCGTCGCGG-5'

The sequence selective targeting nature of the compounds of the present invention provides the ability to target, for example, a therapeutic or reporter group to any sequence of interest. Such sequences may be associated with a particular disease state, such as cancer, a disease such as Hepatitis C, susceptibility to a disease, or with infection by an infectious organism, such as HIV. For example, compounds of the invention may be used to specifically deliver a therapeutic agent to a cell infected with HIV, for example, by designing a compound of the invention to target a polynucleotide sequence essential to viral replication. For example, it is known that the Rev Response element (RRE) is an HIV-1 RNA structure essential to viral replication (Frankel et al., *Annu. Rev. Biochem,* 1998, 67, 1-25; Pollard et al, *Annu. Rev. Microbiol.,* 1998, 52, 491-532). Similarly, the transactivation control region of HIV-1 (TAR31) is also believed to be necessary for transcription of full length HIV RNA, such that inhibition of the RNA protein interaction by targeting specific compounds of the invention to a conserved sequence(s) within TAR31 may represent another target for treatment or prevention of HIV infection.

Compounds according to the present invention may bind to a polynucleotide sequence in a 5' to 3' direction or in a 3' to 5' direction.

Compounds of formula (1), (3) and (5) may self-assemble in solution to form oligomeric structures. For example, a self-assembled dimer of a compound of formula (1) [Im/Im/Py-Pt] is illustrated schematically below:

one compound of formula (1), (3) or (5), or salt thereof, or a pharmaceutical composition thereof.

The disease may be a proliferative disease, such as cancer. The cancer may be selected from breast cancer, ovarian cancer, lung cancer (eg small cell carcinoma), oesophageal cancer, testicular cancer, cervical cancer, bladder cancer, thyroid cancer, neoblastoma, leukaemia, and osteogenic sarcoma. In an alternative embodiment, the disease may be a viral disease, such as HIV. In another embodiment, the disease may be hepatitis, eg, hepatitis C.

The present invention also relates to a method of diagnosis comprising contacting a biological sample with a diagnostically effective amount of at least one compound of formula (1), (3) or (5), or a salt thereof, or a pharmaceutical composition thereof. In one embodiment the method comprises contacting said biological sample in vivo, for example, by administering to said mammal a diagnostically effective amount of said compound or composition. In another embodiment the method comprises obtaining a biological sample from said mammal and contacting said sample with a diagnostically effective amount of said compound or composition.

Preparation of Compounds

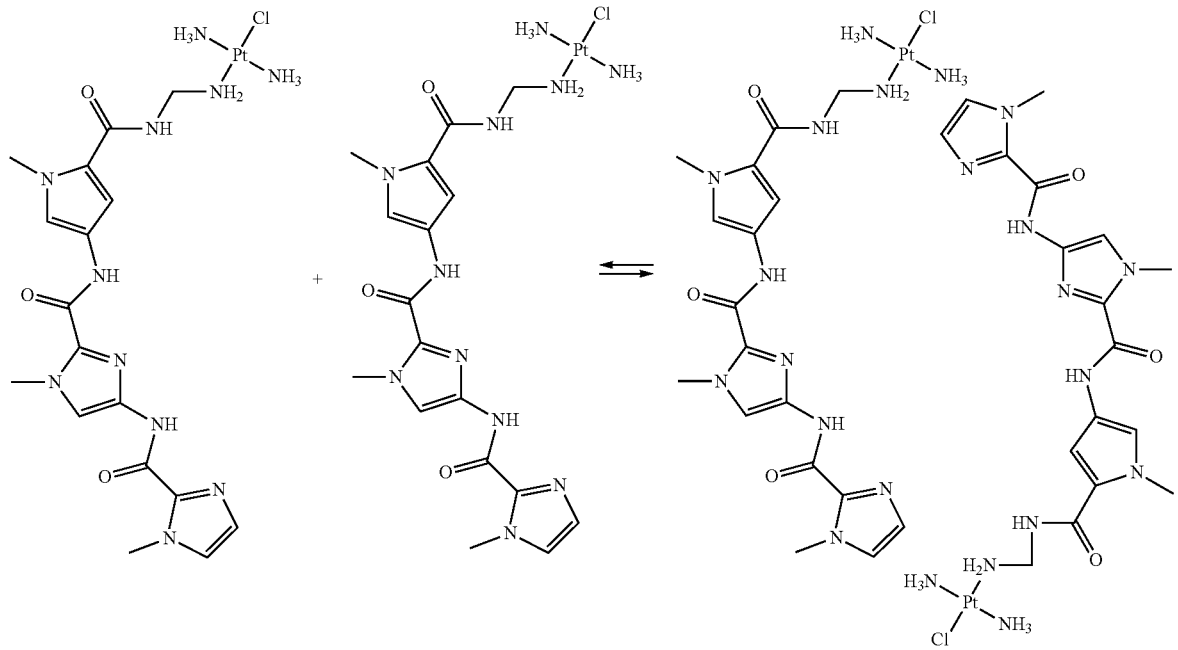

The present invention also relates to a method of targeting a therapeutic agent(s) and/or a reporter group(s) to a sequence in a polynucleotide comprising contacting biological material suspected of containing said sequence with a compound of formula (1), formula (3), or formula (5).

In one embodiment of the invention the method comprises contacting the biological material in vivo. In another embodiment the method comprises obtaining a sample of biological material from an organism and contacting said sample with a compound of formula (1), formula (3) or formula (5), or salt thereof, in vitro.

The present invention also relates to a method of treating a disease comprising administering to a mammal in need of such treatment a therapeutically effective amount of at least Compounds of the present invention are adaptable to being prepared in a modular or step-wise fashion. Stepwise syntheses may allow the number and composition of the component polyamide(s), linker group(s) and metallocomplex(es) to be varied in a controlled manner. For example, the length and composition of the polyamide chain may be selected to target to a particular nucleotide sequence. Individual modular compounds of formula (1), (3), (4) and (5) may be concatenated with other modular compounds, or attached to additional metallocomplex(es), to produce compound(s) of formula (1), (3), or (5) having the desired number of pyrrole-imidazole polyamide(s) capable of selectively targeting a particular polynucleotide sequence. Compounds of the invention, such as compounds of formulae (1), (3), (4) and (5) may be prepared which are capable of targeting a polynucleotide sequence comprising a selected core sequence of about 2, 3, 4, 5, 6, 7, 8, 9, or about 10 base pair groupings. In addition, the length and composition of respective "linker moieties" may be varied to optimise interaction of a metallocomplex with a major or minor groove of a polynucleotide when the polyamide is positioned at a selected sequence.

Compounds in accordance with the present invention may be concatenated and or coordinated to metallocomplex(es) in any combination as required. Compounds in accordance with the present invention may be prepared using the methods described herein, or by applying other methods known in the art.

By way of example, a pyrrole-imidazole polyamide comprising 2 to 10 heterocyclic rings and which selectively targets a sequence of interest, may be prepared using methods described herein and elsewhere (eg, U.S. Pat. No. 6,472,537 to Baird and Dervan, entitled "Polyamides for binding in the minor groove of double stranded DNA"; and *Bioorganic and Medicinal Chemistry*, 9, (2001) 2215-2235, the entire contents of which are incorporated herein by cross-reference). The pyrrole-imidazole polyamide may be coupled to a suitable linker group to produce a compound of formula (4). Compound(s) of formula (4) may be reacted with a suitable metal coordination complex, (eg, a platinum complex such as transplatin or cisplatin, or a ruthenium complex) to produce a compound of formula (1). Compounds of the present invention may be subsequently reacted with, for example, another compound of formula (4), and so on. This stepwise synthesis is represented schematically below:

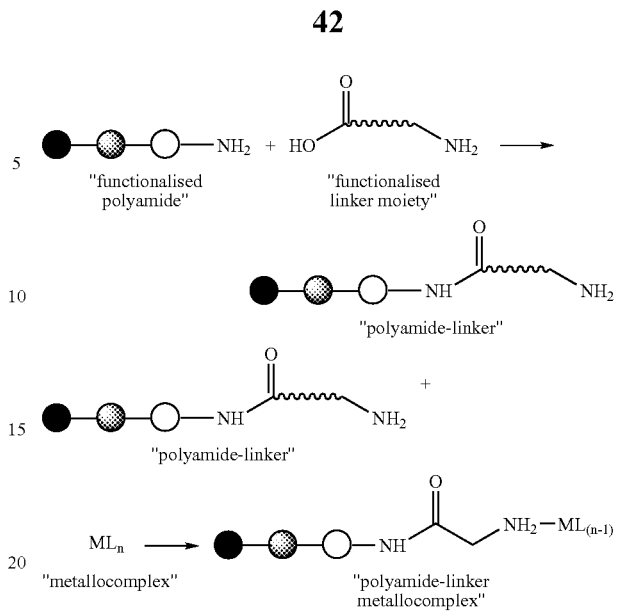

Use of a "modular" or stepwise synthetic strategy enables a wide variety of compounds to be produced. Protecting groups for various functional moieties may be employed as appropriate and suitable protecting groups are known to those skilled in the art.

The above modular or stepwise synthetic strategy may be adapted to similarly construct compounds of formula (5) as shown schematically below:

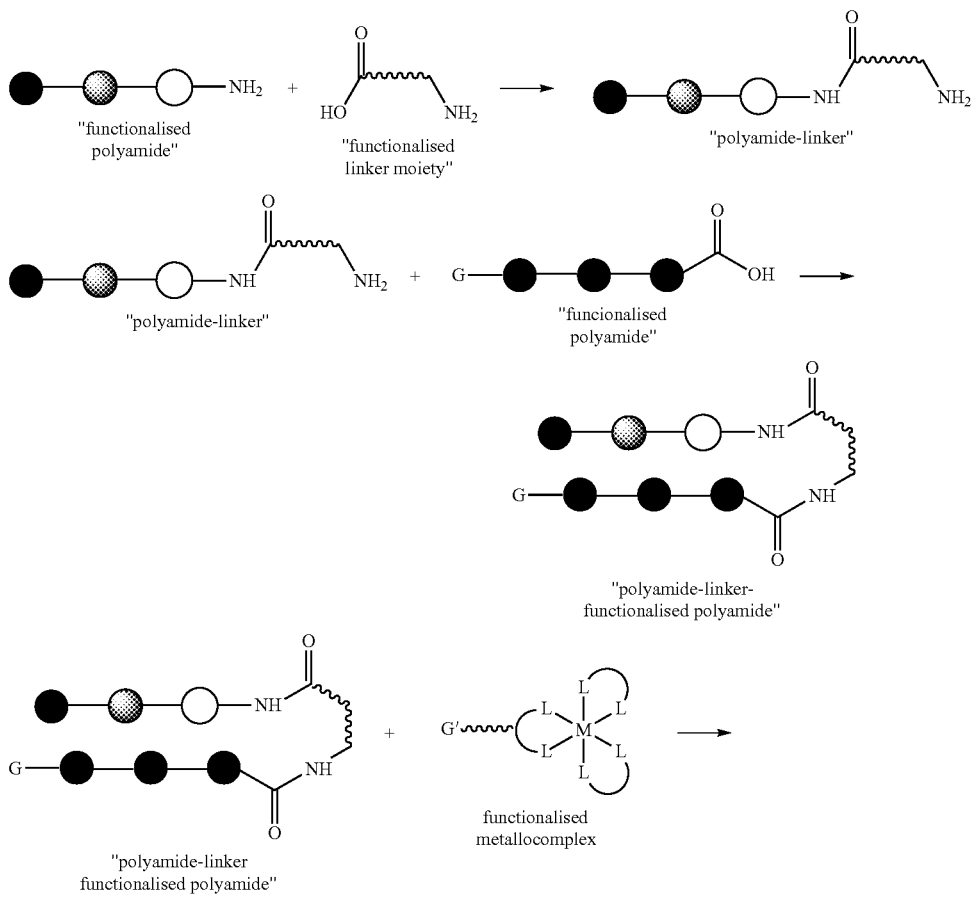

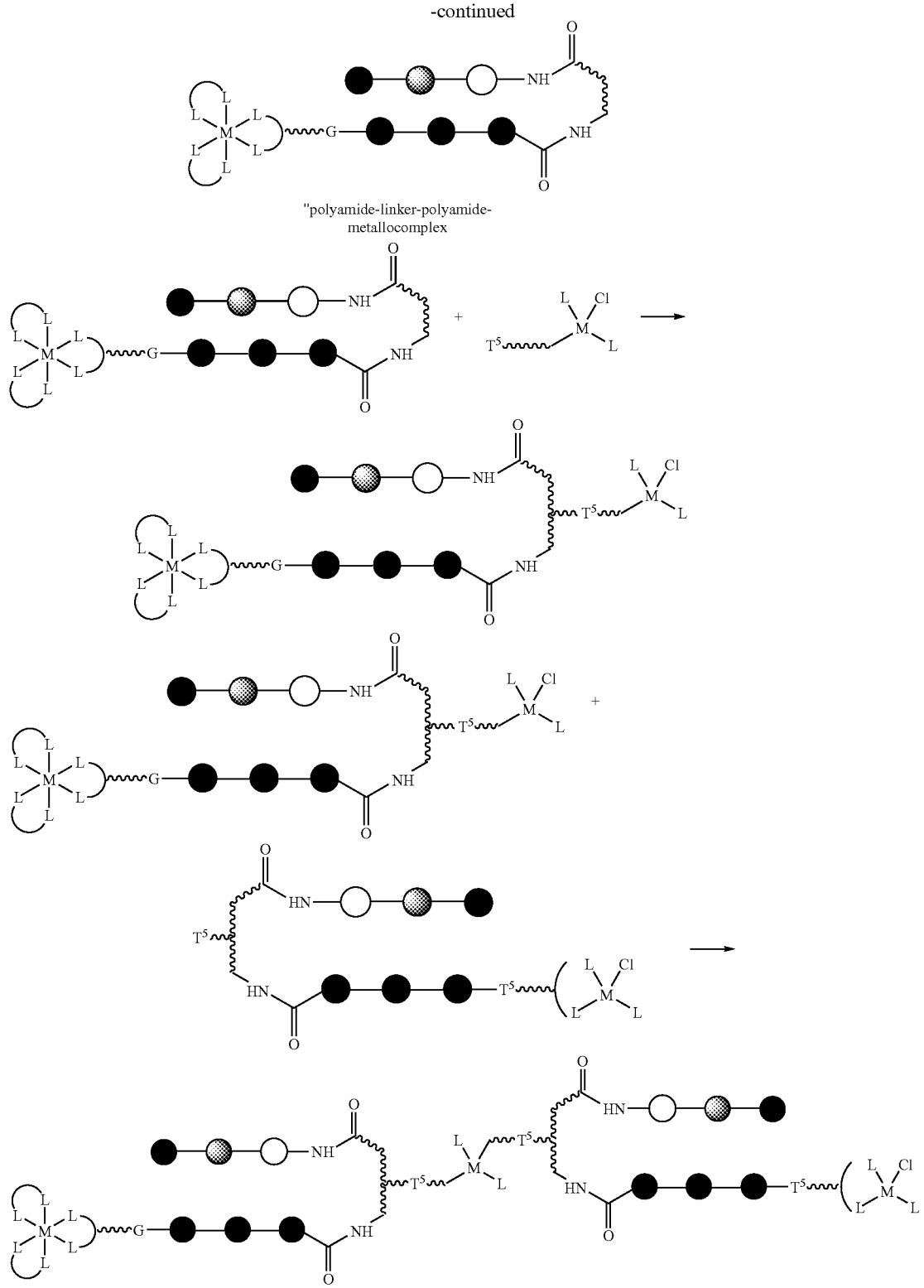

"polyamide-linker-polyamide-metallocomplex

The overall charge of compounds of formulae (1), (3) and (5) is related to the number of metallocomplexes and the metal ion(s) present. Accordingly, charge may be varied by increasing or decreasing the number of metallocomplexes in a compound, or by incorporating metallocomplexes having different metal ions. Increasing the overall charge may increase the affinity for negatively charged DNA. The overall charge may be selected so as to optimise cellular uptake of a compound.

Compounds of the present invention may be prepared using methods known to those skilled in the art. Suitable methods are generally described, for example, and intermediates thereof are described, for example, in Houben-Weyl, *Methoden der Organischen Chemie*; J. March, *Advanced Organic Chemistry*, 4th Edition (John Wiley & Sons, New York, 1992); D. C. Liotta and M. Volmer, eds, *Organic Syntheses Reaction Guide* (John Wiley & Sons, Inc., New York, 1991); R. C. Larock, *Comprehensive Organic Transformations* (VCH, New York, 1989), H. O. House, *Modern Synthetic Reactions* 2nd Edition (W. A. Benjamin, Inc., Menlo Park, 1972)

Sequence selective chains can be prepared using techniques and reagents known to those skilled in the art. The syntheses may be carried out in a step-wise fashion based on successive amide coupling reactions. Those skilled in the art will appreciate that automated solid phase coupling methods may also be used to synthesise polyamide compounds in accordance with the present invention. Similarly, solid phase synthetic techniques may be used to successfully couple amino acids. Heterocyclic rings of choice, for example N-methylpyrrole (Py), N-methyl imidazole (Im), 3-hydroxy N-methyl pyrrole (Hp), may be incorporated into the polyamide as required depending on the nucleotide sequence to be targeted. Suitable protecting groups for use in amide coupling reactions are well known by those skilled in the art and have been described, for example, in Greene et al., *Protective Groups in Organic Synthesis*; John Wiley & Sons, 2nd Edition, 1991. Typically, t-butyl carbamate (BOC) or (FMOC) protecting groups may be used to protect terminal amines. For example, FMOC protected diaminobutyric acid (DABA) may be used. Different coupling reagents can be used to help minimise formation of by-products and maximise yields.

Pyrrole-imidazole polyamides may include a functional group on a heterocyclic ring (eg, a terminal heterocyclic ring) which subsequently may be reacted with a functionalised linker group, thereby covalently attaching another linker group to the polyamide.

Once a suitable sequence selective pyrrole-imidazole polyamide has been prepared, the metal coordination complex may be attached to the linker moiety at a terminal end of the chain. Alternatively, it may be possible to attach the metal coordination complex to the linker moiety before the linker is attached to the polyamide. A further alternative is to attach the metal coordination complex and linker moiety to a heterocyclic ring eg, Im, Py or Hp (or dimer, trimer etc comprising Im, Py, Hp), then subsequently carry out further amide couplings to attach further heterocyclic rings to build up a polyamide chain or desired length.

By varying the ratio of pyrrole-imidazole polyamide to metal coordination complex (eg, 1:1; 2:1, 1:2 etc), it is possible to manipulate the proportion of products formed. Compounds of the present invention may be isolated using methods well known to those skilled in the art, for example, column chromatography, recrystallization, size exclusion chromatography (eg, sephadex) and HPLC.

Compounds according to the present invention may be prepared as salts. Those skilled in the art would readily be able to convert such salts into other salt forms, eg, by ion exchange methods.

Compounds according to the present invention may bind irreversibly to polynucleotides, such as DNA, through coordination of the metal ion to a suitable donor/ligand group on the polynucleotide. Where the compounds are covalently bound to DNA, any testing can be destructive to both the metal complex and the DNA. The nature of the binding of the compounds according to the invention with DNA can be probed using a variety of techniques known to those skilled in the art to characterise the interactions. For example, (a) DNA-Melting Experiments Monitored by Absorption Spectrophotometry—UV melting experiments can be used to assess the impact of compounds of formulae (1), (3) and (5) on the thermal stability of DNA duplexes. Techniques are known to those skilled in the art.

By way of example, for the compound trans-Im/Py/Py-Pt three 11-mer DNA duplexes can be used:
1) d(CATTGTCAGAC)$_2$ (target site),
2) d(CATTGACAGAC)$_2$ (single mismatch site) and
3) d(CATTGAGAGAC)$_2$ (double mismatch site).

Figure 2:
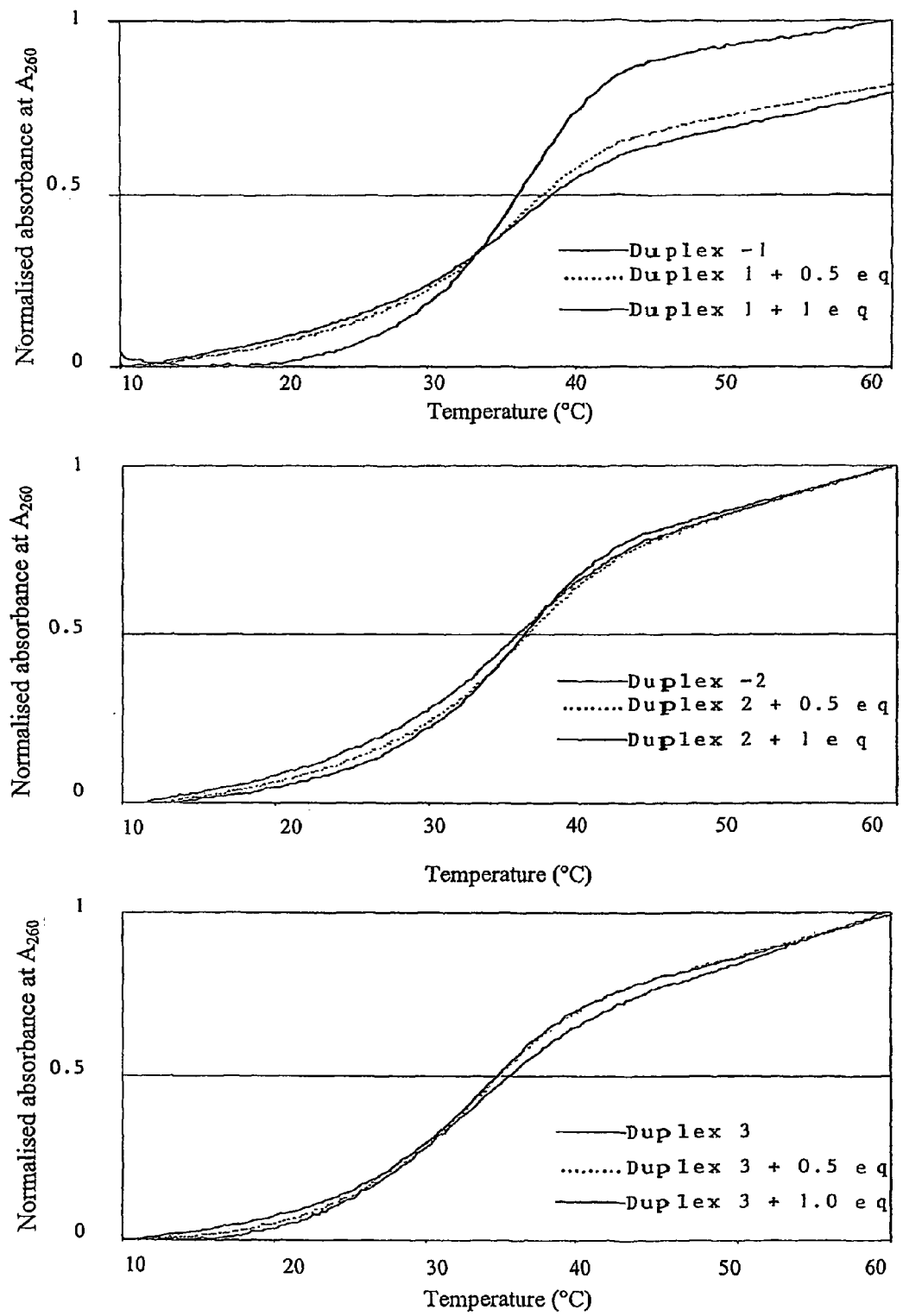
FIG. 2—DNA melting profiles for Im/Py/Py-Pt at 260 nm

The concentration of the duplex is kept constant, while the complex concentration ratio is be varied with respect to the DNA. The measured differences melting temperature ($\Delta T_m$) between the target site binding to the complexes and that of a single mismatch site and a double mismatch site can be compared with the extent to which the target sequence deviates from the sequence of the match site being correlated with the magnitude of $\Delta T_m$, as illustrated in FIG. 2.

(b) Binding Studies by Circular Dichroism (CD) Spectropolarimetry—CD spectropolarimitry may be used to determine the equilibrium constant and hence binding strength of the metallo complexes. One advantage of this method is its sensitivity. Generally, DNA may be titrated into a fixed concentration of a compound of the invention, eg, a compound of formula (1), (3) or (5) resulting in changes to the spectrum. The changes are generally monitored until saturation is reached. The equilibrium constant can be determined using standard techniques, such as Scatchard plot, the McGhee Von Hippel model, or least squares, for analysis.

Preferential binding may be quantified by varying the DNA duplexes. Final CD spectra may be normalised to reflect equimolar concentrations of duplex.

(c) Footprinting Studies—The ability of compounds to bind in a sequence specific fashion may be determined though transcription assays. For example, a small fragment of double stranded DNA of specified length may be incubated with a compound of the invention, eg, a compound of formula (1), (3) and (5), then incubated with a cleavage agent under conditions that result in an average of one cleavage event per molecule. The DNA can then purified and analysed by electrophoresis though through 12% denatured polyacrylamide sequencing gels and visualised using techniques known in the art. If cleavage occurs randomly, the resulting populations of single-stranded DNA fragments will differ in length by a single nucleotide and will appear as a semicontinuous ladder on the gel. However, if a region of DNA is protected from cleavage there will be a gap in the ladder of fragments. The "footprint" can be precisely located, for example, by aligning the gap with a set of Maxam-Gilbert sequencing reactions carried out on the same DNA.

(d) Cell-lines—IC$_{50}$ values (ie, the concentration of compound of the invention required to inhibit cell growth by 50%) can be determined using known techniques.

Pharmaceutical and/or Therapeutic Formulations

In accordance with the present invention, when used for the treatment of disease, compounds of the invention may be administered alone. Alternatively, the compounds may be administered as a pharmaceutical formulation which comprises at least one compound of formulae (1), (3) and/or (5) according to the invention. The compound(s) may also be present as suitable pharmaceutically acceptable salts.

By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art.

For instance, suitable pharmaceutically acceptable salts of compounds according to the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds of the present invention therefore include acid addition salts.

For example, S. M. Berge et al. describe pharmaceutically acceptable salts in detail in *J. Pharmaceutical Sciences*, 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Convenient modes of administration include injection (subcutaneous, intravenous, etc.), oral administration, inhalation, transdermal application, or rectal administration. Depending on the route of administration, the formulation and/or compound may be coated with a material to protect the compound from the action of enzymes, acids and other natural conditions which may inactivate the therapeutic activity of the compound. The compound may also be administered parenterally or intraperitoneally.

Dispersions of the compounds according to the invention may also be prepared in glycerol, liquid polyethylene glycols, and mixtures thereof and in oils. Under ordinary conditions of storage and use, pharmaceutical preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

In one embodiment of the invention, the compound of the invention may be administered orally, for example, with an inert diluent or an assimilable edible carrier. The compound and other ingredients can also be enclosed in a hard or soft shell gelatin capsule, compressed into tablets, or incorporated directly into an individual's diet. For oral therapeutic administration, the compound can be incorporated with excipients and used in the form of ingestible tablets, buccal tablets, troches, capsules, elixirs, suspensions, syrups, wafers, and the like. Suitably, such compositions and preparations may contain at least 1% by weight of active compound. The percentage of the compound of formula (1) in pharmaceutical compositions and preparations can, of course, be varied and, for example, can conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of compound in therapeutically useful compositions is such that a suitable dosage will be obtained.

The language "pharmaceutically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment is contemplated. Supplementary active compounds can also be incorporated into the compositions according to the present invention. It is especially advantageous to formulate parenteral compositions in dosage unit form for ease of administration and uniformity of dosage. Dosage unit form as used herein refers to physically discrete units suited as unitary dosages for the individual to be treated; each unit containing a predetermined quantity of compound is calculated to produce the desired therapeutic effect in association with the required pharmaceutical carrier. The compound may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In one embodiment, the carrier may be an orally administrable carrier.

A particularly suitable form of a pharmaceutical composition is a dosage form formulated as enterically coated granules, tablets or capsules suitable for oral administration.

In one embodiment, the compound may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the a compound nalogue in the required amount in an appropriate solvent with one or a combination of ingredients enumerated above, as required, followed by filtered sterilisation. Generally, dispersions are prepared by incorporating the compound into a sterile vehicle which contains a basic dispersion medium and the required other ingredients from those enumerated above.

Tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the compound an be incorporated into sustained-release preparations and formulations.

Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the pharmaceutical compositions according to the invention can be carried out. One skilled in the art would be able, by routine experimentation, to determine effective, non-toxic dosage levels of the compound and/or composition of the invention and an administration pattern which would be suitable for treating the disorders or diseases to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; suitably, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be up to about 500 mg/m$^2$. Generally, an effective dosage may be in the range of about 25 to about 500 mg/m$^2$, about 25 to about 350 mg/m$^2$, about 25 to about 300 mg/m$^2$, about 25 to about 250 mg/m$^2$, about 50 to about 250 mg/m$^2$, or about 75 to about 150 mg/m$^2$.

The compounds of the invention may be used in combination with other known treatments, such as surgery and/or therapeutic agents, including chemotherapeutic or radiotherapeutics. When used in the treatment of solid tumours, compounds of the present invention may be administered with chemotherapeutic agents such as: adriamycin, taxol, fluorouricil, melphalan, alpha interferon, COMP (cyclophosphamide, vincristine, methotrexate and prednisone), etoposide, mBACOD (methotrexate, bleomycin, doxorubicin, cyclophosphamide, vincristine and dexamethasone), PROMACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethylenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including brequinar.

The invention will now be described in more detail, by way of illustration only, with respect to the following examples. The examples are intended to serve to illustrate this invention and should not be construed as limiting the generality of the disclosure of the description throughout this specification.

EXAMPLES

In the present invention one example of a target sequence may be d(CATTGTCAGAC)$_2$. Two other 11-mer sequences have been prepared—one with one mismatch and the other with two mismatches. Analogous 18-mers have also been prepared to assess the trinuclear complex, trans-Im/Py/Py-Pt-Py/Py/Im. The binding constant of the dimer and trimer may be determined by measuring the change in Circular Dichroism (CD) upon titration of each of the three duplexes. Footprinting experiments may be used to assess the binding fidelity.

The animal tumour, L1210 leukaemia, may be used as a primary screen of newly synthesised compounds in addition to cisplatin resistant L1210 cell lines.

Example 1

Synthesis of Im/Py/Py

The polyamide Im/Py/Py was prepared by a similar method to that of Lown et al. (*J. Org. Chem.*, 1985, 50(20), 374-379). The synthesis of Im/Py/Py is shown schematically in FIG. 1.

Methyl-4-nitropyrrole-2-carboxylic acid (1)

Acetic anhydride (8 ml) and nitric acid (70%, 1.6 mL) were heated to 50° C. for 15 minutes and cooled to room temperature. The solution was then slowly added to a suspension of 1-methyl-2-pyrrolecarboxylic acid (2.0 g, 0.02 mol) in Ac$_2$O (12 ml) cooled to −25° C. The mixture was stirred for 30 min at −15° C., warmed to room temperature and stirred for another 20 min. The mixture was again cooled to −25° C. and the resulting precipitate collected in a funnel cooled with dry ice. The solid was washed with cold Ac$_2$O (−25° C.), followed by Ac$_2$O:CCl$_4$ (1:1, −25° C.), and then CCl$_4$ and hexane. The yellow solid was dissolved in NaOH (1M) and acidified with HCl to yield the product as a light cream solid which was collected and air-dried. Yield 0.98 g (36%). $^1$H NMR (DMSO): δ 8.19 (d, 1H, J=1.8 Hz); 7.23 (d, 1H, J=2.0 Hz); 3.90 (s, 3H).

Methyl 1-methyl-4-nitropyrrole-2-carboxylate (2)

A solution of $H_2SO_4$ (0.4 ml) in MeOH (4 ml) was added to compound 1 (0.4 g, 2.35 mmol) and the mixture refluxed for 24 hr. Water was added and the mixture extracted with $CHCl_3$. The organic layer was dried ($MgSO_4$), and the solvent evaporated under vacuum. The residue was purified by flash chromatography (100% $CH_2Cl_2$) to yield the product as a crystalline solid. Yield 0.33 g (79%). $^1$H NMR (DMSO): δ 7.57 (d, 1H, J=2.1 Hz); 7.40 (d, 1H, J=2.0 Hz); 3.99 (s, 3H); 3.86 (s, 3H, $COOCH_3$).

Methyl 1-methyl-4-(1-methyl-4-nitropyrrole-2-carboxamido)pyrrole-2-carboxylate (3)

Compound 2 (0.34 g, 1.85 mmol) in methanol (150 ml) and Pd/C (10%, 0.03 g) were stirred under $H_2$ (1 atm) for 1 hr. The catalyst was removed (celite), and the solvent evaporated to dryness. Diisopropyl ethylamine (1 ml) in THF (5 ml) was added, the solution cooled to −20° C., and treated with a solution of the acid chloride of 1 (0.31 g, refluxed with thionyl chloride) in THF (5 ml). The mixture was allowed to warm to room temperature and stirred for a further 30 min. The solvent was evaporated to dryness, and water (5 ml) added. The solid was collected, and recrystallized by dissolving in hot DMF and precipitating with ethanol. Yield 0.46 g (82%). $^1$H NMR (DMSO): δ 10.23 (s, 1H, NH); 8.16 (d, 1H, J=1.9 Hz); 7.52 (d, 1H, J=2.0 Hz); 7.43 (d, 1H, J=2.0 Hz); 6.87 (d, 1H, J=1.9 Hz); 3.93 (s, 3H); 3.86 (s, 3H); 3.73 (s, 3H).

1-Methyl-4-(1-methyl-4-nitropyrrole-2-carboxamido)pyrrole-2-carboxylic acid (4)

Compound 3 (0.10 g, 0.33 mmol), NaOH (0.7M, 2.4 ml) and ethanol (2.4 ml) were refluxed until the solid dissolved. The red solution was cooled and acidified with concentrated HCl to precipitate the product as a yellow solid. Yield 0.09 g, (88%). $^1$H NMR (DMSO): δ 12.19 (bs, 1H, OH); 10.18 (s, 1H, NH); 8.15 (d, 1H, J=1.9 Hz); 7.52 (d, 1H, J=1.9 Hz); 7.36 (d, 1H, J=1.9 Hz); 6.78 (d, 1H, J=1.9 Hz); 3.93 (s, 3H); 3.81 (s, 3H).

N-Di-tert-butoxycarbonyl-1,2-ethanediamine (en-BOC)

This step was carried out as described by Krapcho et al (Synthetic Communications, 1990, 20(16), 2559-2564). A solution of di-tert-butyl dicarbonate (1.0 g, 4.58 mmol) in $CH_2Cl_2$ (12 ml) was added over a period of 2.5 hr to a solution of ethylenediamine (2.1 g, 35.61 mmol) in $CH_2Cl_2$ (12 ml), which was cooled in an ice bath. The mixture was allowed to stir at room temperature for 24 hr and the solvent removed under reduced pressure. Water (20 ml) was added and the mixture filtered. The filtrate was extracted with $CH_2Cl_2$ (3×50 ml), the organic layer dried ($MgSO_4$) and the solvent evaporated to yield the product as an oil. Yield 0.64 g (87%). NMR ($CDCl_3$): δ 4.93 (bs, 1H, NH-Boc); 3.15 (q, 2H, $J_1$=6.0 Hz, $J_2$=10.8 Hz); 2.77 (t, 2H, $J_1$=6 Hz); 1.42 (s, 9H, Boc); 1.41 (s, 2H, $NH_2$).

[2-({1-Methyl-4-[(1-methyl-4-nitro-1H-pyrrole-2-carbonyl)-amino]-1H-pyrrole-2-carbonyl}-amino)-ethyl]-carbamic acid tert-butyl ester (5a)

This step was carried out as described by Dervan et al. (*J. Am. Chem. Soc.*, 1992, 114, 8783-8794.)

To a solution of compound 4 (0.07 g, 0.22 mmol), HOBT (0.04 g, 0.26 mmol) and en-Boc (0.04 g, 0.26 mmol) in THF (7 ml) at 0° C. was added EDCI (0.05 g, 0.24 mmol) in $CH_2Cl_2$ (3 ml). The solution was allowed to warm to room temperature and stirred for 20 hr. The mixture was filtered (celite), and $H_2O$ (15 ml) added. The solution was extracted with $CHCl_3$ (30 ml) and the organic layer dried ($MgSO_4$). The solvent was removed under vacuum and the crude residue purified by flash column chromatography (5% methanol/$CH_2Cl_2$) to yield the product as a yellow solid. Yield 0.073 g (70%). $^1$H NMR (DMSO): δ 10.20 (s, 1H, NH), 8.15 (d, 1H, J=1.8 Hz), 7.99 (t, 1H, J=5.4 Hz, NH), 7.55 (d, 1H, J=1.8 Hz), 7.18 (d, 1H, J=1.8 Hz), 6.85 (bs, 1H, NH-Boc); 6.83 (d, 1H, J=1.8 Hz), 3.94 (s, 3H), 3.79 (s, 3H), 3.17 (m, 2H, $CH_2$), 3.04 (m, 2H, $CH_2$), 1.37 (s, 9H, $C(CH_3)_3$).

(2-{[1-Methyl-4-[(1-methyl-4-[(1-methyl-1H-imidazole-2-carbonyl)-amino]-1H-pyrrole-2-carbonyl]-amino)-1H-pyrrole-2-carbonyl]-amino}-ethyl)-carbamic acid tert-butyl ester (6a)

Compound 5a (0.1 g, 0.23 mmol) in methanol (75 ml) was added $PtO_2$ (0.01 g) and the solution hydrogenated at 1 atm for 26 hr. Catalyst filtered (celite) and DMF (3 ml) added. Methanol removed under vacuum and N-methylimidazole-2-carboxylic acid (0.07 g, 0.55 mmol) was added followed by HOBT (0.09 g, 0.69 mmol) and TBTU (0.22 g, 0.69 mmol). Triethylamine (0.3 ml, 2.3 mmol) was added and the solution stirred for 1 hr. Solvent was removed under vacuum and the residue purified by flash chromatography (3-5% MeOH/$CH_2Cl_2$). Yield 0.1 g (42%). $^1$H NMR (DMSO): δ 10.47 (s, 1H, NH), 9.93 (s, 1H, NH), 7.98 (t, 1H, NH, J=6.0 Hz) 7.39 (d, 1H, J=1.2 Hz), 7.28 (d, 1H, J=1.5 Hz), 7.18 (d, 1H, J=1.5 Hz) 7.14 (d, 1H, J=1.8 Hz), 7.03 (d, 1H, J=1.2 Hz), 6.88-6.86 (bs, 2H, 1H and NH-Boc), 3.98 (s, 3H), 3.82 (s, 3H), 3.78 (s, 3H), 3.18 (m, 2H, $CH_2$), 3.04 (m, 2H, $CH_2$), 1.37 (s, 9H, $C(CH_3)_3$).

1-Methyl-1H-imidazole-2-carboxylic acid {5-[5-(2-amino-ethylcarbamoyl)-1-methyl-1H-pyrrol-3-ylcarbamoyl]-1-methyl-1H-pyrrol-3-yl}-amide (7a)

Compound 6a (0.29 g, 0.06 mmol) and TFA/$CH_2Cl_2$ (1:1, 2 ml) containing $H_2O$ (40 μl) were stirred at room temperature for 1.5 hr. The solvent was removed under pressure and the residue stirred with DOWEX® 550A OH anion exchange resin (0.05 g, 0.17 mmol, washed with MeOH). The solution was decanted and evaporated. $CHCl_3$ (5 ml) was added and the solid collected and dried under vacuum. Yield 0.02 g (90%). $^1$H NMR (DMSO): δ 10.49 (s, 1H, NH), 9.96 (s, 1H, NH), 8.13 (t, 1H, NH, J=6.0 Hz) 7.71 (bs, 2H, $NH_2$), 7.40 (d, 1H, J=1.5 Hz), 7.28 (d, 1H, J=1.5 Hz), 7.18 (d, 1H, J=1.5 Hz) 7.15 (d, 1H, J=1.8 Hz), 7.04 (d, 1H, J=1.2 Hz), 6.98 (d, 1H J=1.5 Hz), 3.98 (s, 3H), 3.83 (s, 3H), 3.81 (s, 3H), 3.5-3.2 (m, 2H, $CH_2$), 2.92 (m, 2H, $CH_2$).

Synthesis of trans-Im/Py/Py-Pt(Cl)(NH$_3$)$_2$

Transplatin (0.10 g, 0.34 mmol) and compound 7a (0.14 g, 0.34 mmol) in $H_2O$ (45 ml) were refluxed until the mixture dissolved (24 hr). The solution was cooled and filtered. The solvent was evaporated and MeOH (10 ml) added. The solid was removed and the filtrate concentrated. CH$_2$Cl$_2$ was added (10 ml) and stirred for 30 min. The solid was collected and dried under vacuum. The synthesis is represented schematically below. Yield 0.24 g (63%). $^1$H NMR (DMSO): δ 11.52 (s, 1H, NH), 10.09 (s, 1H, NH), 8.17 (t, 1H, J=5.4 Hz, NH), 7.84 (bs, 2H, NH$_2$), 7.56 (d, 1H, J=1.5 Hz), 7.45 (d, 1H, J=1.5 Hz), 7.32 (d, 1H, J=1.5 Hz), 7.29 (s, 1H), 7.20 (d, 1H, J=1.5 Hz), 7.15 (d, 1H, J=1.8 Hz), 7.12 (s, 1H), 6.99 (d, 1H, J=1.8 Hz), 6.95 (s, 1H), 4.00 (s, 3H), 3.90 (s, 3H), 3.83 (s, 3H), 3.81 (s, 3H), 3.6-3.2 (m, 2H, CH$_2$), 2.93 (m, 2H, CH$_2$); MS calculated for C$_{19}$H$_{30}$ClN$_{10}$O$_3$Pt$^{+1}$(677.04). Found 677.0.

1 cm. The heating rate in all experiments was 0.5° C./min. Solutions conditions are sodium phosphate (10 mM), EDTA (1 mM) and NaCl (40 mM) adjusted to pH 7.0. DNA melting curves are shown in FIG. 2.

Example 3

CD Titrations

All CD measurements were recorded on a Jasco J-810 CD spectropolarimeter at room temperature and cell length of 1 cm. Titrations were performed by incrementally adding ali-

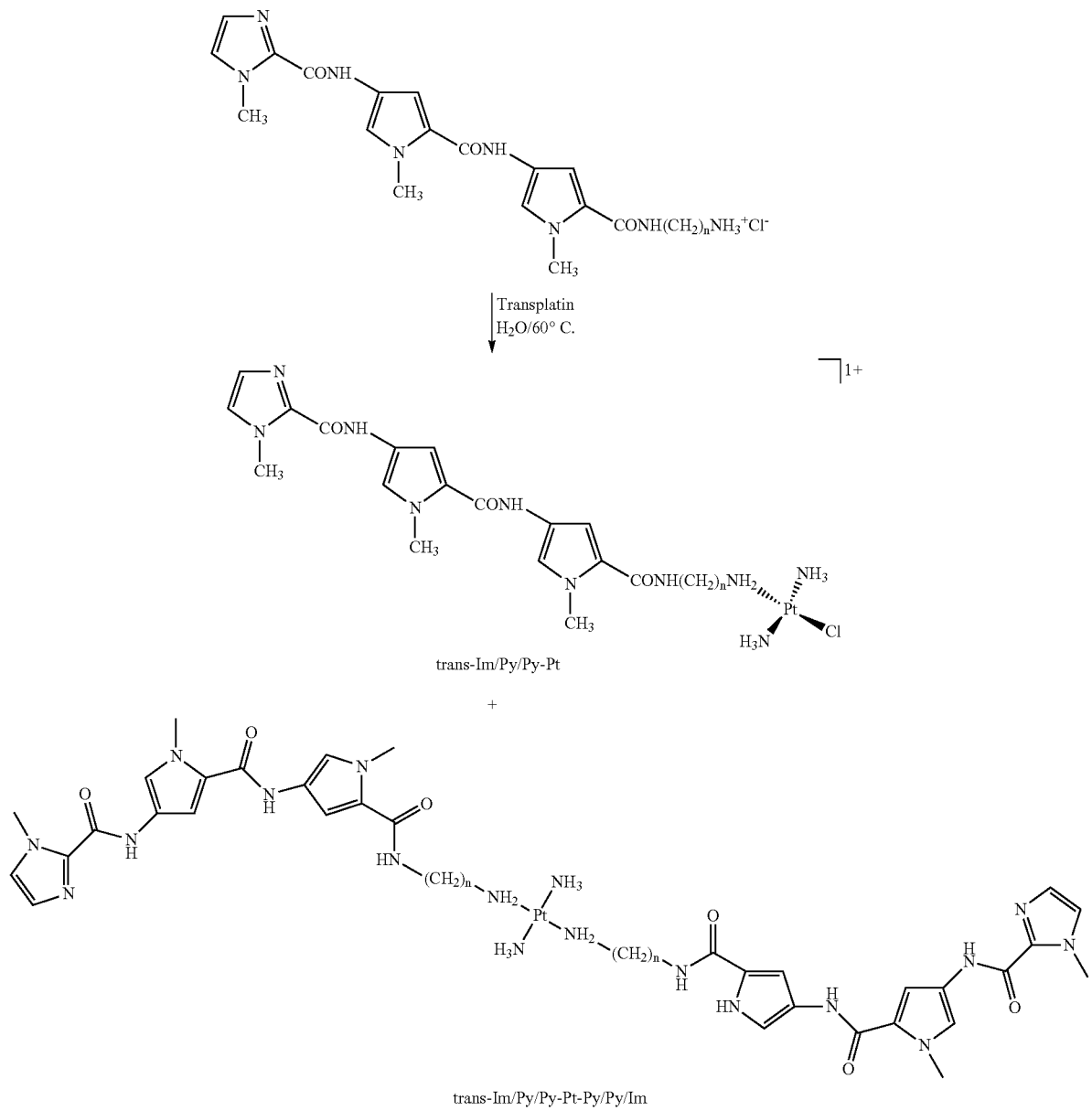

Example 2

DNA Melting Experiments

Figure 3A:
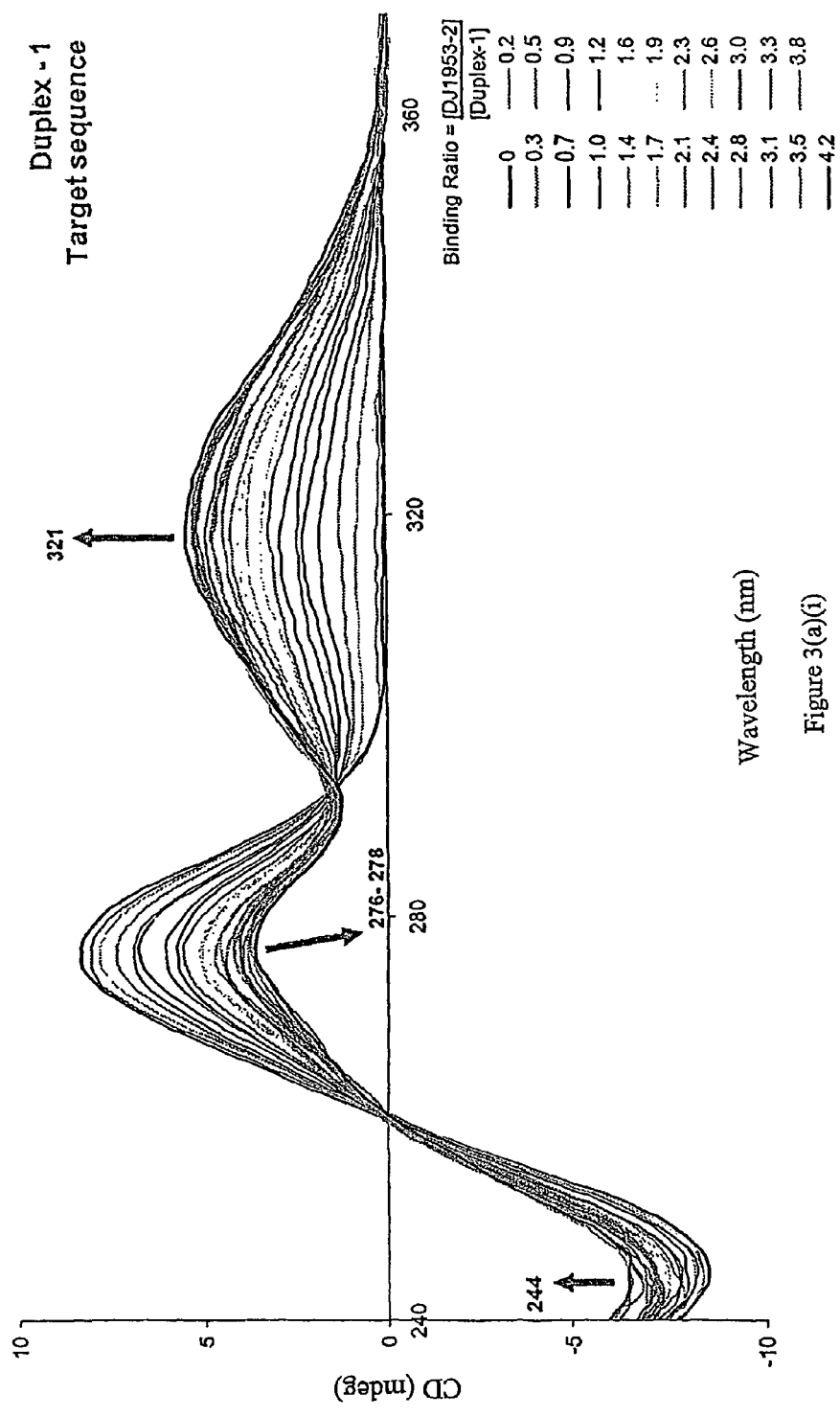
FIG. 3a—Circular Dichroism and Induced Circular Dichroism spectra (240 to 400 nm) at different concentration "trans-Im/Py/Py-[CONH(CH$_2$)$_2$—NH$_2$)Pt(NH$_3$)$_2$Cl" ("DJ1953-2"), into the three DNA duplexes; Duplex 1 (d(CATTGTCAGAC)$_2$—the target site); Duplex 2 (d(CATTGACAGAC)$_2$-single mismatch site) and Duplex 3 (d(CATTGAGAGAC)$_2$-double mismatch site). The data was normalised by subtracting the pure duplex spectrum in buffer.
Figure 3A:
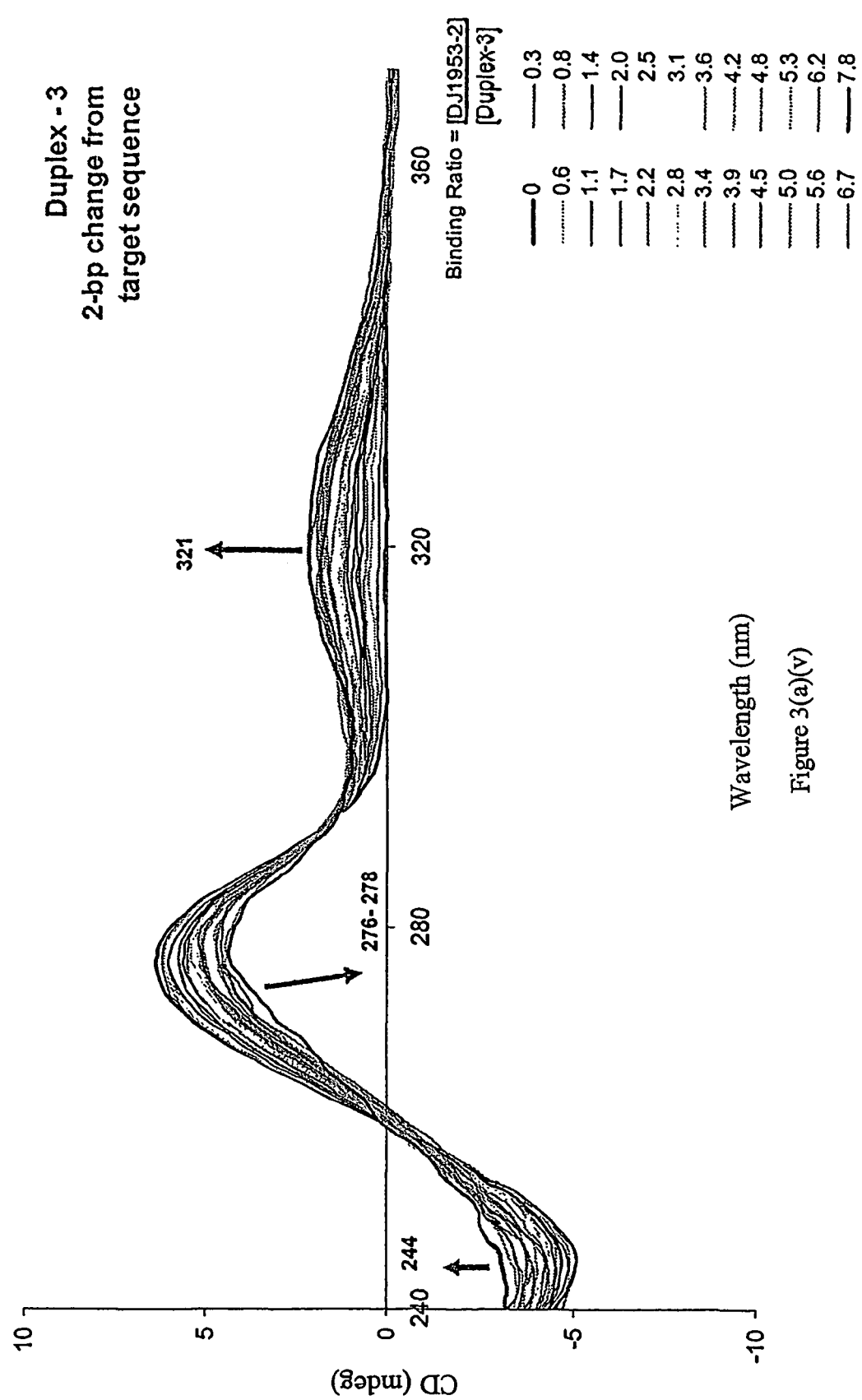
Figure 3B:
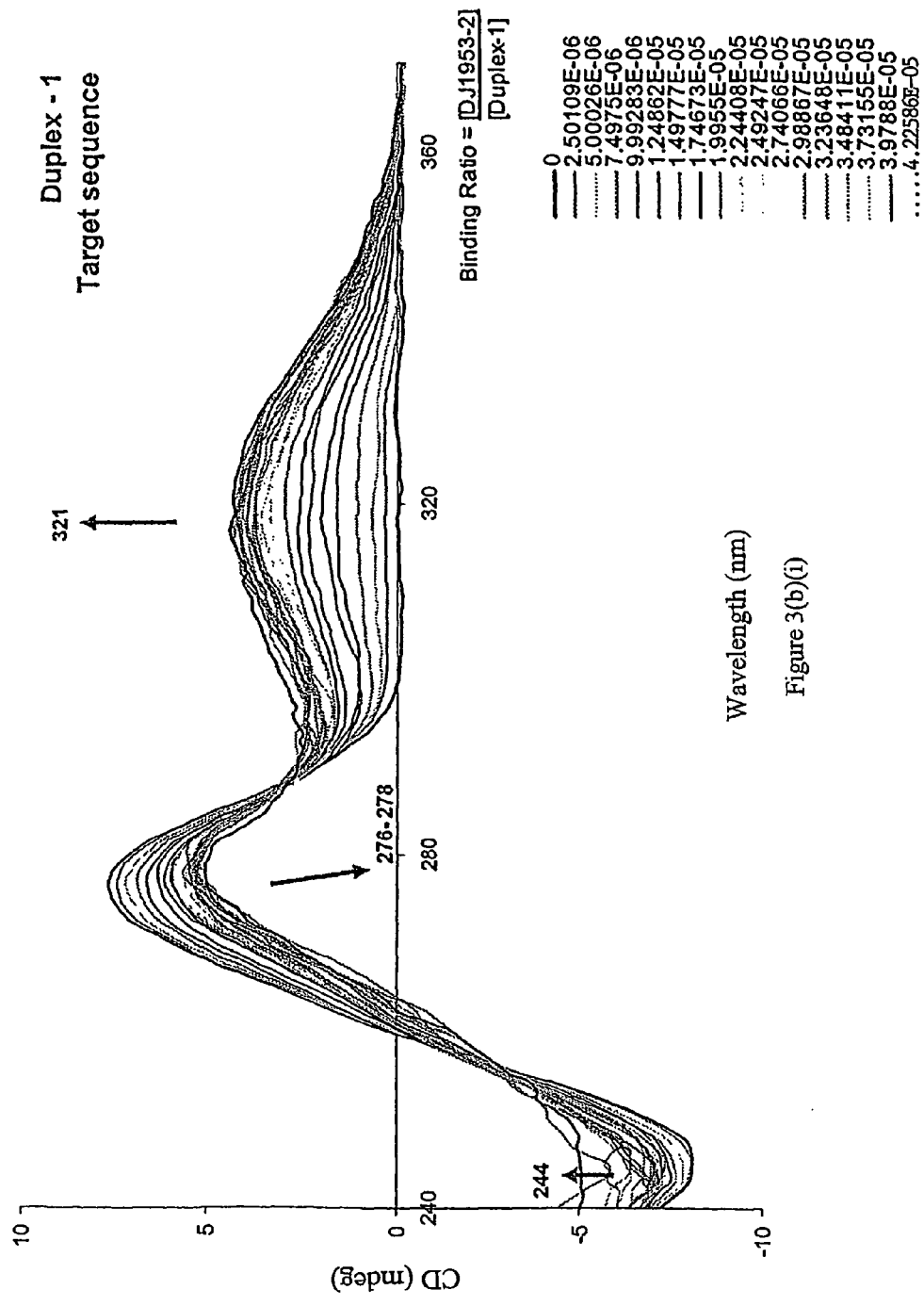
FIG. 3b—Circular Dichroism and Induced Circular Dichroism spectra (240 to 400 nm) at different concentration of "trans-Im/Py/Py-[CONH(CH$_2$)$_6$—NH$_2$)Pt(NH$_3$)$_2$Cl" ("DJ1953-6"), into the three DNA duplexes; Duplex 1 (d(CATTGTCAGAC)$_2$—the target site); Duplex 2 (d(CATTGACAGAC)$_2$-single mismatch site) and Duplex 3 (d(CATTGAGAGAC)$_2$-double mismatch site). The data was normalised by subtracting the pure duplex spectrum in buffer.
Figure 3B:
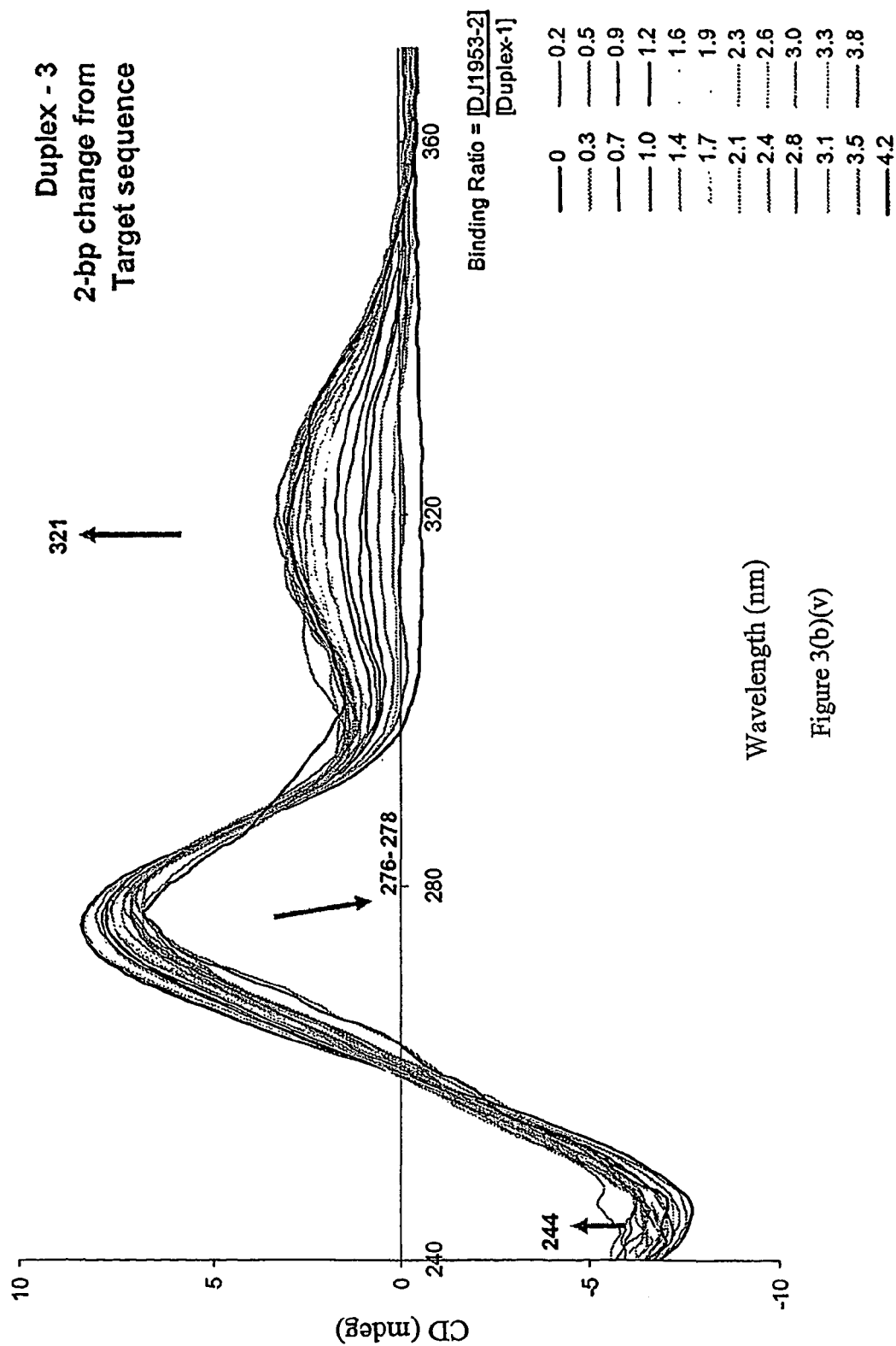
Figure 3C:
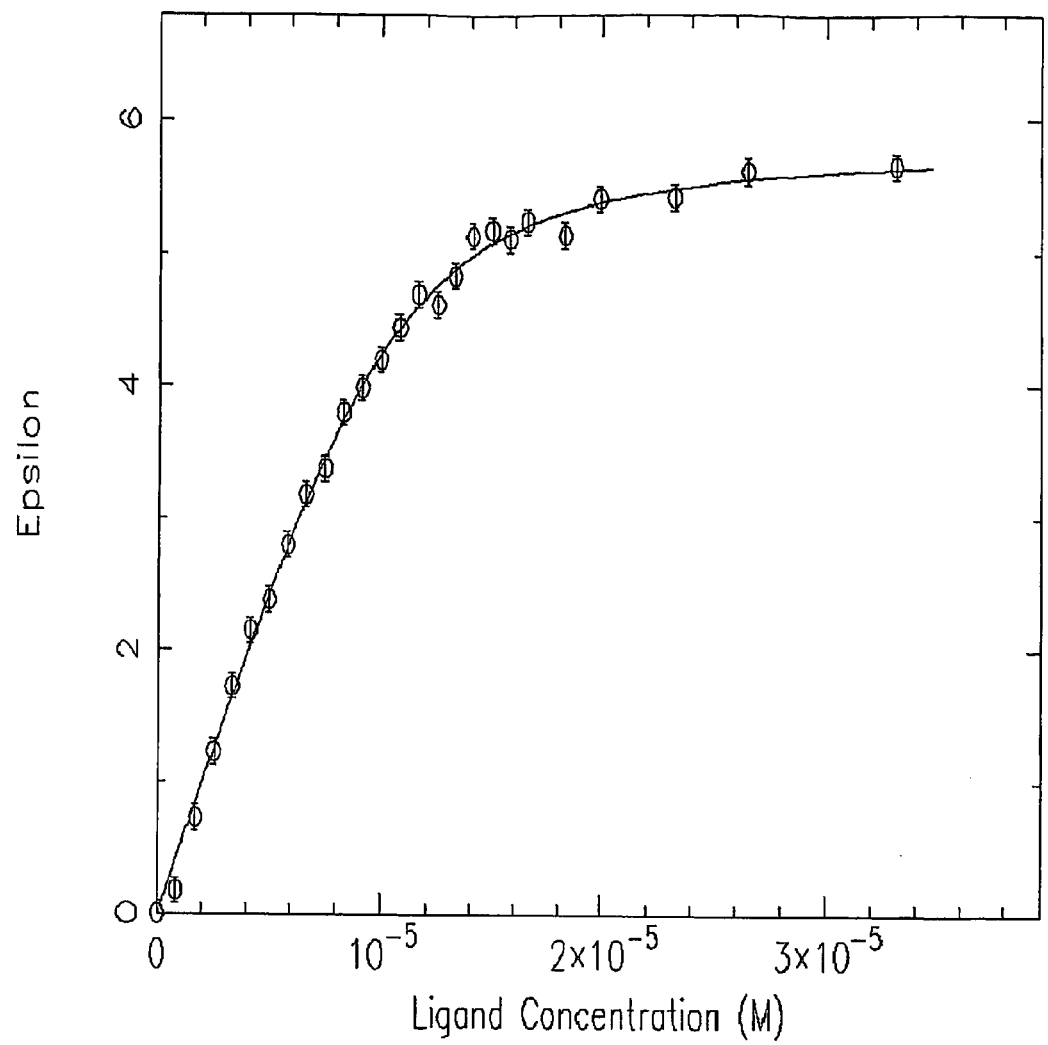
FIG. 3c—Titration data derived by taking a vertical cross section at 320 nm in Duplex 1 and "trans-Im/Py/Py-[CONH(CH$_2$)$_2$—NH$_2$)Pt(NH$_3$)$_2$Cl" ("DJ1953-2"), in FIG. 3a. The solid line is the theoretical fit of the data using least squares method. Calculated parameters averaged over 100 Monte Carlo simulations. All data was processed this way.

DNA melting profiles were acquired for Im/Py/Py-Pt at 260 nm using a Cary 1E recording spectrophotometer equipped with peltier controlled cell holder and cell length of quots of Im/Py/Py-Pt to a 2600 μL solution of 5 μM duplex DNA. After each addition, an average CD spectrum from 240 to 400 nm (20 accumulations) was recorded. DNA concentration was 5 μM. The concentration of Im/Py/Py-Pt ranged from 0 to 10 μM. Solution conditions were 10 mM sodium phosphate (pH 7.0) and 40 mM NaCl. CD spectra obtained are shown in FIGS. 3*a*-3*c* and Table 1

TABLE 1

| | apparent first-order affinity constant ($M^{-1}$) | | |
|---|---|---|---|
| | K for Binding Site | | |
| polyamide | d(CATTGTCAGAC)$_2$ | d(CATTGACAGAC)$_2$ | d(CATTGAGAGAC)$_2$ |
| DJ-1953-2 | $1.2 \times 10^6$ (0.1) | $5.6 \times 10^5$ (0.2) | $3.0 \times 10^5$ (0.1) |
| DJ-1953-6 | $2.4 \times 10^6$ (0.1) | $4.4 \times 10^5$ (0.2) | $1.3 \times 10^6$ (0.1) |

Derived from the CD titrations

Example 4

Unwinding Experiments

Figure 4:
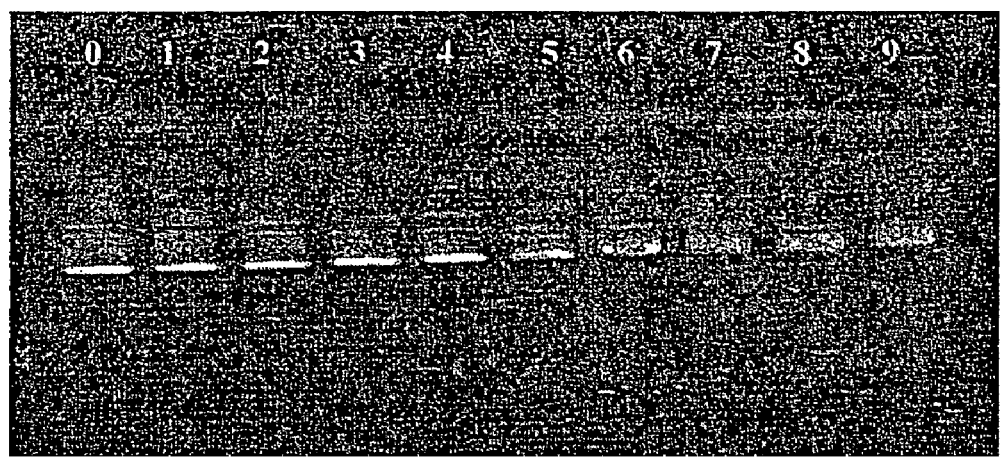
FIG. 4—Gel electrophoresis demonstrating binding of Im/Py/Py-Pt to a mixture of relaxed and negatively super-coiled pUC19 DNA. Lanes: 0 Control $r_b$=0; 1, $r_b$=0.008; 2, $r_b$=0. 0.016; 3, $r_b$=0.025; 4, $r_b$=0.033; 5, $r_b$=0.041; 6, $r_b$=0.049; 7, $r_b$=0.057; 8, $r_b$=0.066; 9, $r_b$=0.074.
Figure 5:
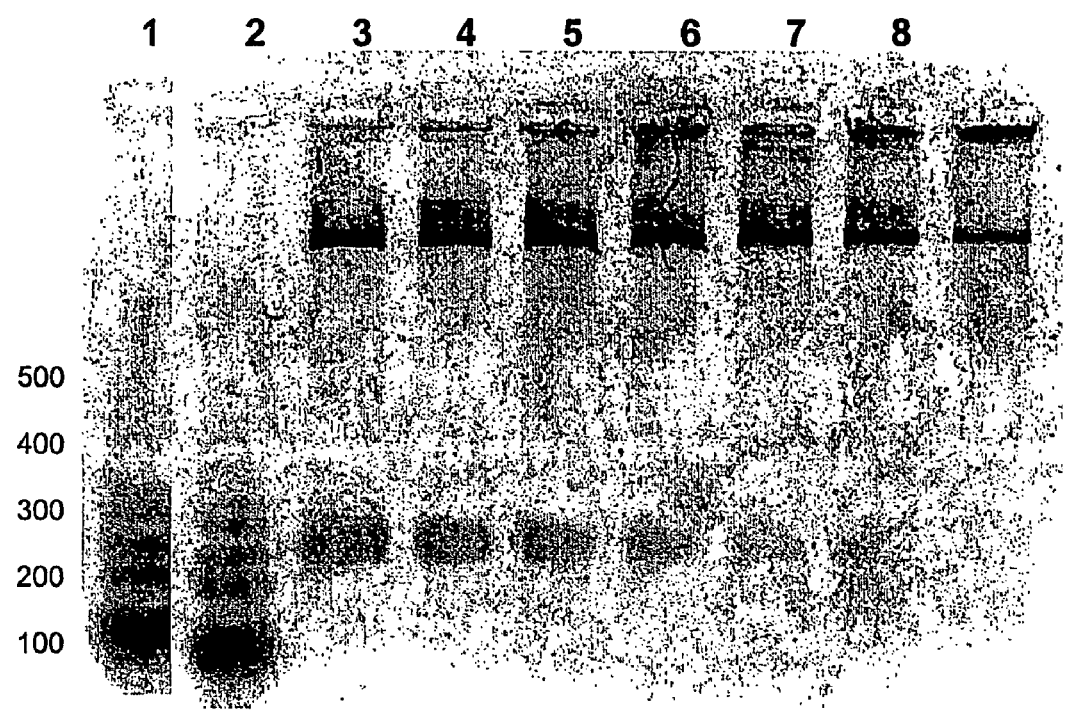
FIG. 5—In vitro Transcription Assay "trans-Im/Py/Py-[CONH(CH$_2$)$_2$—NH$_2$)Pt(NH$_3$)$_2$Cl" ("DJ1953-2") The Inhibition of RNA synthesis by DJ1953-2 was assessed using a recombinant pSP64 derivative. Incubations were carried out in 40 mM Tris-HCl (pH 7.9), 6 mM MgCl$_2$, 2 mM spermidine, 10 mM NaCl. Lane (1) 100-500 bases RNA marker; (2) to (8) increasing molar concentration of DJ1953-2. The inhibition of the full-length transcript (FLT) can be seen at 335 bases. Experiments were conducted after 12 hour platination reactions (in the dark at 4° C.).
Figure 6:
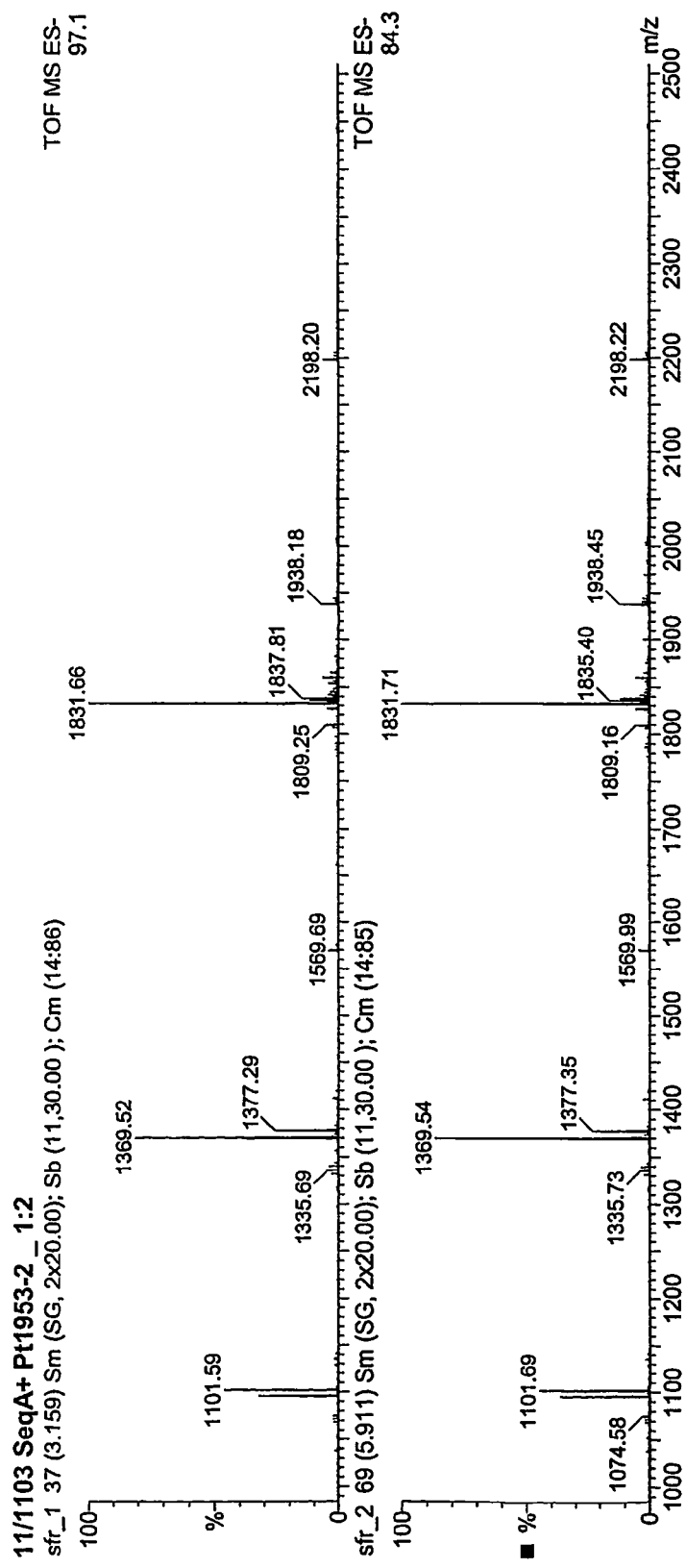
FIG. 6 ESI MS for "trans-Im/Py/Py-[CONH(CH$_2$)$_2$—NH$_2$)Pt(NH$_3$)$_2$Cl" ("DJ1953-2")
Figure 7:
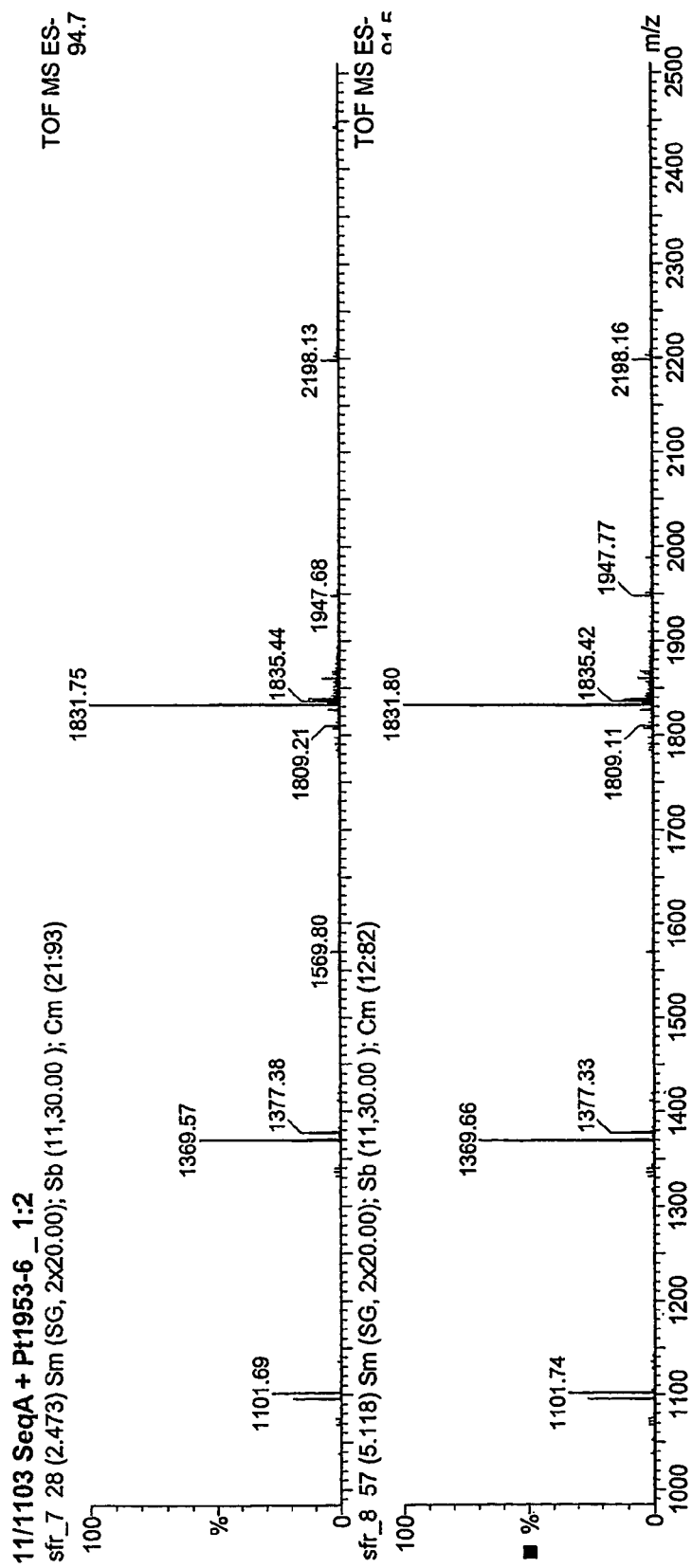
FIG. 7 ESI MS for "trans-Im/Py/Py-[CONH(CH$_2$)$_6$—NH$_2$)Pt(NH$_3$)$_2$Cl" ("DJ1953-6")

Gel electrophoresis indicates that variable amounts of Im/Py/Py-Pt have been bound to a mixture of relaxed and negatively supercoiled pUC19 DNA. The unwinding angle was determined to be 13° for this experiment, which is the same as that reported for cisplatin (13°). The plasmid was incubated with Im/Py/Py-Pt for 1.5 hr at 37° C. Lanes: 0 Control $r_b$=0; 1, $r_b$=0.008; 2, $r_b$=0.0016; 3, $r_b$=0.025; 4, $r_b$=0.033; 5, $r_b$=0.041; 6, $r_b$=0.049; 7, $r_b$=0.057; 8, $r_b$=0.066; 9, $r_b$=0.074. The top bands correspond to the form of nicked plasmid and the bottom bands to the closed, negatively supercoiled plasmid shown in FIG. 4.

Example 5

In Vitro Transcription Assay Using "trans-Im/Py/Py-[CONH(CH$_2$)$_2$—NH$_2$)Pt(NH$_3$)$_2$Cl" ("DJ1953-2")

The Inhibition of RNA synthesis by DJ1953-2 was assessed using a recombinant pSP64 derivative. Incubations were carried out in 40 mM Tris-HCl (pH 7.9), 6 mM MgCl$_2$, 2 mM spermidine, 10 mM NaCl. Lane (1) 100-500 bases RNA marker; Lanes (2) to (8) increasing molar concentration of DJ1953-2. The inhibition of the full-length transcript (FLT) can be seen at 335 bases. Experiments were conducted after 12 hour platination reactions (in the dark at 4° C.).

Example 6

ESIMS Binding Experiments

All mass spectra were acquired using a Micromass (Wyntheshaw, UK) Qtof 2 spectrometer with a Z-spray probe. Reactions were performed using solutions containing 25 micromolar duplex DNA and either 25 or 50 micromolar platinum complex. All reactions were performed in 0.1M ammonium acetate that had been adjusted to pH 8.5 Spectra were obtained ~4 hours after mixing. Samples were diluted with 0.1M ammonium acetate (pH 8.5) so that the final concentration of duplex was 10 micromolar, and then injected into the mass spectrometer using a Harvard model 22 syringe pump (Natick, Mass., USA) at a flow rate of 20 microlitre min$^{-1}$. Negative ion ESI mass spectra were acquired using a probe tip potential of 2500 V, a cone voltage of 50 V, and the source block and desolvation temperatures set to 60° C. and 80° C., respectively. The transport and aperture were set to 2.0 and 12.0, respectively. In most experiments spectra were acquired over the range m/z 500-3,000. Typically 50-70 scans were summed to obtain representative spectra. The data points were calibrated against a standard CsI solution (750 mM) over the same m/z range.

Example 7

Synthesis of ImImHpPy-γ-ImPyPyPy-(β-Ala)alkylamine

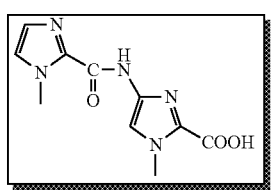

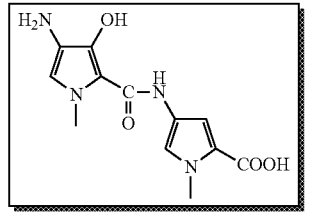

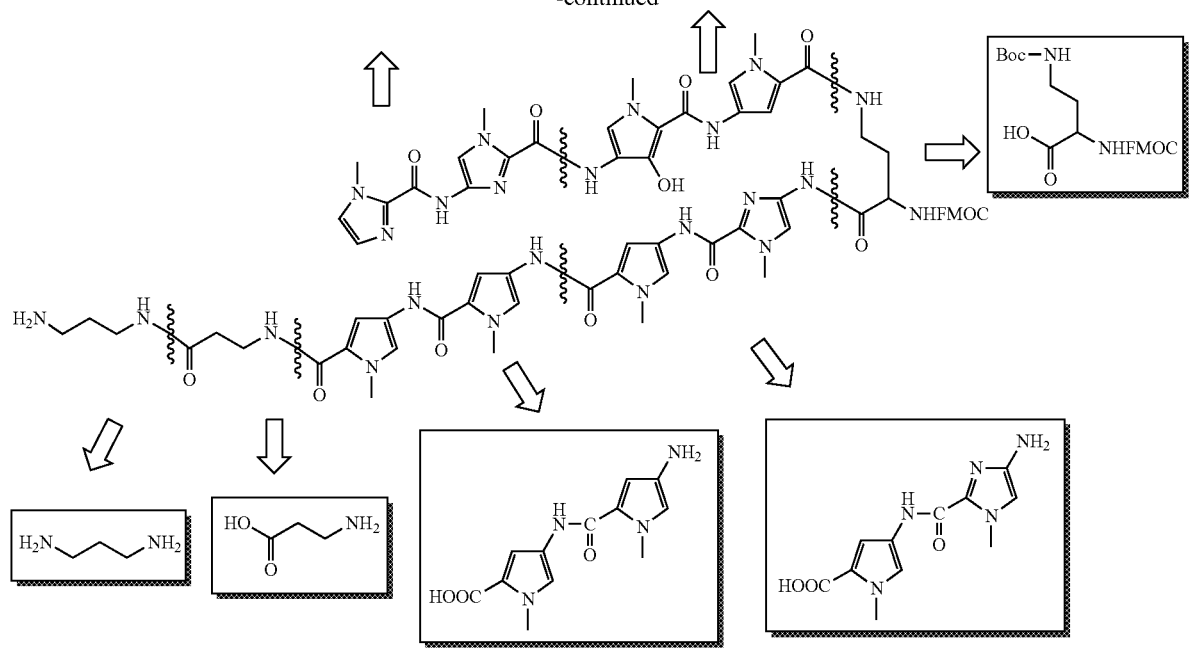

Retrosynthetic scheme for the synthesis of Synthesis of ImImHpPy-γ-ImPyPyPy-(β-Ala)alkylamine Methyl 4-[(tert-butoxycarbonyl)amino]-1-methylpyrrole-2-carboxylate (0.1415 g, 0.55 mmol) in 4 M HCl/EtOAc (4.26 ml) was stirred at room temperature for 30 min. The solvent was removed under reduced pressure and dried under vacuum for 1 hr. The residue was dissolved in DMF (4 ml) and EDCI (0.213 g, 1.11 mmol, 2 equiv), DMAP (0.135 g, 1.11 mmol, 2 equiv) and N-methylimidazole-2-carboxylic acid (0.105 g, 0.83 mmol, 1.5 equiv) were added and stirred overnight (19 hr). The solution was poured into EtOAc (25 ml) and washed with 10% HCl (3×25 ml), saturated NaHCO$_3$ (3×25 ml), the organics dried (Na$_2$SO$_4$) and concentrated under vacuum.

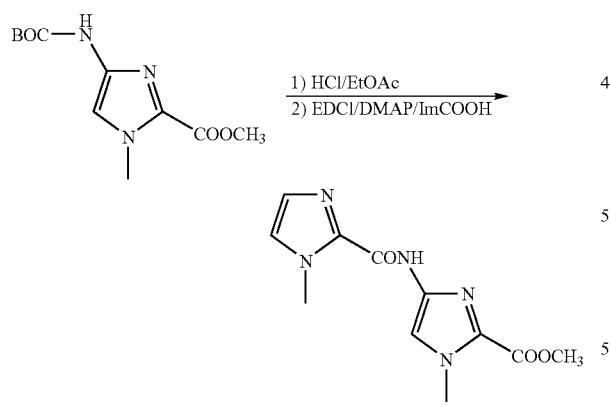

Methyl 4-[(tert-butoxycarbonyl)amino]-1-methylpyrrole-2-carboxylate (0.1108 g, 0.43 mmol) in 4 M HCl/EtOAc (4.26 ml) was stirred at room temperature for 30 min. The solvent was removed under reduced pressure and dried under vacuum for 1 hr. The residue was dissolved in DMF (4 ml) and ImCOOH (0.059 g, 0.52 mmol, 1.2 equiv) was added followed by HOBt (0.079 g, 0.65 mmol, 1.5 equiv), TBTU (0.189 g, 0.65 mmol) and Et$_3$N (0.328 ml, 2.6 mmol, 6 equiv) and the solution stirred for 1 hr. Solvent was removed and purified by flash chromatography (0-5% MeOH/DCM).

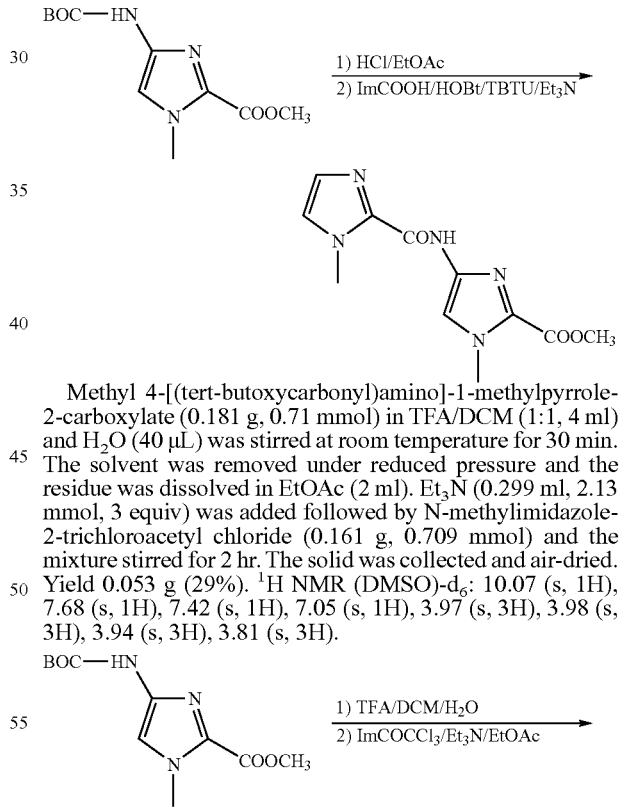

Methyl 4-[(tert-butoxycarbonyl)amino]-1-methylpyrrole-2-carboxylate (0.181 g, 0.71 mmol) in TFA/DCM (1:1, 4 ml) and H$_2$O (40 μL) was stirred at room temperature for 30 min. The solvent was removed under reduced pressure and the residue was dissolved in EtOAc (2 ml). Et$_3$N (0.299 ml, 2.13 mmol, 3 equiv) was added followed by N-methylimidazole-2-trichloroacetyl chloride (0.161 g, 0.709 mmol) and the mixture stirred for 2 hr. The solid was collected and air-dried. Yield 0.053 g (29%). $^1$H NMR (DMSO)-d$_6$: 10.07 (s, 1H), 7.68 (s, 1H), 7.42 (s, 1H), 7.05 (s, 1H), 3.97 (s, 3H), 3.98 (s, 3H), 3.94 (s, 3H), 3.81 (s, 3H).

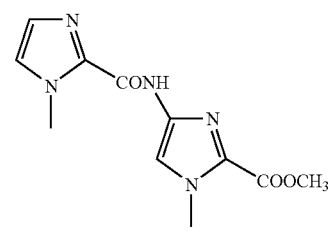

Example 8

Retrosynthetic Scheme for the Synthesis of "Pt(NH$_2$(CH$_2$)$_6$NHCO]ImImIm-[γ-[NHCO(CH$_2$)$_7$NH$_2$]Pt]-PyPyPy"

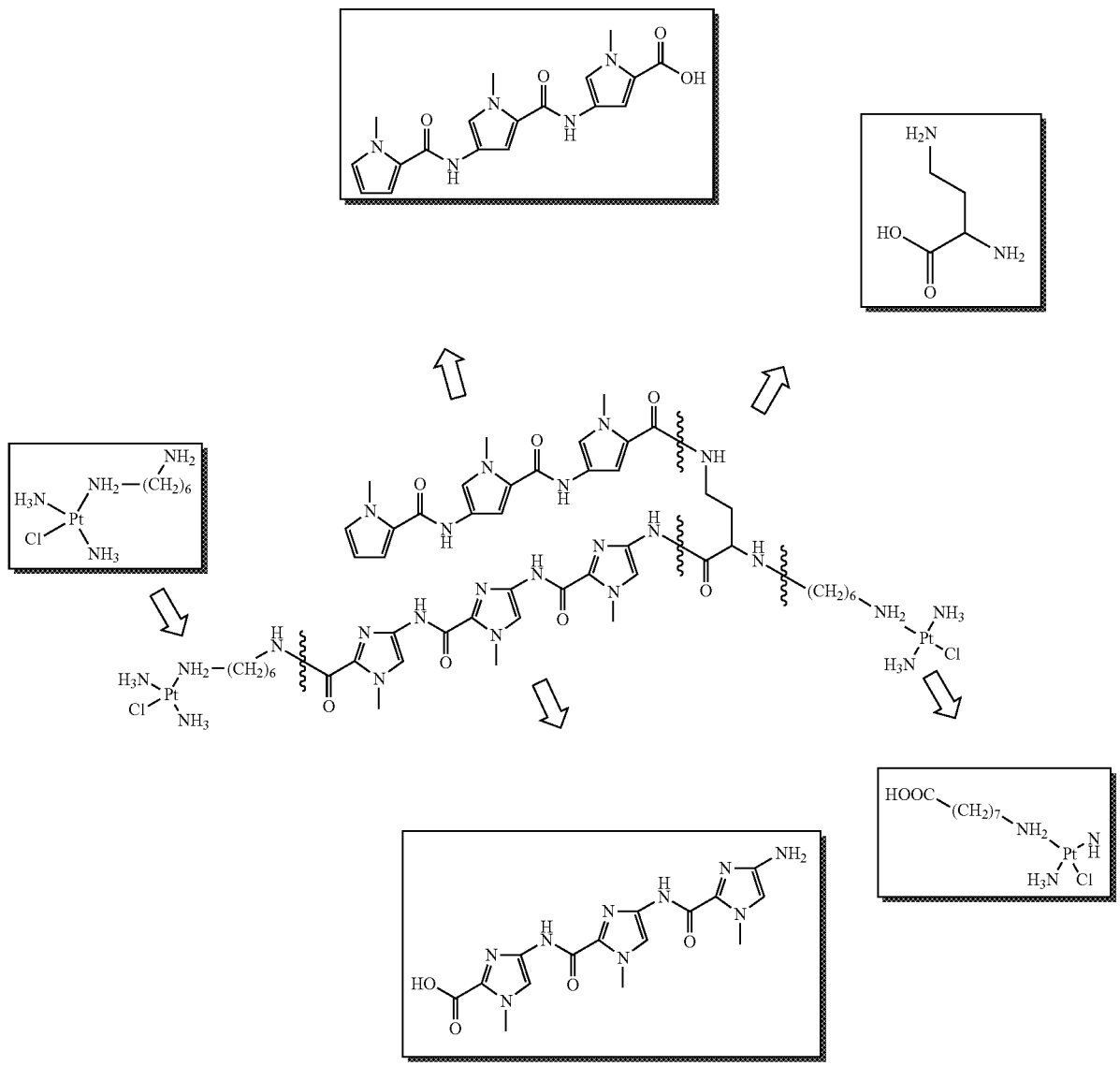

Ethyl 1-methylimidazole-2-carboxylate (Im-1)

To a solution of N-methylimidazole (5 g, 0.06 mol), acetonitrile (32 mL) and triethylamine (15 mL), cooled to −20° C. was added ethyl chloroformate (13 mL, 0.137 mol), and the mixture allowed to slowly warm to room temperature and stirred for 3.5 hr. The solution was filtered (triethylamine hydrochloride) and concentrated under vacuum. The residue was purified by distillation under reduced pressure (0 Torr, 102° C.) to yield the product as a white solid. Yield (6.26 g, 68%) $^1$H NMR (DMSO): δ 7.44 (d, 1H, J=2.8 Hz), 7.04 (d, 1H, J=2.8 Hz), 4.26 (q, 2H, J=3.5 Hz), 3.91 (s, 3H), 1.26 (t, 3 h, J=3.5 Hz). $^{13}$C (DMSO): 159.3, 129.1, 127.7, 61.0, 36.0, 14.5.

Ethyl 1-methyl-4-nitroimidazole-2-carboxylate (Im-2)

Im-1 (1.8 g) was dissolved in concentrated H$_2$SO$_4$ (5 mL) and cooled to 0° C. Nitric acid (90%, 5 mL) was slowly added and the solution warmed to room temperature and then refluxed at −20° C. for 1.5 hr. The reaction was quenched by pouring onto ice (50 mL). The resulting blue solution was extracted with DCM, dried over sodium sulphate, and evaporated under vacuum to yield a tanned and oily product. The residue was precipitated with CCl$_4$:EtOH (1:1, 5 mL) to yield the product as white crystals. Yield (1.0543 g, 45%). $^1$H NMR (DMSO): δ 8.61 (s, 1H), 4.33 (q, 2H, J=6.4 Hz), 3.97 (s, 3H), 1.29 (t, 3H, J=6.0 Hz). $^{13}$C (DMSO): 158.2, 145.4, 135.3, 127.4, 62.2, 37.3, 14.5.

Ethyl 4-amino-1-methylimidazole-2-carboxylate (Im-3)

Im-2 (0.4 g) in EtOH/ethyl acetate (1:1, 14 mL) and Pd/C (10%, 0.3 g) were stirred under a slight positive pressure of hydrogen (ca 1.1 atm) for 3-4 hr. The reaction mixture was filtered using celite and solvent evaporated on the rotary. The remaining solid was freeze dried to yield a slightly yellow product. Yield (0.38 g, 95%). $^1$H NMR (DMSO): δ 6.45 (s, 1H), 4.5 (bs, 2H, NH$_2$), 4.2 (q, 2H, J=7 Hz), 3.76 (s, 3H), 1.24 (t, 3H, J=7.9 Hz).

[(tert-Butoxycarbonyl)amino]-1-methylimidazole-2-carboxylic acid (Im-4)

To Im-3 (0.38 g) in DMF (8 mL) and Hunig's base (2 mL) was added ditert-butyl dicarbonate (0.7 ml) and the mixture stirred at 60° C. for 3 hr. It was then cooled to room temperature and brine (6 mL) and ethyl ether (6 mL) were added. The ether layer was extracted with 10% citric acid, brine, saturated sodium bicarbonate, and brine (10 mL each). The ether layer was then dried over sodium sulfate and evaporated under vacuum. NaOH (1M, 5 mL) in methanol was then added and solution stirred at 60° C. for 1 hr. The mixture was then cooled to 0° C. and neutralised with 1M HCl to pH 2 at which a white gel was formed. The gel was collected by gravity filtration and washed with water pH=6 before it was freeze dried to yield the product as a white powder. Yield (0.41 g, 76%). $^1$H NMR (DMSO): δ 9.45 (bs, 1H, NH), 7.21 (bs, 1H), 3.86 (s, 3H), 3.67 (bs, 1H, OH), 1.4 (s, 9H).

Ethyl-1-Methyl-4[((4-tert-butoxycarbonyl)amino-1-methyl-1H-imidazole-2-carbonyl)-amino]-1H-imidazole-2-carboxylate (ImImCOOCH$_2$CH$_3$)

NO$_2$ImCOOCH$_2$CH$_3$ (0.1 g, 0.5912 mmol) was dissolved in ethanol:ethylacetate (1:1, 8 mL) and Pd/C (10%, 0.015 g) and then stirred under H$_2$ (1 atm) for 2.5 hr (TLC (Silica Gel 60 F$_{254}$ precoated plated Merck)-2% MeOH/DCM). The catalyst was filtered, DMF (3 mL) added and ethanol was evaporated. Im-4 (0.15 g, 0.64 mmol) was added followed by HOBT (0.11 g, 0.815 mmol), TBTU (0.262 g, 0.815 mmol), Et$_3$N (0.38 mL, 2.71 mmol) and the solution stirred for 3 hr. The solid was filtered, DMF evaporated and the residue was purified using column chromatography (7% MeOH/DCM) yielding the product as a creamy solid. Yield (0.13 g, 66%). $^1$H NMR (DMSO): δ 9.6 (bs, 1H, NH), 9.5 (bs, 1H, NH), 7.61 (s, H), 7.22 (bs, 1H), 4.2 (q, 2H, J=7.2 Hz), 3.91 (s, 6H), 1.45 (s, 9H), 1.28 (t, 3H, J=7.3 Hz).

1-Methyl-4-[((4-tert-butoxycarbonyl)amino-1-methyl-1H-imidazole-2-carbonyl)-amino]-1H-imidazole-2-carboxylic acid (ImImCOOH)

ImImCOOCH$_2$CH$_3$ (0.15 g) was dissolved in MeOH (10 mL) and NaOH/MeOH (1 M, 10 mL). The solution was stirred for 0.5 hr. at 60° C. and monitored by (Silica Gel 60 F$_{254}$ precoated plated Merck) (7% MeOH/DCM). The solution was then cooled to 0° C. before it was neutralised using HCl (1 M) to pH=2. The product was filtered to obtain a pink solid. Yield (0.13 g, 93.5%). $^1$H NMR (DMSO): δ 9.45 (bs, 2H, 2NH), 7.69 (s, 1H), 7.22 (bs, 1H), 3.91 (s, 6H), 3.41 (b, OH), 1.43 (s, 9H).

Ethyl-1-Methyl-4-({1-methyl-4-[((4-tert-butoxycarbonyl)amino-1-methyl-1H-imidazole-2-carbonyl)-amino]-1H-imidazole-2-carbonyl}-amino)-1H-imidazole-2-carboxylate (ImImImCOOCH$_2$CH$_3$)

NO$_2$ImCOOCH$_2$CH$_3$ (0.09 g, 0.532 mmol) was dissolved in ethanol:ethyl acetate (1:1, 8 mL) and Pd/C (10%, 0.025 g) and then stirred under H$_2$ (1 atm) for 2 hr. (TLC (Silica Gel 60 F$_{254}$ precoated plated Merck)-2% MeOH/DCM). The catalyst was filtered, DMF (10 mL) added and ethanol was evaporated. ImIm-OH (0.15 g, 0.412 mmol) was added followed by HOBT (0.083 g, 0.6 mmol), TBTU (0.19 g, 0.6 mmol), Et$_3$N (0.5 mL, 2.5 mmol) and the solution stirred for 2 hr. The solid was filtered, DMF was evaporated and the residue was purified twice using column chromatography yielding the product as a creamy solid. Yield (0.084 g, 72%). $^1$H NMR (DMSO): δ 10.01 (s, 1H, NH), 9.58 (bs, 1H, NH), 9.35 (s, 1H, NH), 7.64 (s, 1H), 7.6 (s, 1H), 7.22 (bs, 1H), 4.29 (q, 2H, J=7.3 Hz), 3.98 (s, 3H), 3.96 (s, 3H), 3.93 (s, 3H), 1.45 (s, 9H), 1.3 (t, 3H, J=7.1 Hz).

1-Methyl-4-({1-methyl-4-[((4-tert-butoxycarbonyl)amino-1-methyl-1H-imidazole-2-carbonyl)-amino]-1H-imidazole-2-carbonyl}-amino)-1H-imidazole-2-carboxylic acid (ImImImCOOH)

ImImImCOOCH$_2$CH$_3$ (0.14 g) was dissolved in THF/MeOH (1:1, 2 mL) and LiOH (1 M, 2 mL). The solution was stirred for 0.5 hr. at 55° C. and monitored by TLC ((Silica Gel 60 F$_{254}$ precoated plated Merck) 7% MeOH/DCM). The solution was then cooled to 0° C. before it was neutralised using HCl (1 M) to pH=4. The product was filtered to obtain a pink solid. Yield (0.11 g, 83%). $^1$H NMR (DMSO): δ 10.01 (bs, 1H, NH), 9.45 (bs, 2H, 2NH), 7.60 (s, 1H), 7.59 (s, 1H), 7.23 (bs, 1H), 3.98 (s, 3H), 3.95 (s, 3H), 3.91 (s, 3H), 3.56 (bs, 1H, OH), 1.44 (s, 9H).

Synthesis of the Triple Pyrrole Polyamide ("PyPyPy")

Methyl-4-nitropyrrole-2-carboxylic acid (Py-1)

Acetic anhydride (8 mL) was treated with 70% nitric acid (1.6 mL) and the mixture heated to 50° C. for 15 minutes, then cooled to room temperature, and slowly added to a suspension of 1-methyl-2-pyrrolecarboxylic acid (2 g) in Ac$_2$O (12 mL) and cooled to −25° C. The mixture was stirred at −15° C. for 0.5 hr, then the temperature was allowed to rise to ambient, and stirring was continued for 20 min. The mixture was again cooled to −25° C. and the resulting precipitate was collected in a funnel cooled on dry ice. The solid was washed with a small amount of cold Ac$_2$O (−25° C.), and then dissolved in 1M NaOH solution. Acidification with 1M HCl precipitated the compound. Yield (0.77 g, 28%). $^1$H NMR (DMSO): δ 8.19 (d, 1H, J=1.8 Hz); 7.23 (d, 1H, J=2.0 Hz); 3.90 (s, 3H).

Methyl-4-nitropyrrole-2-carboxylate (Py-2)

A solution of H$_2$SO$_4$ (0.8 mL) in MeOH (8 mL) was added to Py-1 (0.77 g, 4.53 mmol) and the mixture heated at reflux for 24 hr. Water was added and the mixture extracted with DCM. The organic solvent was dried using MgSO$_4$, and solvent evaporated under vacuum to yield the product as a crystalline solid. Yield 0.55 g, 66%). $^1$H NMR (DMSO): δ 7.57 (d, 1H, J=2.1 Hz); 7.40 (d, 1H, J=2.0 Hz); 3.99 (s, 3H); 3.86 (s, 3H).

Methyl-1-methyl-4-[(1-methyl-1H-pyrrole-2-carbonyl)-amino]-1H-pyrrole-2-carboxylate (PyPyCOOCH$_3$)

NO$_2$PyCOOCH$_3$ (0.2 g, 1.086 mmol) in MeOH (60 mL) and Pd/C (10%, 0.04 g) were stirred under H$_2$ (1 atm) for 1 hr (TLC-(Silica Gel 60 F$_{254}$ precoated plated Merck) 5% MeOH in DCM). The catalyst was removed using celite, DMF (3 mL) was added and MeOH was evaporated. 1-Methylpyrrole-2-carboxylic acid (0.162 g, 1.3 mmol) was added followed by HOBT (0.22 g, 1.63 mmol), TBTU (0.524 g, 1.63 mmol), Et$_3$N (0.76 mL, 5.42 mmol) and the solution stirred for 1 hr. DMF was evaporated under pressure and product was purified by column chromatography (5% MeOH/DCM) affording the product as a creamy yellow solid. Yield (0.4 g). $^1$H NMR (DMSO): δ 9.6 (bs, 1H, NH), 7.98 (s, 2H), 7.88 (d, 1H, J=2.1 Hz), 7.34 (d, 1H, J=2 Hz), 6.93 (bs, 1H), 3.92 (s, 3H), 3.89 (s, 3H), 3.79 (s, 3H).

1-Methyl-4-[(1-methyl-1H-pyrrole-2-carbonyl)-amino]-1H-pyrrole-2-carboxylic acid (PyPyCOOH)

PyPyCOOCH$_3$ (0.403 g, 1.5 mmol) was dissolved in THF/MeOH (1:1, 6 mL). 1M LiOH (6 mL) was added and stirred at 60° C. for 1.5 hr. The organics were evaporated under vacuum, solution was cooled and acidified with 1M HCl to pH=3. The solid was collected and air-dried. Yield (0.35 g, 92%). $^1$H NMR (DMSO): δ 9.75 (s, 1H, NH), 7.4 (s, 1H), 6.95 (s, 1H,), 6.9 (bs, 1H), 6.8 (bs, 1H), 6.05 (bs, 1H), 3.83 (s, 3H), 3.81 (s, 3H), 3.3 (bs, 1H, OH).

Methyl-1-methyl-4-({1-methyl-4-[(1-methyl-1H-pyrrole-2-carbonyl)-amino]-1H-pyrrole-2-carbonyl}-amino)-1H-pyrrole-2-carboxylate (PyPyPy-COOCH$_3$)

NO$_2$PyCOOCH$_3$ (0.116 g, 0.63 mmol) in MeOH (50 mL) and Pd/C (10%, 0.04 g) were stirred under H$_2$ (1 atm) for 1 hr ((Silica Gel 60 F$_{254}$ precoated plated Merck)-5% MeOH/DCM). The catalyst was filtered using celite, DMF (4 ml) was added, and solvent evaporated. PyPyCOOH (0.1 g, 0.42 mmol) was added followed by HOBT (0.09 g, 0.69 mmol), TBTU (0.22 g, 0.69 mmol), Et$_3$N (0.6 mL, 5.1 mmol) and the solution was stirred for 1 hr. The solvent was evaporated and the residue was purified by column chromatography (5% MeOH/DCM). Yield (0.21 g, 84%). $^1$H NMR (CD$_3$OD): δ 8.0 (s, 1H), 7.35 (bs, 1H), 7.2 (bs, 1H), 6.9 (bs, 1H), 6.85 (bs, 1H), 6.1 (bs, 1H), 5.5 (bs, 1H), 3.9 (s, 6H), 3.8 (s, 3H), 3.4 (s, 3H).

1-Methyl-4-({1-methyl-4-[(1-methyl-1H-pyrrole-2-carbonyl)-amino]-1H-pyrrole-2-carbonyl}-amino)-1H-pyrrole-2-carboxylic acid (PyPyPyCOOH)

PyPyPyCOOCH$_3$ (0.148 g) was dissolved in THF/MeOH (1:1, 3 mL), LiOH (1M, 3 mL) was added and solution stirred at 60° C. for 1.5 hr. The organics were evaporated, solution then cooled on ice and acidified to pH=3 using HCl (1 M). The solid was filtered. Yield (0.07 g, 49%). $^1$H NMR (DMSO): δ 9.85 (s, 1H, NH), 9.82 (s, 1H, NH), 7.4 (s, 1H), 7.2 (s, 1H), 7.0 (s, 1H), 6.9 (bs, 2H), 6.8 (bs, 1H), 6 (bs, 1H), 3.83 (s, 3H), 3.82 (s, 3H), 3.81 (s, 3H), 3.23 (b, 1H, OH).

Synthesis of the PtCl(NH$_3$)$_2$(C$_6$H$_{12}$[NH$_2$][NHBoc])

tert-Butoxycarbonyl)amino-6-amino-hexane

A solution of di-tert-butyl dicarbonate (3 g, 0.014 moles) in DCM (12 mL) was added over a period of 2 hr. to a solution of 1,6-diaminohexane (12 g, 0.11 moles) in DCM (36 mL) that was cooled to −10° C. The mixture was stirred for 24 hrs. before the solvent was removed under vacuum. Water (60 mL) was added to the residue and the insoluble bis-substituted product was collected by filtration. The filtrate was extracted using DCM (3×60 mL) and then dried over Na$_2$SO$_4$ before the solvent was evaporated. The residue was dissolved in chloroform and any undissolved product was filtered. The filtrate was then evaporated under vacuum to yield the product as a slightly yellow oil. Yield (4.12 g, 55.3%). $^1$H NMR (CDCl$_3$): 9.8 (bs, 1H, NH), 4.45 (bs, 2H, NH$_2$), 3 (b, 4H), 2.6 (b, 4H), 2.15 (b, 4H), 1.25 (s, 9H).

Purification of Transplatin, trans Pt(NH$_3$)$_2$Cl$_2$

Impure transplatin (2 g) was mixed with water (300 mL, pH=5) and stirred at 100° C. until the solution became clear. The solution was quickly filtered and the filtrate was cooled for 1 hr. The resulting precipitate was filtered to yield the product as a yellow solid. Yield (0.8 g, 40%). $^1$H NMR (CDCl$_3$): δ 4.35 (b, 6H).

PtCl(NH$_3$)$_2$(C$_6$H$_{12}$[NH$_2$][NHBoc])

Transplatin (0.05 g, 0.17 mmol) and 1-tert-butoxycarbonyl)amino-6-amino-hexane (0.036 g, 0.17 mmol) in water (23 mL) were refluxed at 60° C. until the mixture dissolved (24 hr.). The solution was cooled and filtered through 0.45 μm pores before the water was evaporated to yield a creamy white solid. Yield (0.072 g, 91%).

Attaching the Fmoc-L-2,4-Diaminobutyric acid(Boc) Linker to the Imidazole Polyamide ImImIm-OH (0.05 g, 0.105 mmol) was dissolved in DCM (5 mL). Trifluoro acetic acid/DCM (1:1, 6 mL) was added and the solution stirred under N$_2$ atm for 1 hr and monitored through TLC ((Silica Gel 60 F$_{254}$ precoated plated Merck) 10% H$_2$O/ACN). The solvent was evaporated and a solution of Fmoc-L-2,4-Diaminobutyric acid(Boc) (0.046 g, 0.105 mmol) in DMF (5 mL) was added followed by HOBT (0.02 g, 0.15 mmol), TBTU (0.048 g, 0.15 mmol), and Et$_3$N (0.1 mL, 0.5 mmol). The mixture was stirred under N$_2$ atm for 2-3 hr. and then purified by column chromatography (7% MeOH/DCM) before the solvent was evaporated to yield a white creamy solid.

Example 9

Retrosynthetic scheme for the synthesis of PyPy-PyPy-[(O-phen)Ru(bpy)$_2$]Cl$_2$

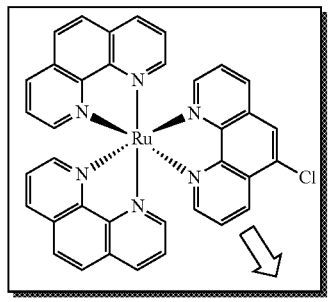

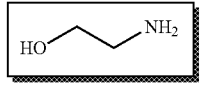

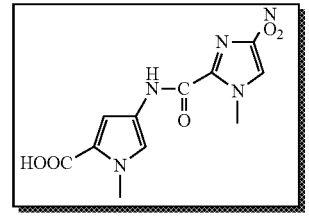

-continued

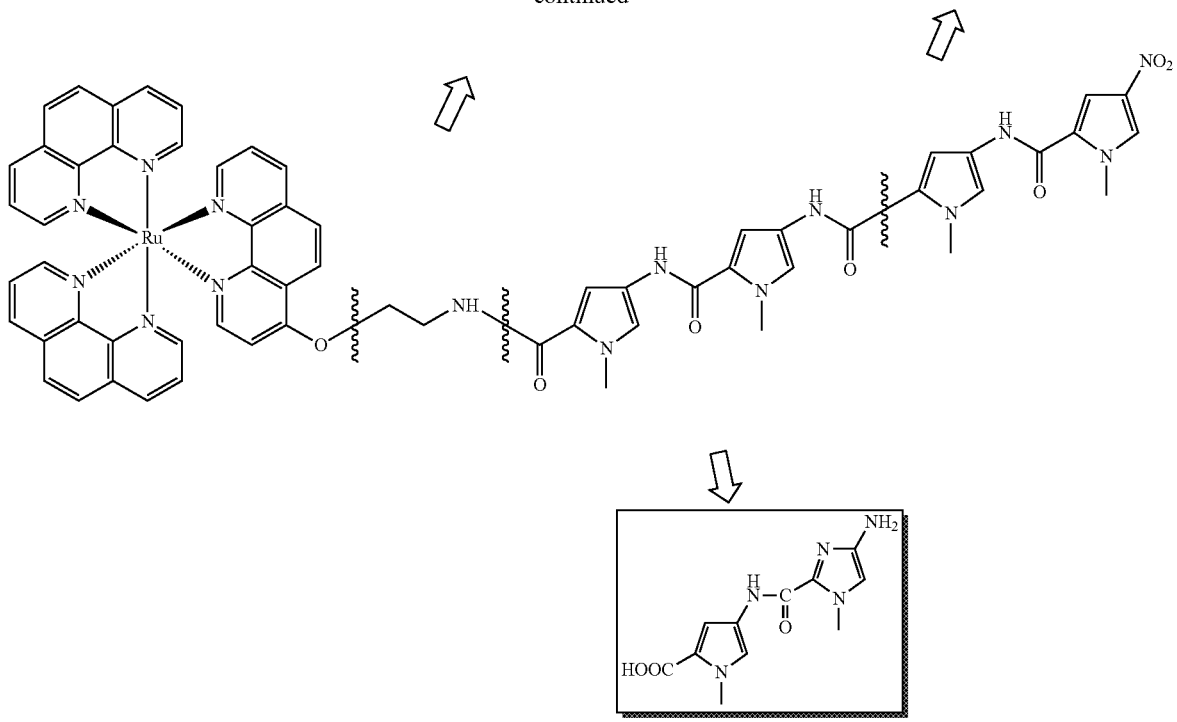

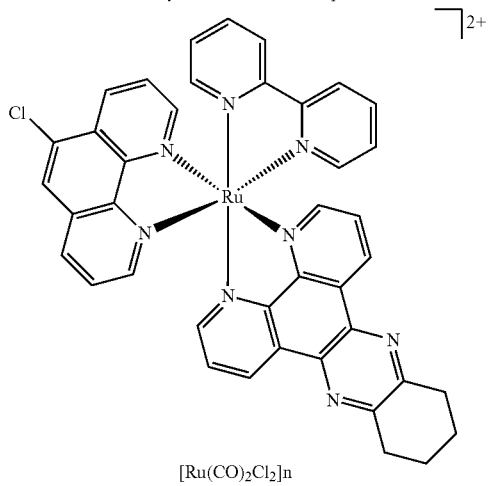

Synthesis of metal complexes

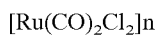

[Ru(CO)₂Cl₂]ₙ

Paraformaldehyde (3 g) and RuCl₃·3H₂O (6 g, 22.9 mmol) were added to a dry nitrogen sparged solution of 90% formic acid (150 mL). The solution was heated at reflux for 6 hr then left at 0° C. overnight. The solution was evaporated slowly over a steam bath and triturated from hexane. The product was then filtered and dried in vacuo. Yield: 1.88 g, 36%.

[Ru(bpy)(CO)₂Cl₂]

2,2'-Bipyridyl (bpy, 1.03 g, 6.6 m mol) was added to methanol (10 mL), vigorous stirring and deaerated with dry nitrogen for 30 min. [Ru(CO)₂Cl₂]ₙ (1.0 g, 4.4 mmol) was added followed by refluxing for 30 min. Extra methanol (20 mL) was added 15 min into the reflux. The product was then cooled to room temperature, collected and recrystallised from methanol. Yield: 0.78 g, 46%.

[Ru(bpy)(CO)₂(CF₃SO₃)₂]

[Ru(bpy)(CO)₂Cl₂] (0.5 g 1.3 mmol) in 1.2 dichlorobenzene (200 mL) was deaerated with dry nitrogen for 30 minutes resulting in a cloudy yellow solution. CF₃SO₃H (0.5 mL, 3.3 mmol) was added, dropwise with a glass pipette and the solution heated to 110° C. for 1.5 hr under nitrogen. The solution was then cooled to 0° C. and diethyl ether (200 mL) was added and stirred for 1 hr. The product was then filtered under a nitrogen blanket and washed with ether (2×5 mL), water (2×5 mL), and ether (2×5 mL). Yield: 0.51 g, 64.19%.

[Ru(bpy)(dPq)(CO)₂](PF₆)₂

[Ru(bpy)(CO)₂(CF₃SO₃)₂] (0.5 g, 0.8 mmol) and dipyrido [3,2-a:2',3'-c](6,7,8,9-tetrahydro)phenazine (dpqC, 0.464 g, 1.6 mmol) were dissolved in 95% ethanol (80 mL) under dry nitrogen. The solution was then refluxed for 1.5 hr and reduced to dryness by rotary evaporation. The residue was dissolved in boiling water and filtered to remove unreacted ligand (dpqC). A saturated solution of KPF₆ (~5 mL) was added to precipitate the compound. The resulting product was collected and washed with water (2×5 mL) and ether (2×5 mL). The compound was then recrystallised from acetone/ethanol and collected. Yield: 0.165 g, 23.1%. IR (Nujol) $V_{CO}$ at 2100 and 2050 cm⁻¹. ¹H NMR (δ-Acetone): 10.02 (dd, 2H), 9.78 (d, 1H), 9.66 (d, 1H), 9.06 (d, 1H), 8.78 (dd, 1H), 8.59 (dd, 1H), 8.34 (bm, 2H), 8.18 (bm, 2H), 7.82 (d, 1H), 7.49 (d, 1H), 3.34 (bm, 4H), 2.13 (b, 4H).

Resolution of Δ, Λ-[Ru(bpy)(dpqC)(CO)₂](PF₆)₂

[Ru(bpy)(dpqC)(CO)₂](PF₆)₂ (100 mg) was converted to the chloride salt by addition of N-butyl ammonium chloride in acetone. The product was then filtered from the solution and the chloride solution produce when the product was dissolved in water.

Sephadex SP-C25 chromatographic column was prepared and cycled with water for approximately 30 min. The compound was then loaded and cycling with water was continued for approximately 15 min. The column was then capped with additional Sephadex and the compound eluted with the addition of 0.1 M (−)dibenzoyl tartrate (pH 8.0) and the progress was monitored. Δ-[Ru(bpy)(dpqC)(CO)₂](PF₆)₂, Yield 15 mg (15.0%) CD $\lambda_{max}$ nm (Δε mdeg/M cm) (water/acetone): 265 (15); 290 (−1); 313 (17). Λ[Ru(bpy)(dpqC)(CO)₂](PF₆)₂ Yield 23 mg (23.0%)CD $\lambda_{max}$ nm ((Δ☐mdeg/M cm) (water/acetone): 265 (−17); 290 (3); 313 (−15); Optical purity at 88%.

Synthesis of [Ru(phen)₂ (4-Cl-Phen)](PF₆)₂

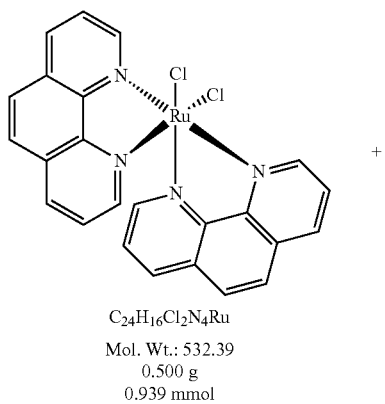

C₂₄H₁₆Cl₂N₄Ru
Mol. Wt.: 532.39
0.500 g
0.939 mmol

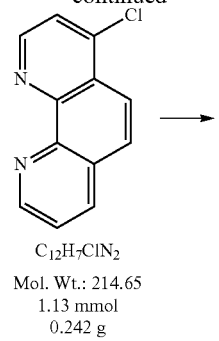

C₁₂H₇ClN₂
Mol. Wt.: 214.65
1.13 mmol
0.242 g

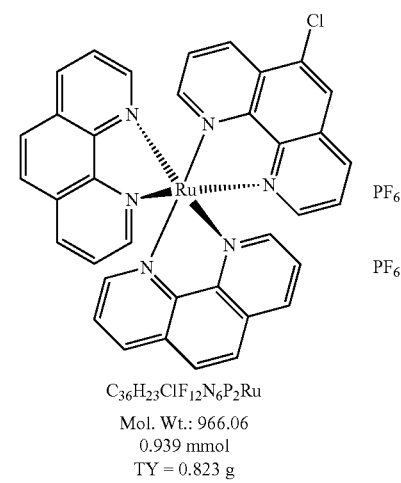

C₃₆H₂₃ClF₁₂N₆P₂Ru
Mol. Wt.: 966.06
0.939 mmol
TY = 0.823 g

[Ru(phen)(Cl)₂] (0.500 g, 0.939 mmol) and 4-chloro-1,10-phenanthroline (4-Cl-phen, 0.242 g, 1.13 mmol) were mixed in ethylene glycol (12 mL) and the solution was heated on high for five minutes in a modified microwave oven fitted with a reflux condenser. The reaction mixture was then poured into water (100 mL) and a solution of saturated of KPF₆ (1 mL) was added. The resulting precipitate was extracted into DCM (4×150 mL). The extracts were dried (sodium sulfate) and the solution evaporated. The dark orange solid was purified by column chromatography (Silica Gel 60 (230-400 mesh, Merck, 7×12 cm) with acetonitrile (containing 25% sat NH₄ PF₆ in acetonitrile). The acetonitrile was evaporated and water was added to afford precipitation. The product was collected by filtration and washed with ether (2×5 mL). The solid was redissolved in acetonitrile and purified on alumina (Activated neutral Brockmann 1, 7×12 cm) with acetonitrile twice. (0.385 g, 46.9%). ¹H NMR (CD₃CN): 8.66 (d, 2H), 8.60 (bm, 2H), 8.52 (d, 1H), 8.39 (d, 1H), 8.27 (s, 4H), 8.09 (dd, 2H), 8.03 (bm, 2H), 7.95 (d, 1H), 7.73 (d, 1H), 7.65 (bm, 5H).

Synthesis of [Ru(phen)₂(Phen-4-NH₂—CH₂CH₂—NH₂)](PF₆)₂

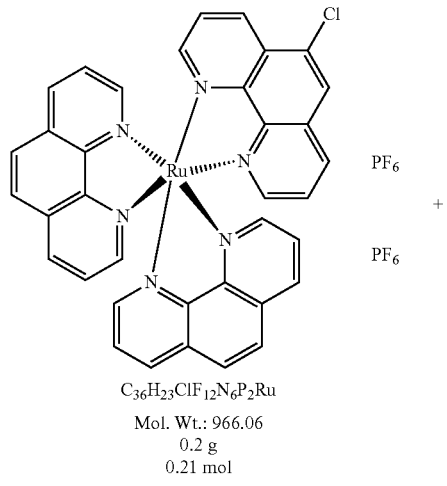

C₃₆H₂₃ClF₁₂N₆P₂Ru
Mol. Wt.: 966.06
0.2 g
0.21 mol

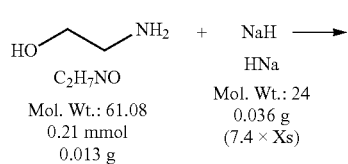

C₂H₇NO
Mol. Wt.: 61.08
0.21 mmol
0.013 g

NaH
HNa
Mol. Wt.: 24
0.036 g
(7.4 × Xs)

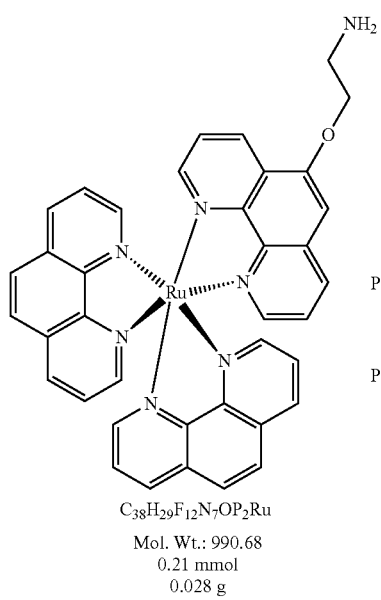

C₃₈H₂₉F₁₂N₇OP₂Ru
Mol. Wt.: 990.68
0.21 mmol
0.028 g

The ruthenium complex, [Ru(phen)₂4-Cl-Phen](PF₆)₂ (0.2 g, 0.21 mmol) was also suspended in deaerated DMF (5 mL) while separately NaH (0.036 g, 1.5 mmol) was also suspended in a stirring solution of dry, deaerated DMF (5 mL). Ethanolamine (12.8 L, 0.21 mmol) was added to the solution of NaH. The two solutions were mixed via cannula and the resulting black solution heated at 40° C. for 2 hr. The solution was evaporated to dryness under reduced pressure leaving a red black residue which was purified by flash chromatography on silica gel, eluting with acetonitrile (5% saturated KNO₃ solution and 10% water). Fractions containing unreacted starting complex and product were isolated by TLC (SiO₂, ACN/5% saturated KNO₃/10% H₂O). These fractions were combined, reduced to dryness then extracted into dichloromethane (4×100 mL) from H₂O (100 mL). The extracts were reduced to dryness and subsequently purified on a column of TLC grade silica gel (ACN/1% saturated KNO₃/10% H₂O). This purification achieved a separation of bands containing unreacted starting complex and product. The product (band 2) was collected, reduced to dryness then extracted into dichloromethane (4×100 mL) from H₂O (100 mL). Evaporation of the solution to dryness under reduced pressure gave the product as a deep red solid. $^1$H NMR (CD₃CN): 8.54 (d, 4H), 8.44 (dd, 2H), 8.28 (d, 1H), 8.23 (s, 4H), 8.18 (d, 1H), 8.08 (d, 1H), 8.00 (d, 1H), 7.83 (d, 1H), 7.76 (d, 1H), 7.65 (bm, 4H), 7.40 (dd, 1H), 6.70 (d, 1H), 6.38 (d, 1H), 1.30 (bs, 4H).

1-Methyl-4-nitropyrrole-2-carboxylic acid

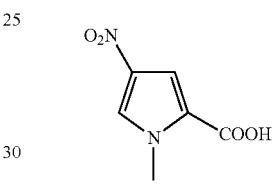

Acetic anhydride (20 mL) was treated with nitric acid (4.0 mL, 70%) and the mixture heated to 50° C. for 15 min then cooled to room temperature, and slowly added to a suspension of 1-methyl-2-pyrrolecarboxylic acid (4 g, 15.98 mmol) in of Ac₂O (12 mL) cooled to −25° C. The mixture was stirred at −15° C. for 0.5 hr, then the temperature was allowed to rise to ambient, and stirring was continued for 20 min. The mixture was again cooled to −25° C. and the precipitate collected in a funnel cooled with dry ice, the solid was washed with a small quantity of cold Ac₂O (−25° C.). The crystalline solid was taken up in water containing NaOH (1 g). Acidification with the HCl precipitated the pure compound. NMR as previously reported.

Methyl 1-methyl-4-nitropyrrole-2-carboxylate

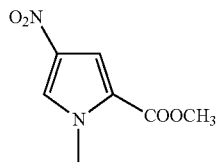

A cold solution of H₂SO₄ (2.9 mL) in MeOH (28.96 mL) was added to 1-methyl-4-nitropyrrole-2-carboxylic acid (2.897 g, 2.35 mmol). The mixture was refluxed for 24 hr. Water was added and the mixture extracted CHCl₃. The organic layer was dried (MgSO₄), and the solvent evaporated under vacuum to afford the creamy white product. NMR as previously reported.

Py/Py-COOCH₃

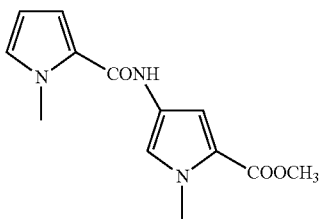

Methyl N-methyl-4-nitro pyrrole-2-carboxylate (0.5 g, 27.17 mmol) in MeOH (64 mL) and Pd/C (10%, 6 mg) was stirred under H₂ (1 atm) until the TLC showed no starting material (1 hr). The mixture was filtered through celite to remove the catalyst and DMF was added (3 mL). MeOH was removed under vacuum. N-methylpyrrole-2-carboxylic acid (1.3 mol equiv) was added followed by HOBT (88 mg, 1.5 mol equiv), TBTU (209 mg, 1.5 equiv) and Et₃N (220 mg, 5 equiv). The solution was stirred for 1 hr at room temperature and the solvent removed under vacuum. The residue was purified by flash chromatography (100% DCM).

Py/Py-COOH

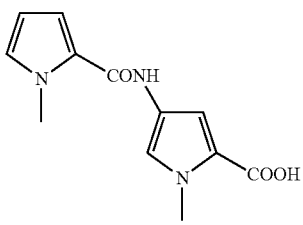

Py/Py-COOCH₃ (360 mg, 1.38 mmol) in THF/MeOH (1.1/7.5 mL) was added LiOH (1 M, 5.5 mL) and the solution stirred at 60° C. (oil bath) for 1.5 hr and monitored by TLC (10%, MeOH/CH₂Cl). The organics were evaporated under vacuum, the solution cooled and acidified with HCl (1 M 5 mL). The solid was collected and air dried and left in a desiccator under vacuum overnight. NMR as previously reported.

NO₂-Py/Py-COOCH₃

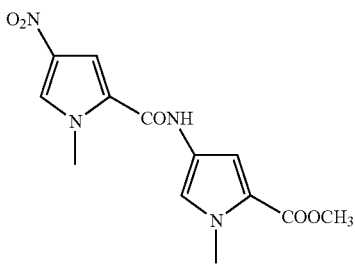

NO₂-Py-COOCH₃ (1.45 g, 7.83 mmol) in MeOH (150 mL) and Pd/C (174 mg) was stirred under H₂ (1 atm) for 1 hr. The mixture was the filtered through celite and DMF (3 mL) added. MeOH was removed under vacuum. NO₂-Py-COOH (1.8 g,) was added followed by HOBT (255.2 mg, 1.89 mmol) and TBTU (606 mg, 1.89 mmol) and Et₃N (638 mg, 6.32 mmol). The solution was stirred for 1 hr at room temp and the solvent (DMF) removed under vacuum until a small quantity remained. The pure compound was precipitated by addition of MeOH. %). ¹H NMR (d-DMSO): 10.21 (s, 1H), 8.15 (d, 1H), 7.53 (d, 1H), 7.43 (d, 1H), 6.88 (d, 1H), 3.94 (s, 3H), 3.84 (s, 3H), 3.73 (s, 3H).

Py/Py/Py/Py-COOCH₃

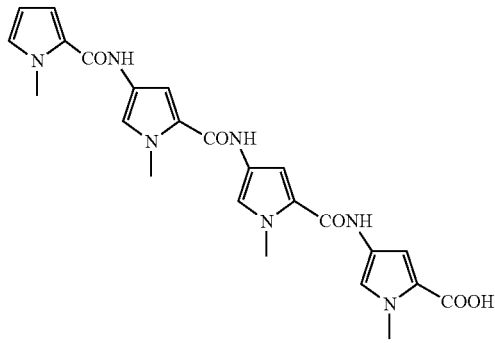

NO₂-Py/Py-COOCH₃ (213 mg, 0.69 mmol) was dissolved in DMF (25 mL) and added Pd/C catalyst (15 mg) and stirred under H₂ until the amine was formed. The mixture was filtered through celite and Py/Py-COOH (166 mg, 0.66 mmol) added to the solution followed by HOBT (22 mg, 0.16 mmol), TBTU (51 mg, 0.16 mmol) and Et₃N (53 mg, 0.52 mmol). The reaction was then left to couple for 1.5 hr. The DMF was removed under reduced pressure to yield the compound.

Py/Py/Py/Py-COOH

Py/Py/Py/Py-COOCH₃ (100 mg, 0.20 mmol) in DMF (10 mL) was added NaOH (0.75 mL) and the solution stirred at 60° C. for 1 hr. The organics were evaporated until approx. 3 mL remained and acidified with HCl (1 M, 5 mL) to yield the product.

[Ru(phen)₂(phen-4-O—CH₂CH₂NHCO-Py/Py/Py/Py](PF₆)₂

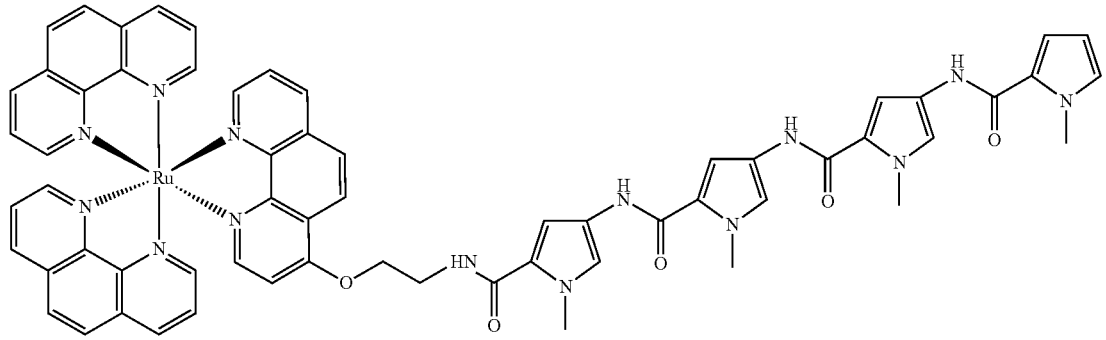

[Ru(phen)₂(phen-4-O—CH₂CH₂NH₂](PF₆)₂ (28 mg, 0.03 mmol) dissolved in DMF (25 mL) and added Pd/C catalyst (15 mg) and stirred under H₂ until the amine was formed. The mixture was filtered through celite) and Py/Py/Py/Py-COOH (75 mg, 0.15 mmol) added to the solution followed by HOBT (22 mg, 0.16 mmol), TBTU (51 mg, 0.16 mmol) and Et₃N (53 mg, 0.52 mmol). The reaction was then left to couple for 2 hr. The DMF was removed under reduced pressure to yield the compound.

The invention claimed is:

1. A compound of formula (1)

or a salt thereof,
wherein
M¹ and M² are the same or different and are each a metal coordination complex selected from the group consisting of a platinum complex, a palladium complex, a ruthenium complex, and a rhodium complex, wherein at least one of M¹ and M² is capable of interacting with a major groove or minor groove of a polynucleotide;

P¹ and P² are the same or different and are each a pyrrole-imidazole polyamide, wherein each pyrrole-imidazole polyamides (P¹, P²) independently comprises a plurality of heterocyclic rings selected from the group consisting of optionally substituted N-methylimidazole (Im), optionally substituted N-methylpyrrole (Py) and optionally substituted 3-hydroxy N-methylpyrrole (Hp);

T¹, T² and T³ are the same or different and are each a linker group having the formula (2)

wherein
Y¹ and Y² may be the same or different and are independently selected from NH, —NH₂, C═O, C═S, C═NH, O, OH, S, SH, S(O), S(O)₂, NR³, NHR³, N(R³)₂, an optionally substituted cycloalkylamine, an optionally substituted cycloalkyldiamine, and an optionally substituted heteroaryl group; where each R³ is independently selected from the group consisting of alkyl, cycloalkyl, aryl and heteroaryl;

A is selected from the group consisting of an optionally substituted $C_{1-10}$ alkylene, an optionally substituted $C_{2-10}$ alkenylene, an optionally substituted $C_{2-10}$ alkynylene, an optionally substituted $C_{3-6}$ cycloalkylene, an optionally substituted $C_{6-10}$ aryl, C═O, C═S, and C═NH, NH, O, S, NH₂, OH, SH, S(O), S(O)₂, amino acids, and spermidine; and n is an integer selected from 1 to 20,
wherein when n is an integer greater than 1, each (A) group may be the same or different;

a is 0, or 1;

b is an integer selected from 1, 2, 3, 4 and 5;
wherein when b is an integer greater than 1, each P¹, each T² and each M² may be the same or different; and c is 0, 1 or 2; wherein when c is 2, each P² may be the same or different and each T³ may be the same or different;

wherein said compound is selected from the group consisting of

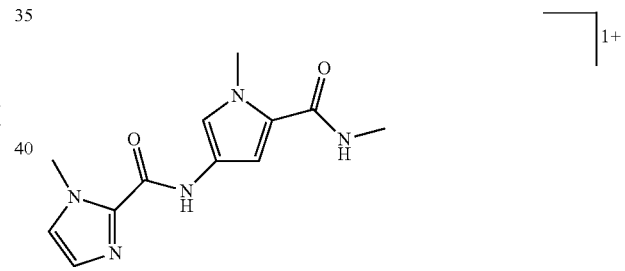

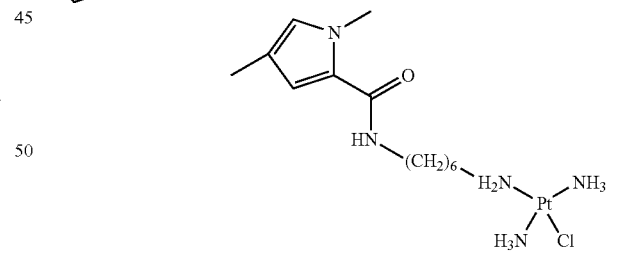

"trans-Im/Py/Py-[CONH(CH₂)₆-NH₂)Pt(NH₃)₂Cl";

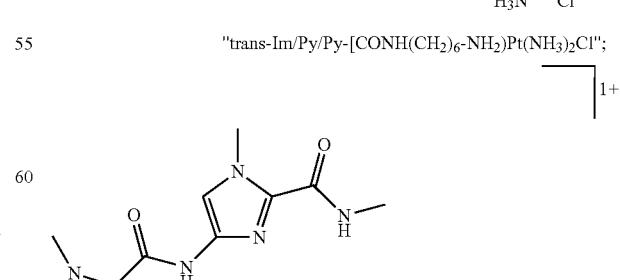

75
-continued

"trans-Im/Py/Py-[CONH(CH₂)₂-NH₂)Pt(NH₃)₂Cl]";

76
-continued

77
-continued
78
-continued
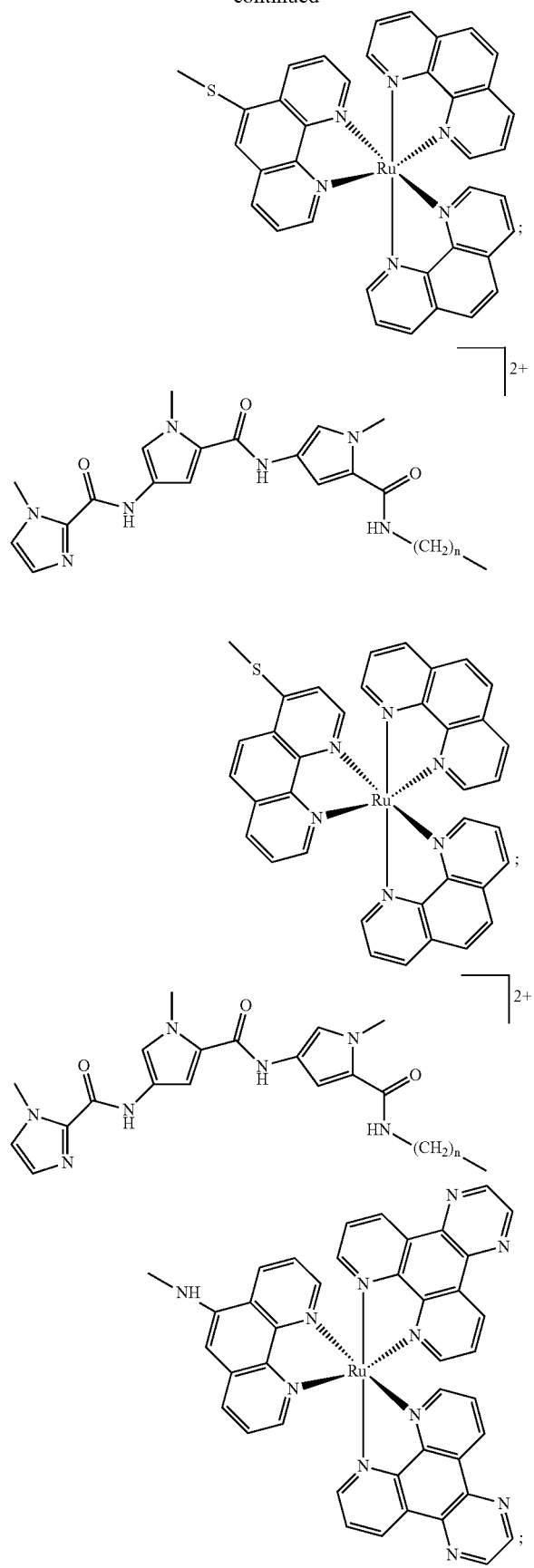
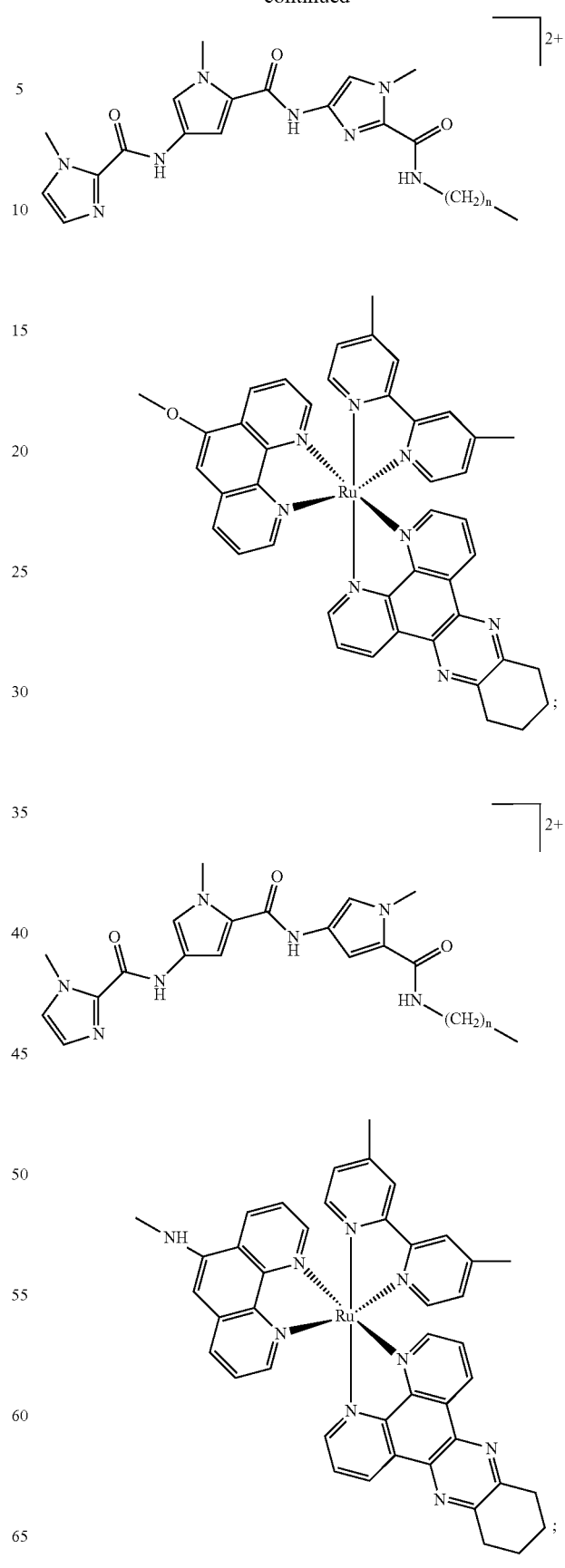

79
-continued
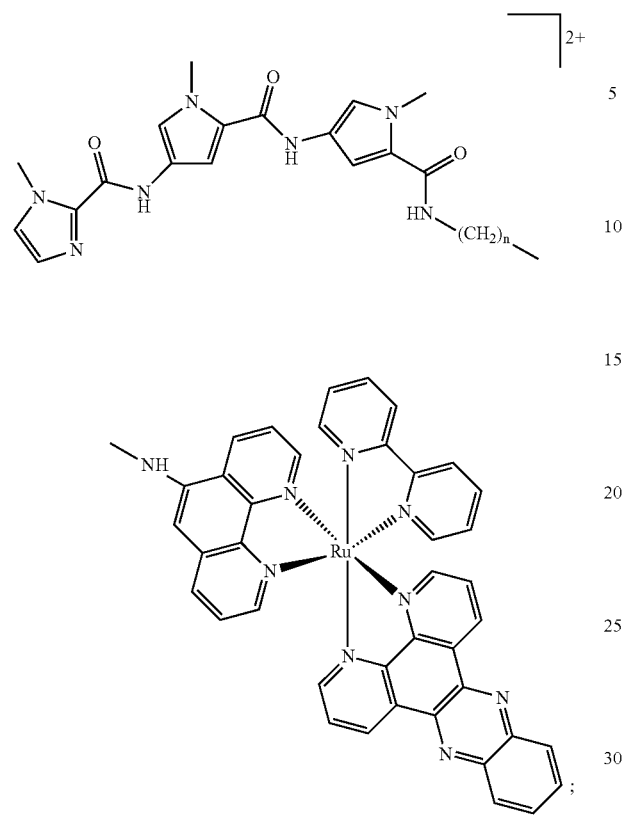
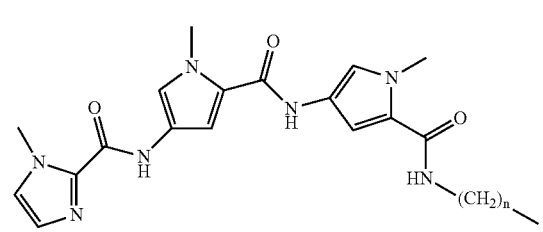
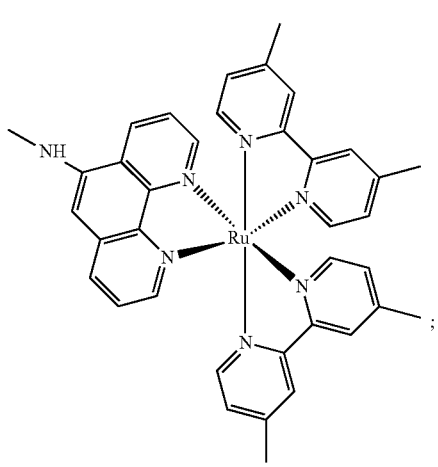
80
-continued
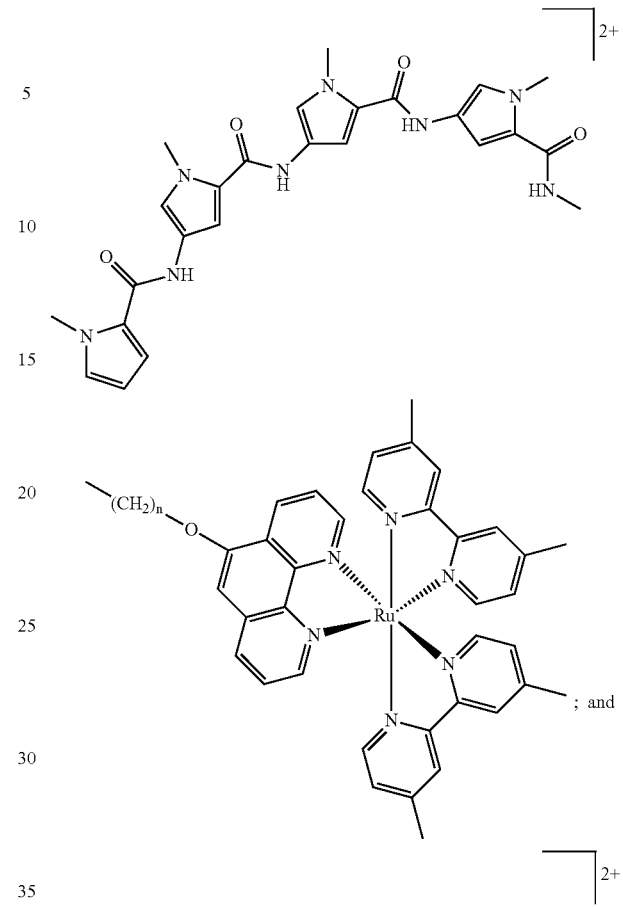
; and
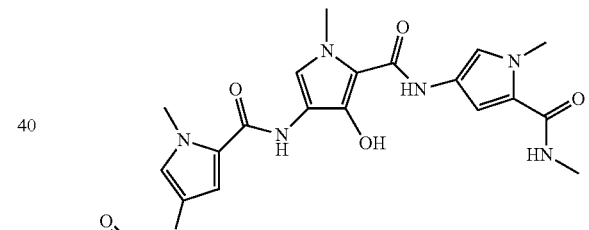
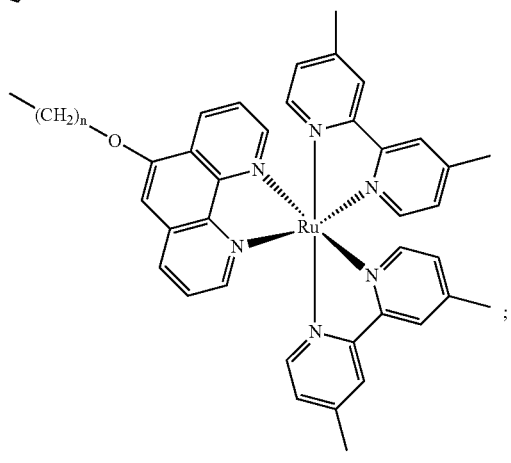
;

where n is an integer selected from 1, 2, 3, 4, 5, 6, 7, 8, 9 and 10, or a salt thereof.

2. A pharmaceutical composition comprising at least a compound of formula (1) according claim 1, together with a pharmaceutically acceptable diluent, adjuvant or carrier.

* * * * *